(12) United States Patent
Shaughnessy, Jr. et al.

(10) Patent No.: US 8,124,087 B2
(45) Date of Patent: *Feb. 28, 2012

(54) METHODS OF CONTROLLING BONE LOSS BY INHIBITING DKK1

(75) Inventors: John D. Shaughnessy, Jr., Roland, AR (US); Bart Barlogie, Little Rock, AR (US); Ya-wei Qiang, Little Rock, AR (US)

(73) Assignee: Board of Trustees of the University of Arkansas, Little Rock, AK (US)

( * ) Notice: Subject to any disclaimer, the term of this patent is extended or adjusted under 35 U.S.C. 154(b) by 42 days.

This patent is subject to a terminal disclaimer.

(21) Appl. No.: 12/008,771

(22) Filed: Jan. 14, 2008

(65) Prior Publication Data

US 2008/0267950 A1 Oct. 30, 2008

Related U.S. Application Data

(63) Continuation-in-part of application No. 11/176,739, filed on Jul. 7, 2005, now Pat. No. 7,642,238, which is a continuation-in-part of application No. 10/727,461, filed on Dec. 4, 2003, now Pat. No. 7,459,437.

(60) Provisional application No. 60/431,040, filed on Dec. 5, 2002.

(51) Int. Cl.
*A61K 39/00* (2006.01)

(52) U.S. Cl. .............. 424/139.1; 424/130.1; 424/133.1; 424/135.1; 424/141.1; 424/142.1

(58) Field of Classification Search .................. None
See application file for complete search history.

(56) References Cited

U.S. PATENT DOCUMENTS

| 7,371,736 B2 * | 5/2008 | Shaughnessy et al. ..... 514/44 A |
| 7,642,238 B2 * | 1/2010 | Shaughnessy .................. 514/12 |
| 2007/0128187 A1 * | 6/2007 | Allen et al. ................ 424/143.1 |

FOREIGN PATENT DOCUMENTS

WO  WO 02/092015 A1 * 11/2002

OTHER PUBLICATIONS

Kazanskaya et al. (2000, Development 127:4981-4992).*

\* cited by examiner

*Primary Examiner* — Elizabeth C Kemmerer

(57) ABSTRACT

The present invention is drawn to understanding lytic bone diseases. In this regard, the present invention discloses mechanism by which Wnt signaling antagonist inhibits bone differentiation. Also disclosed herein are methods to control bone loss, treat bone disease and prevent tumor growth in bones of individual.

7 Claims, 54 Drawing Sheets
(4 of 54 Drawing Sheet(s) Filed in Color)

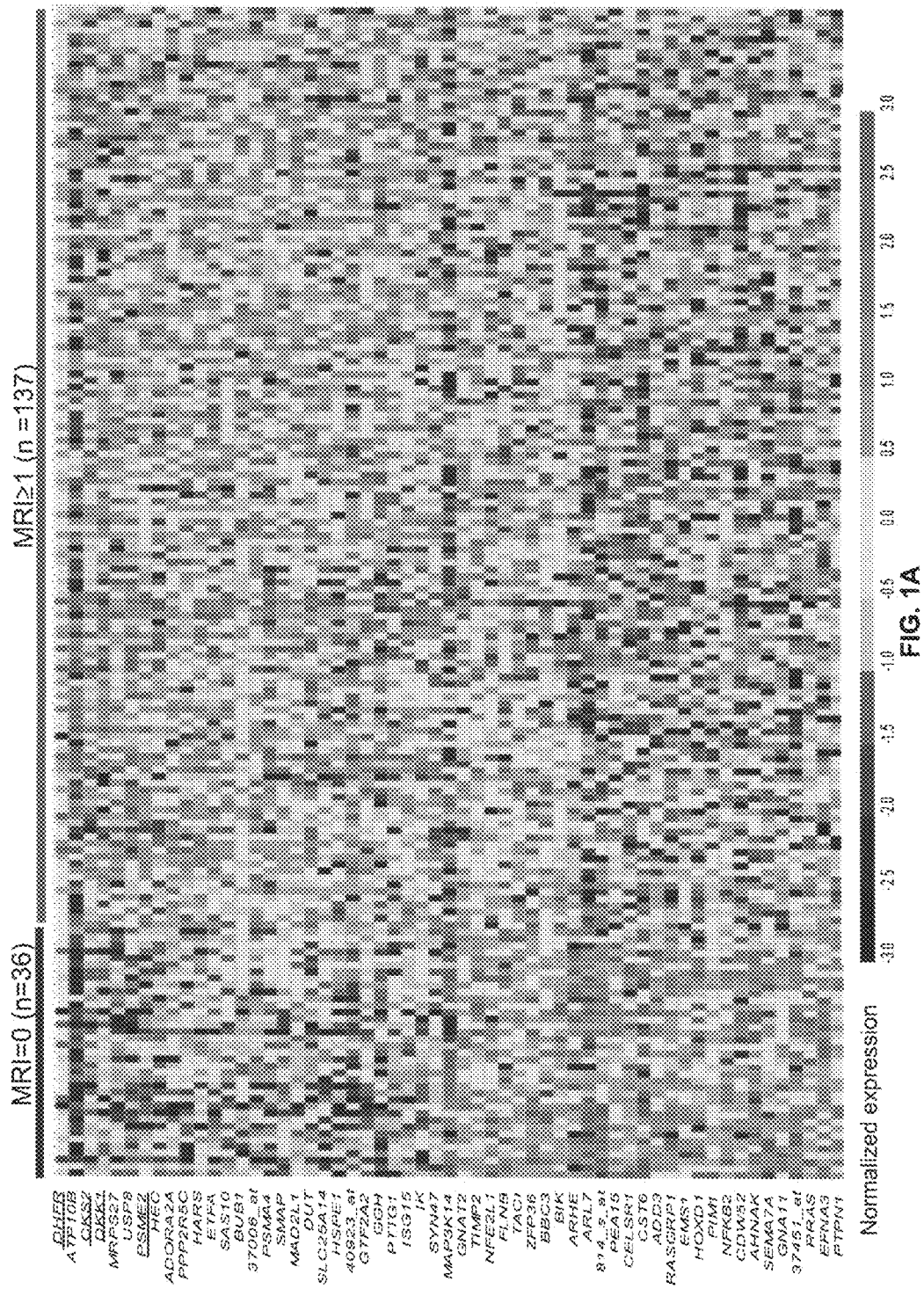

NO BONE DISEASE    BONE DISEASE

150 Newly Diagnosed MM

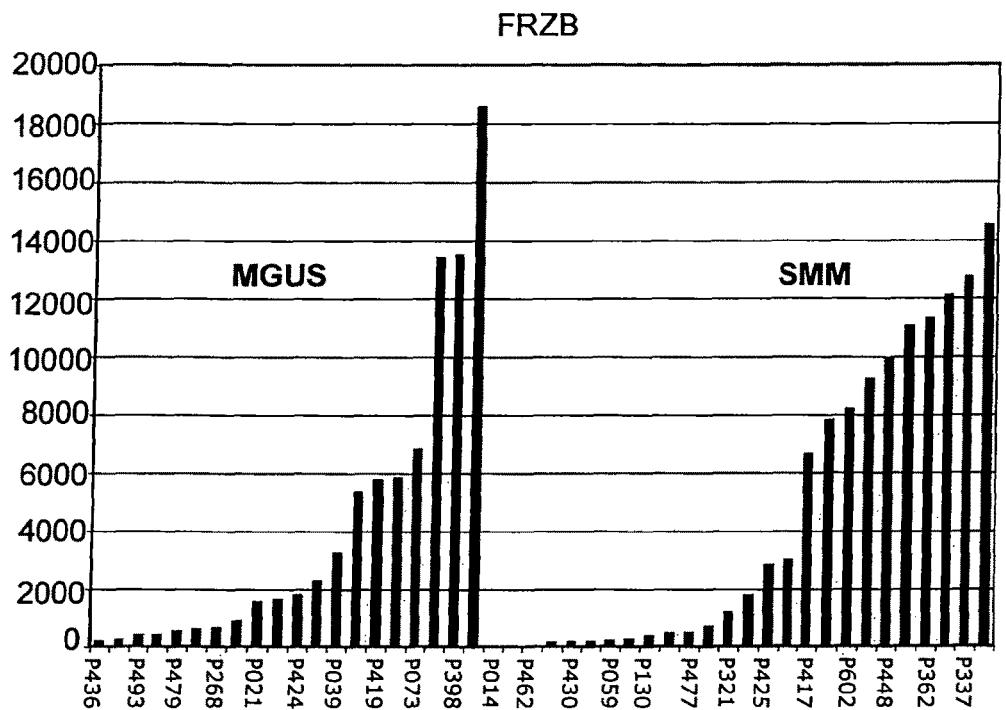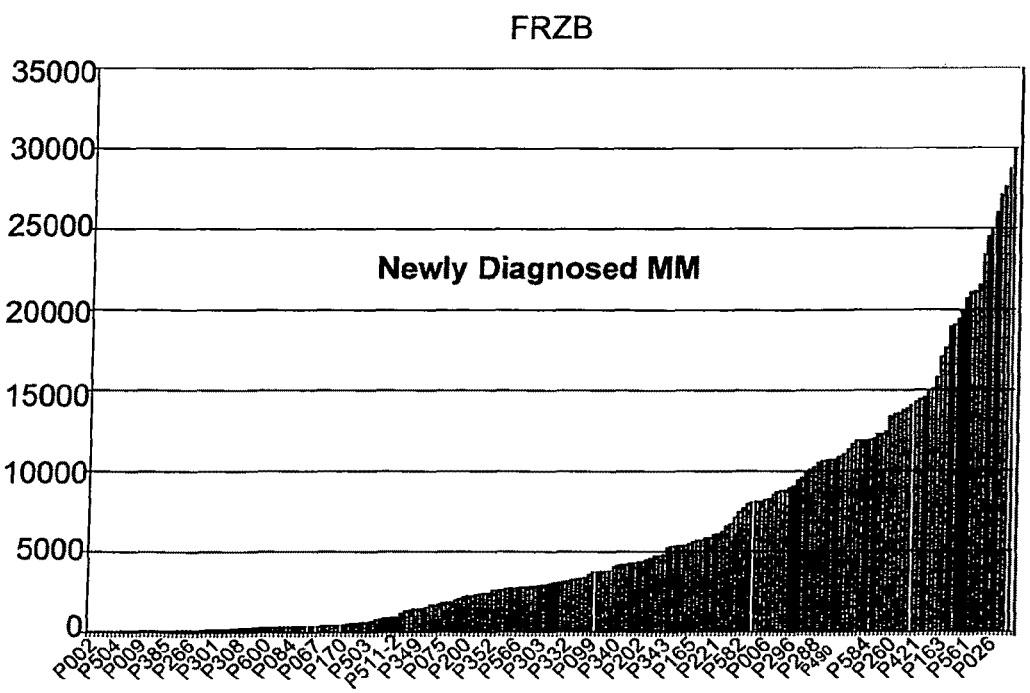
Fig. 13

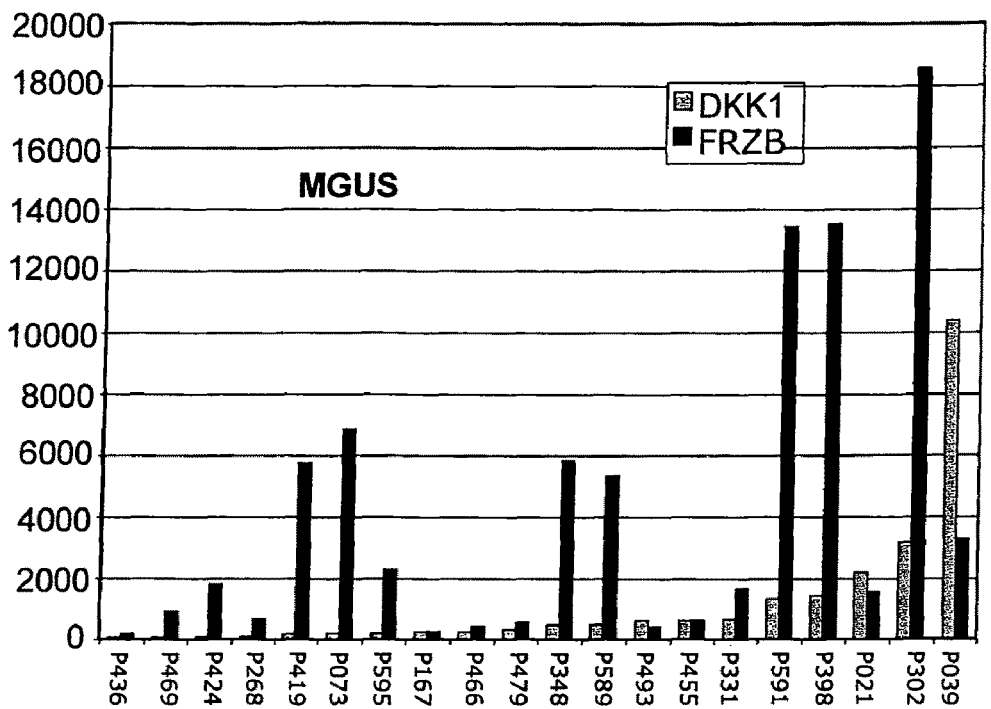
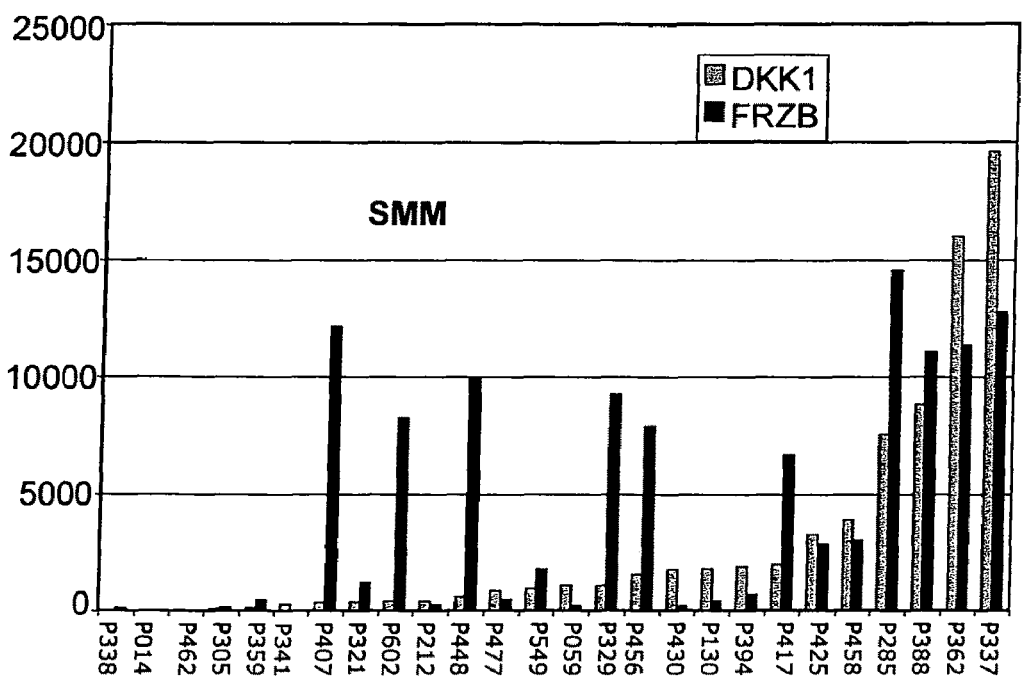
Fig. 14

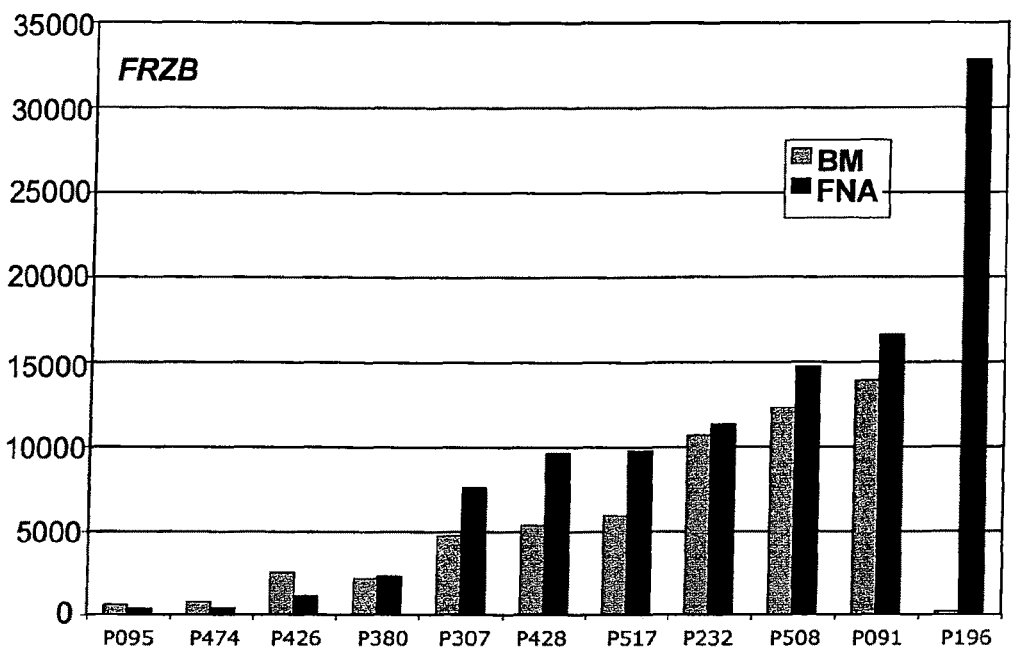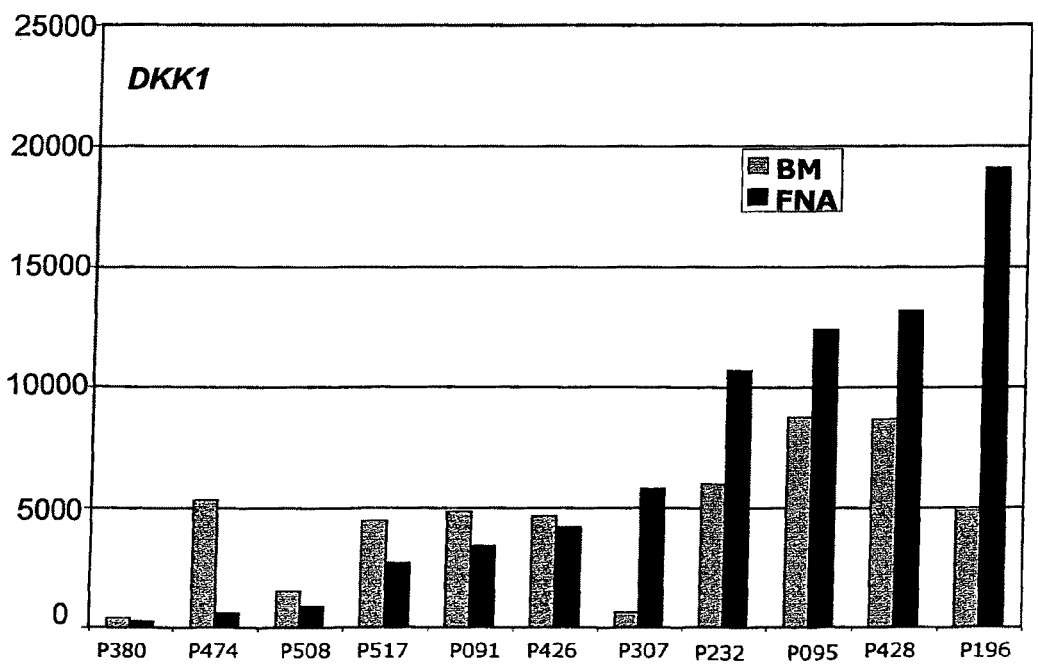
Fig. 16

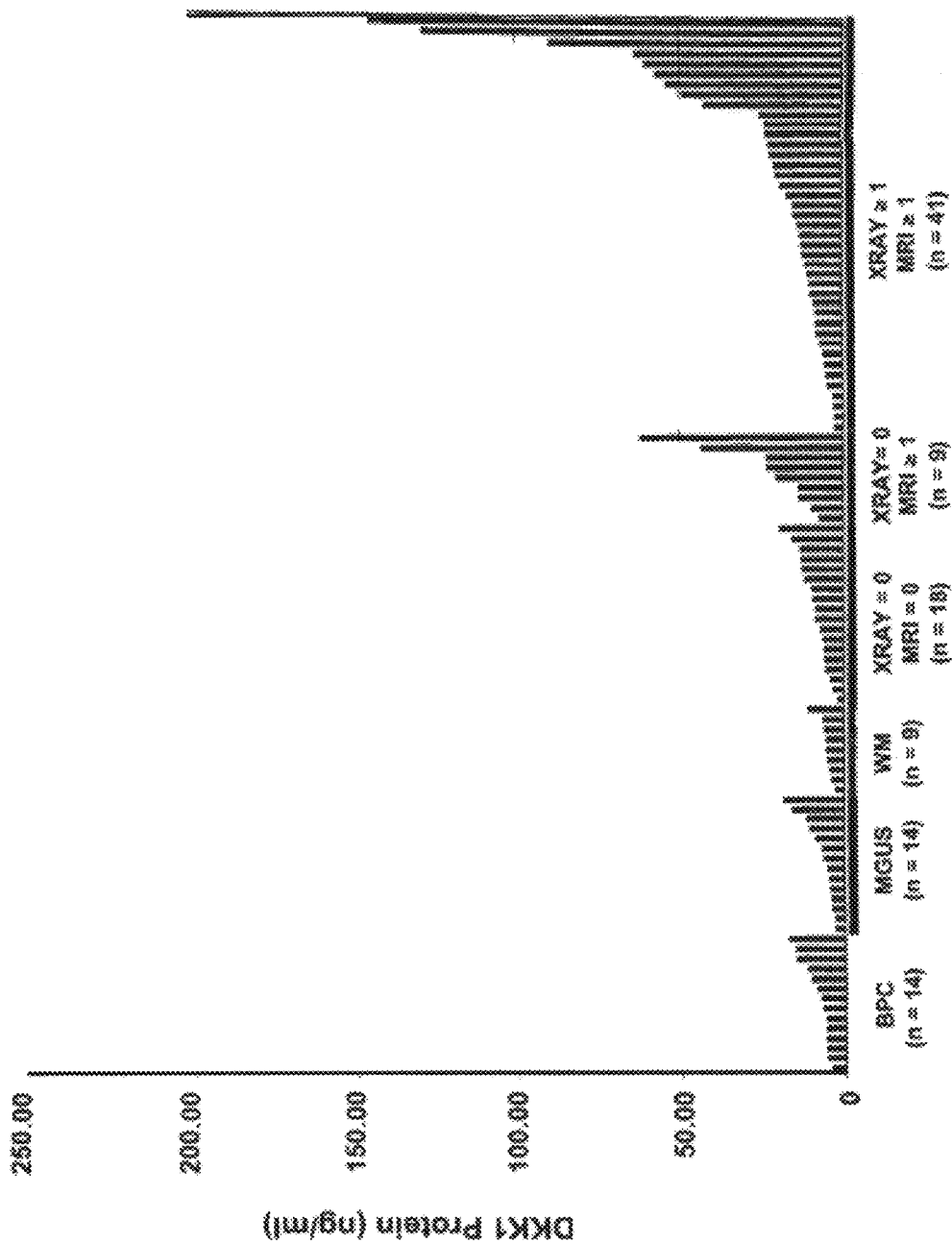

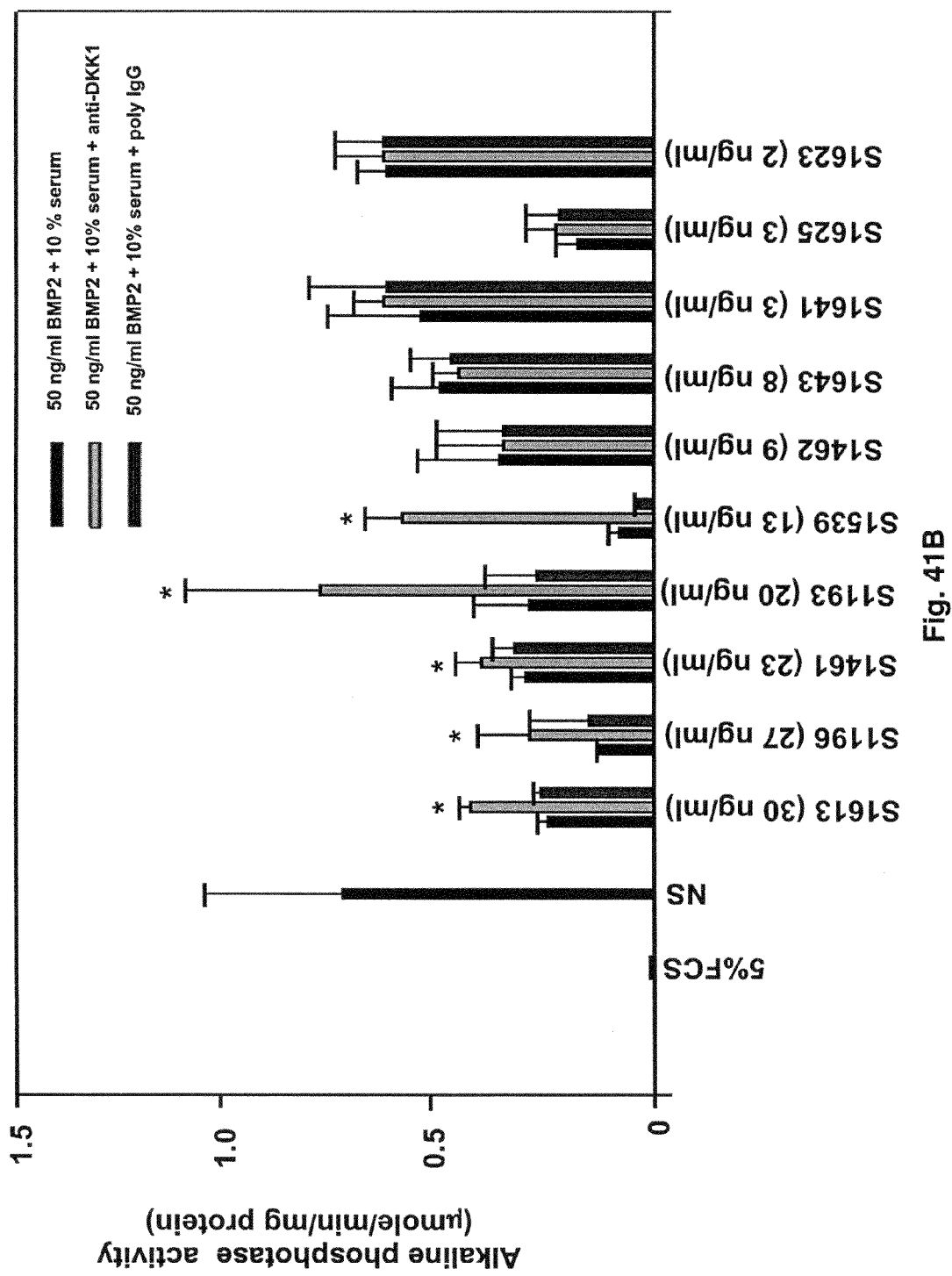

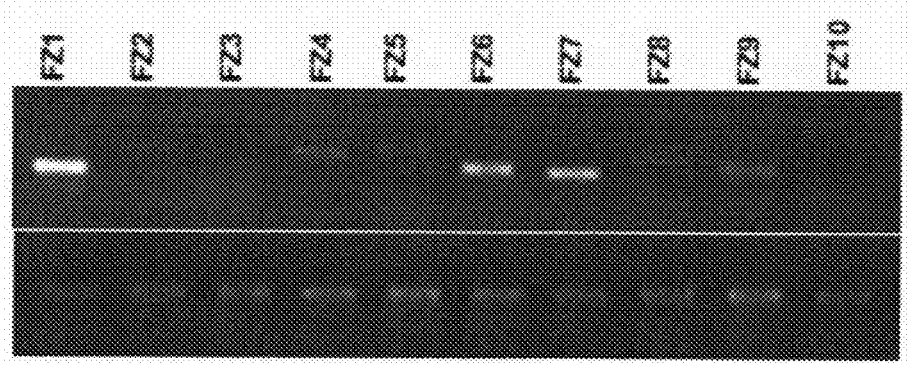
Fig.42A (panel a)
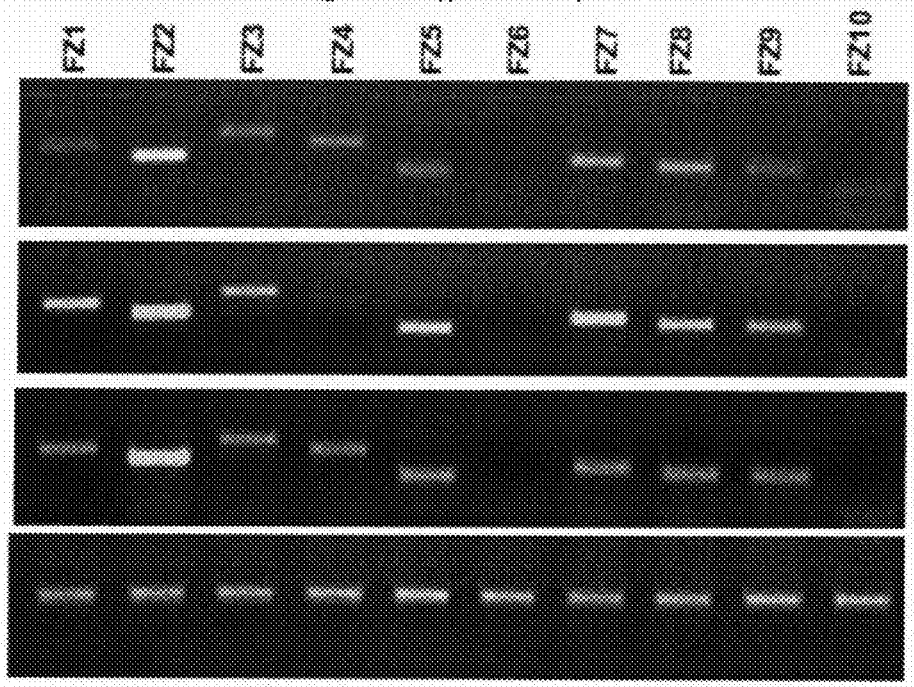
Fig.42A (panel b)
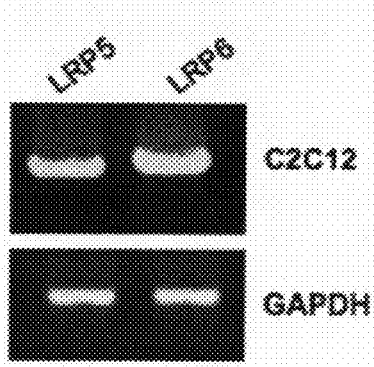
Fig.42A (panel c)
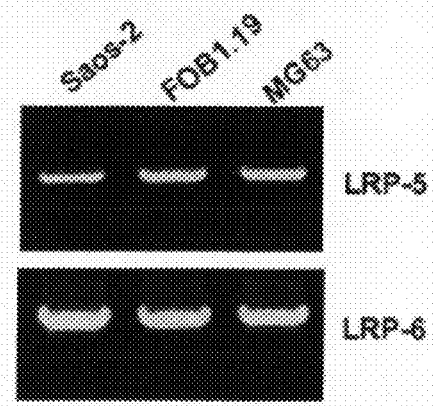
Fig.42A (panel d)

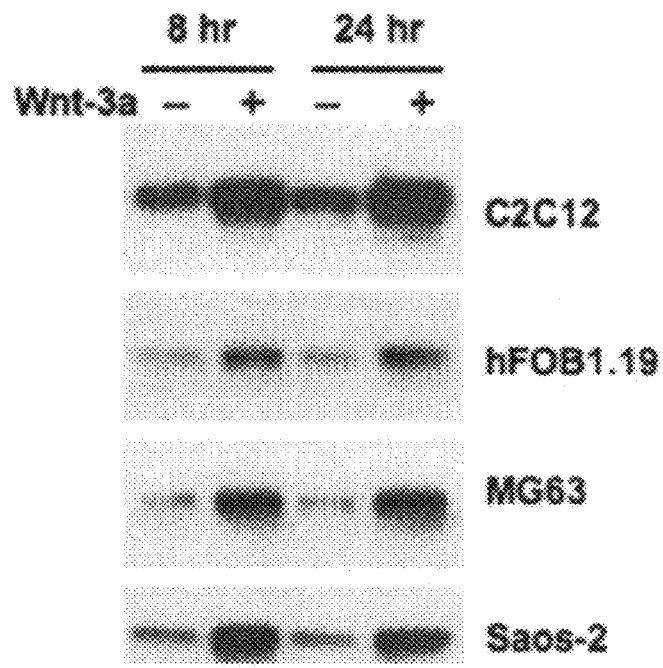
Fig. 42B (panel a)
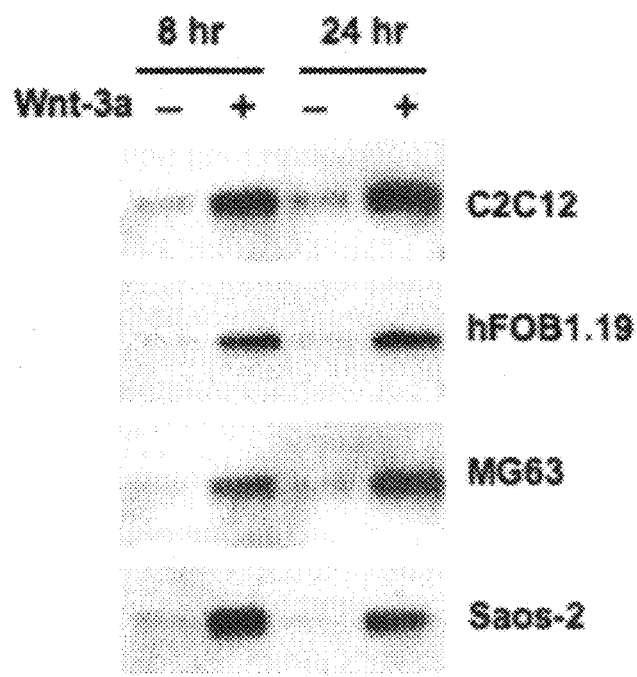
Fig. 42B (panel b)

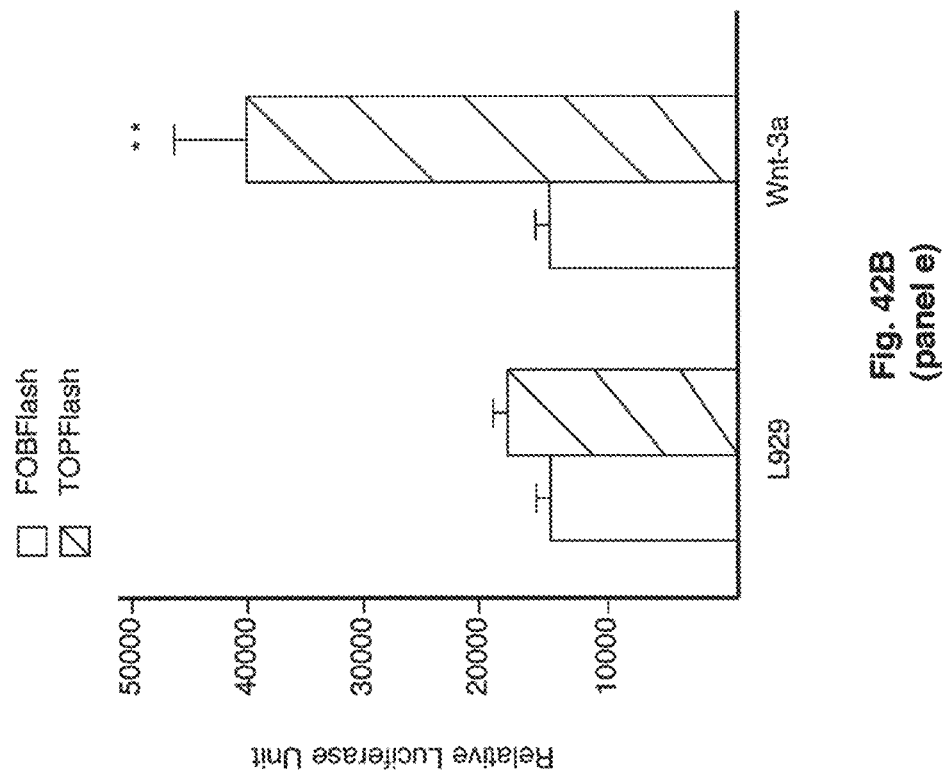
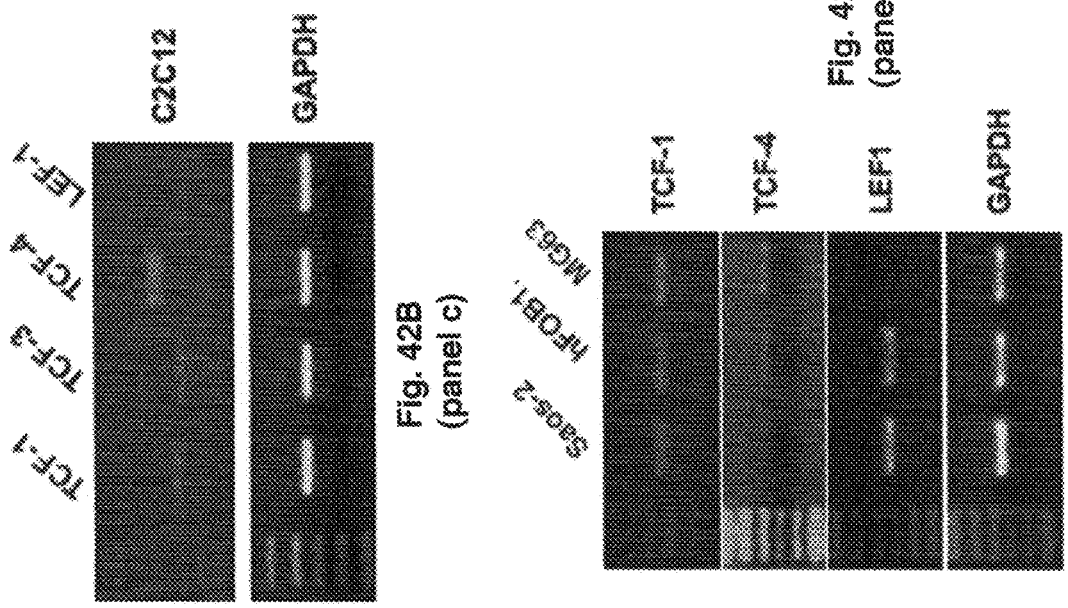

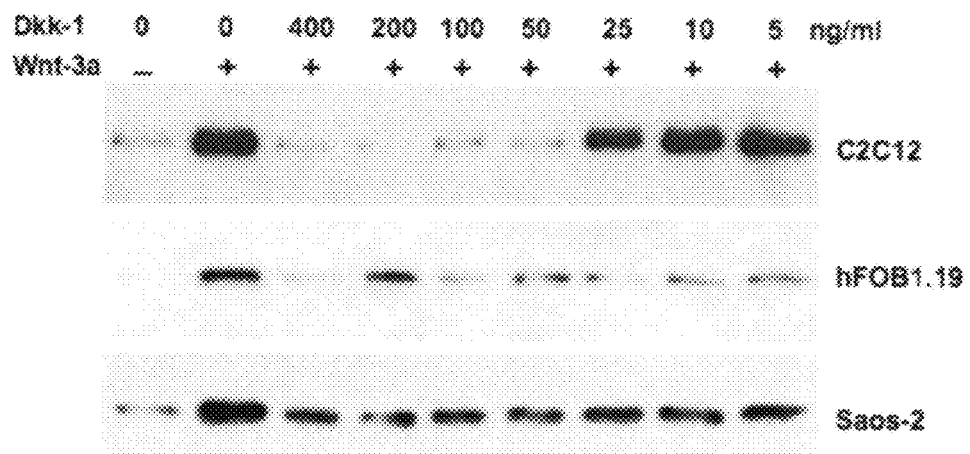
Fig. 42C (panel a)
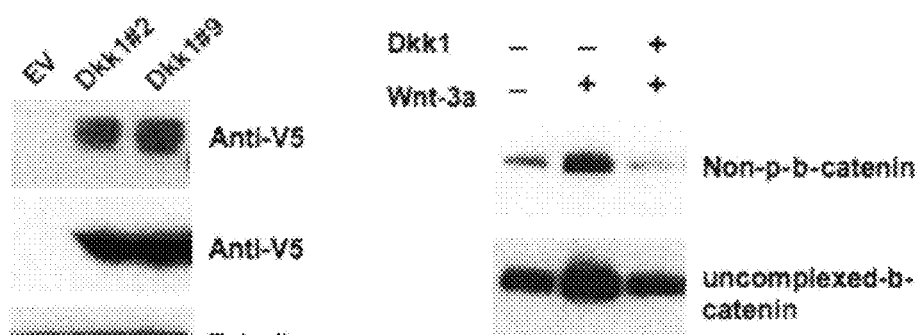
Fig. 42C (panel b)
Fig. 42C (panel c)
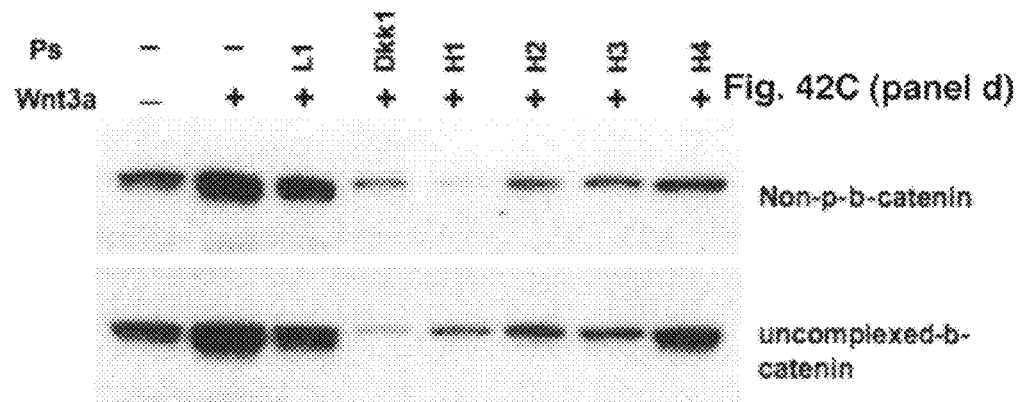
Fig. 42C (panel d)

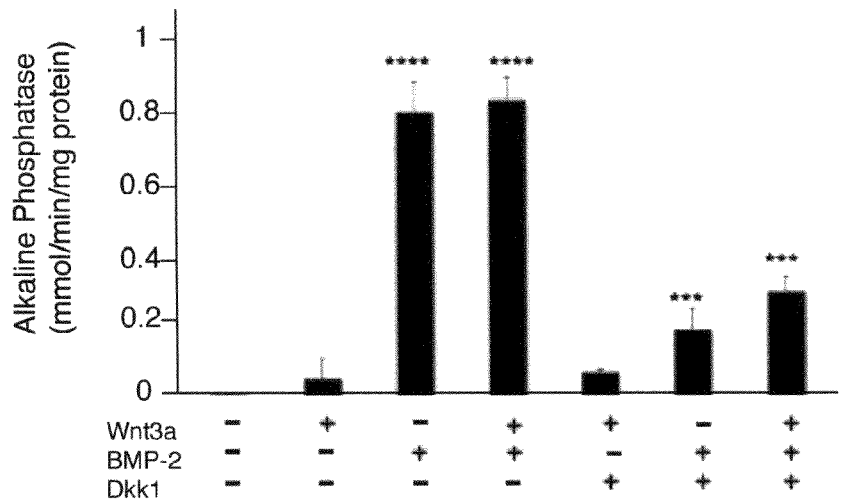
Fig. 42D (panel a)
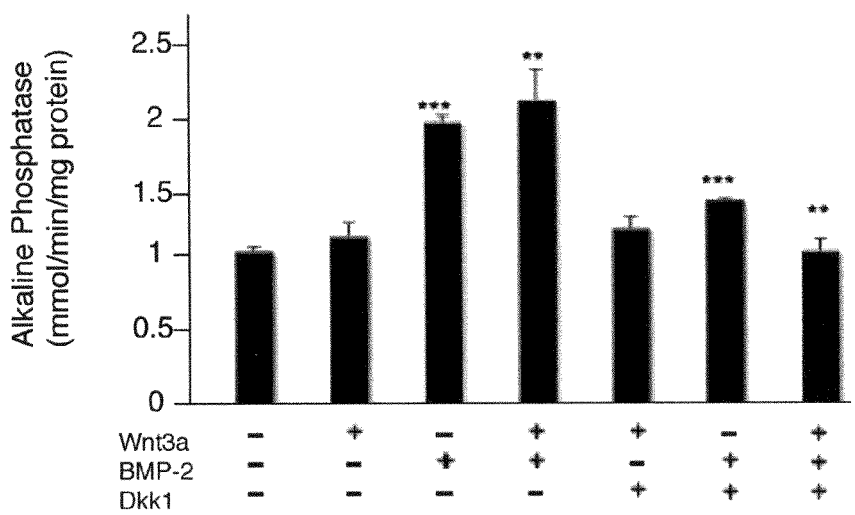
Fig. 42D (panel b)
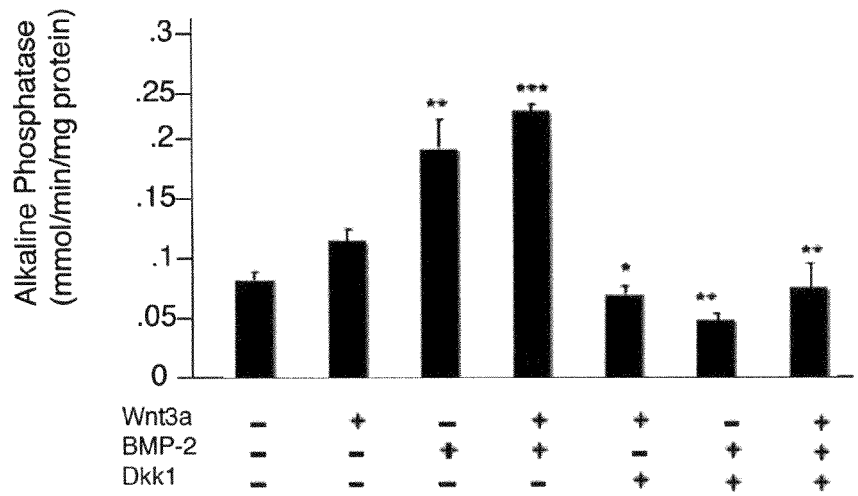
Fig. 42D (panel c)

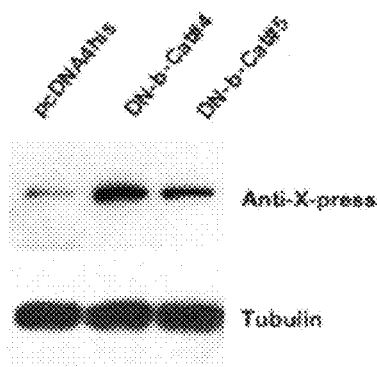
Fig. 42E (panel a)
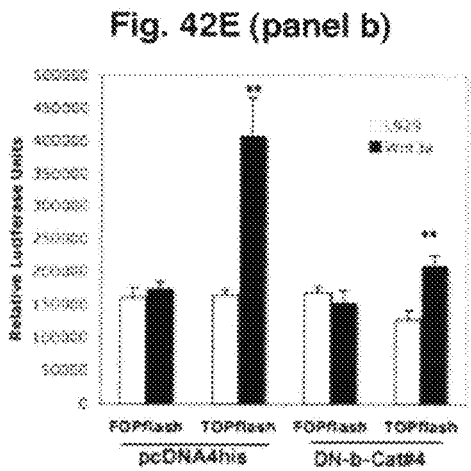
Fig. 42E (panel b)
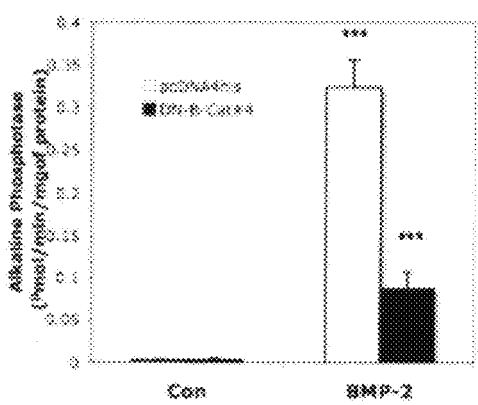
Fig. 42E (panel c)
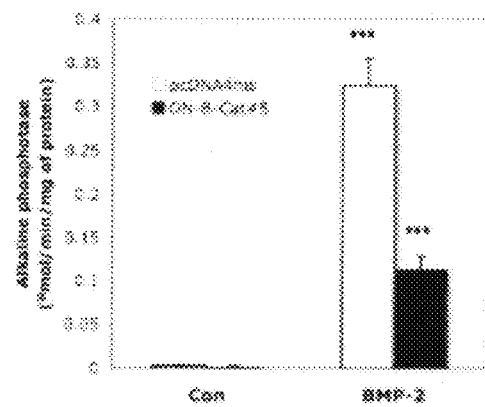
Fig. 42E (panel d)

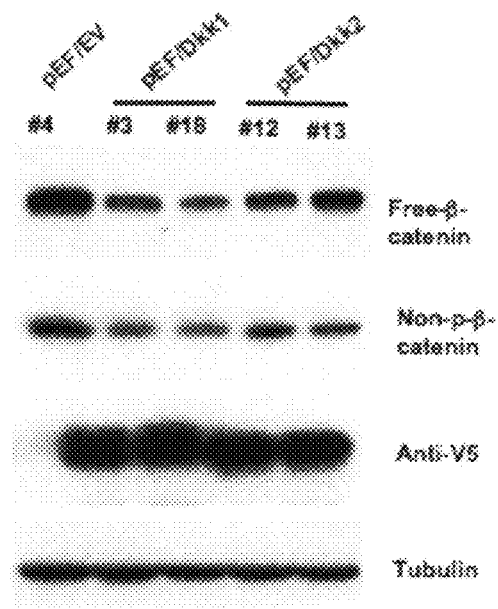
Fig. 42E (panel e)
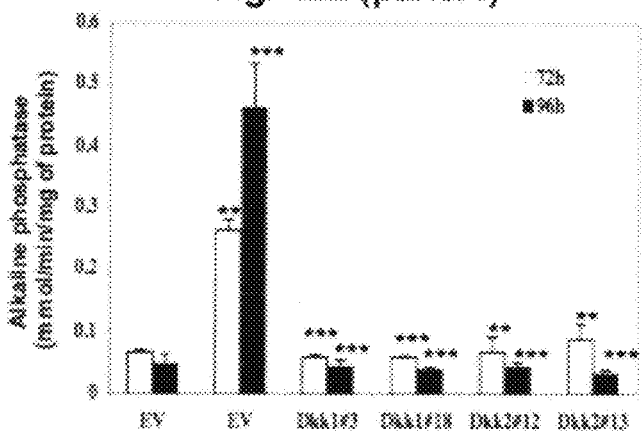
Fig. 42E (panel f)
Fig. 42G (panel b)
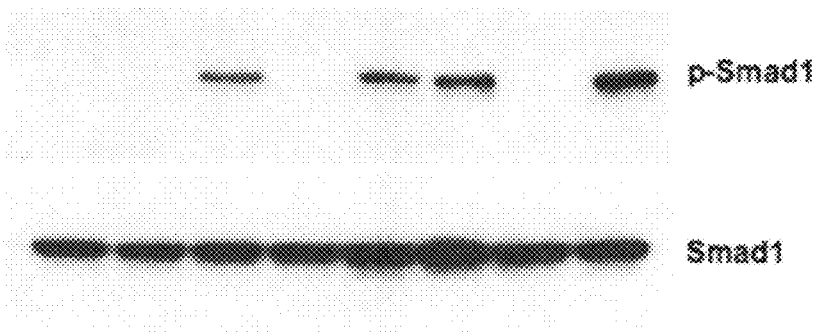

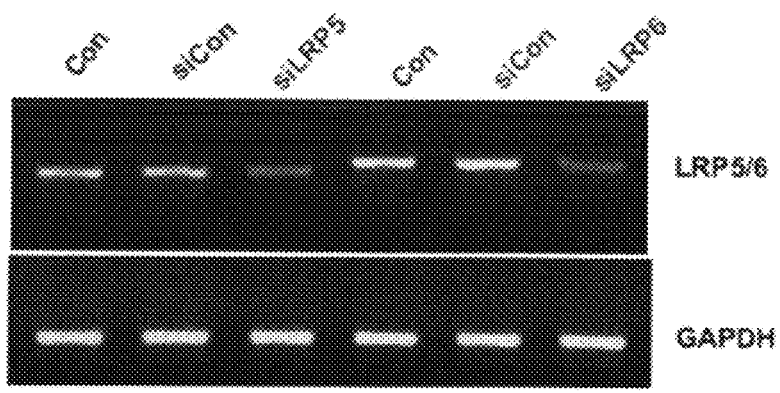
Fig.42F (panel a)
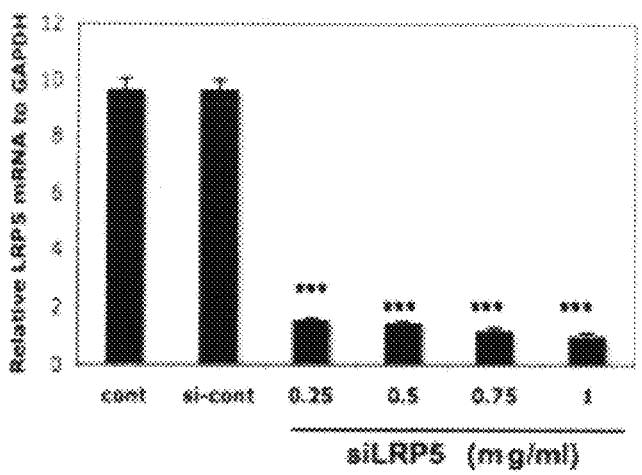
Fig.42F (panel b)
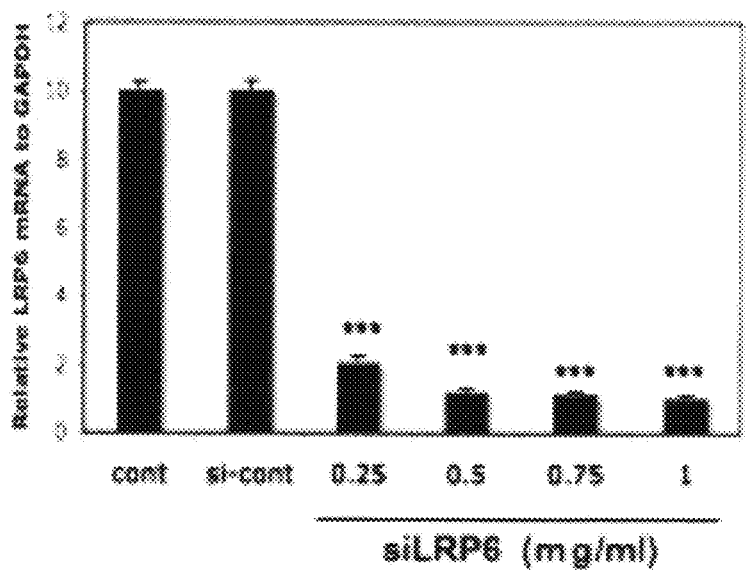
Fig.42F (panel c)

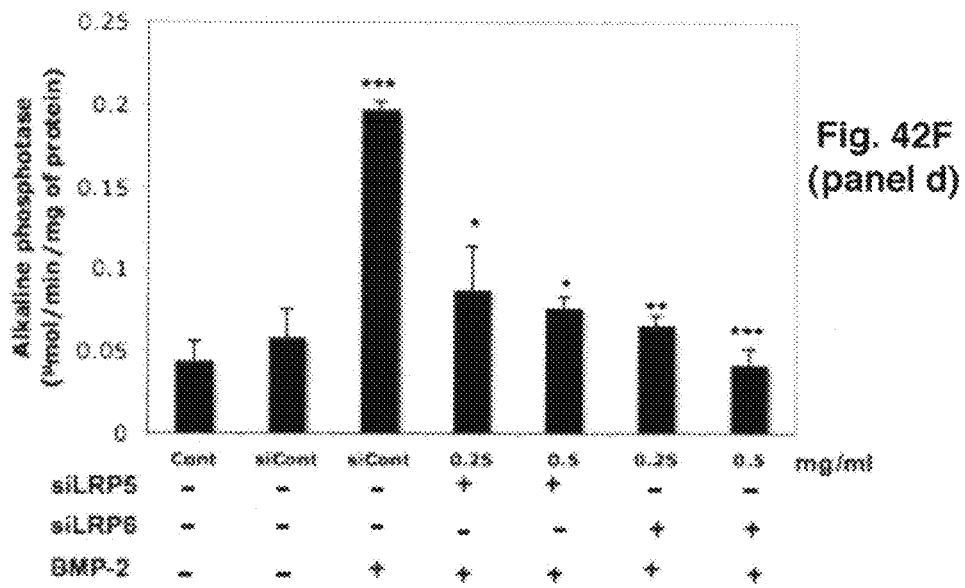
Fig. 42F (panel d)
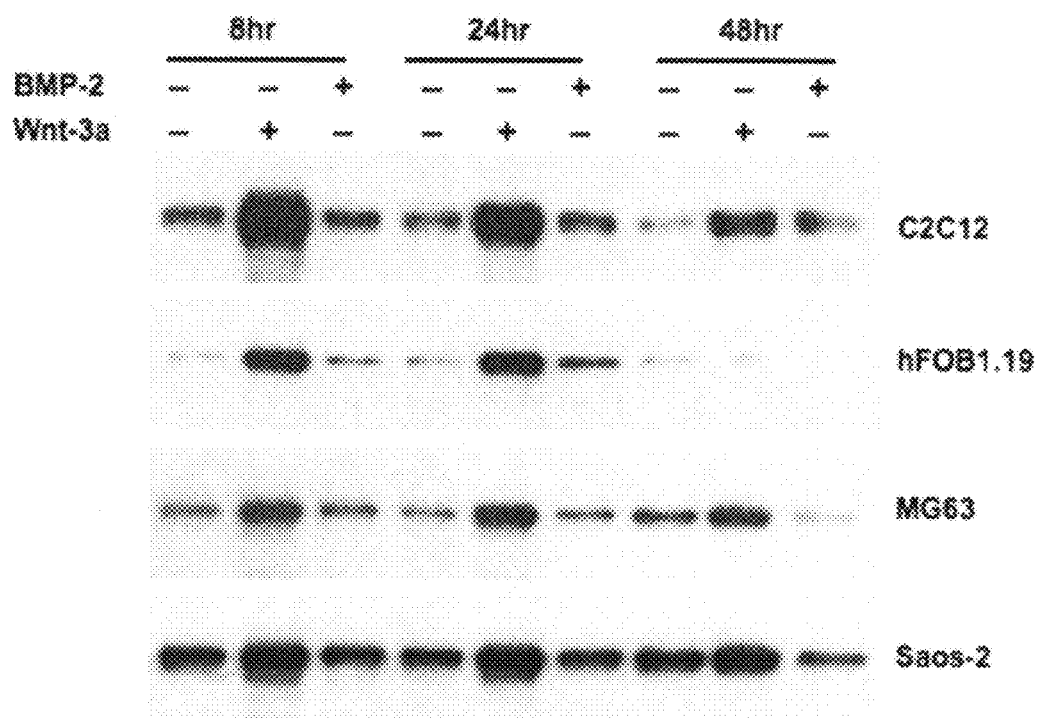
Fig. 42G (panel a)

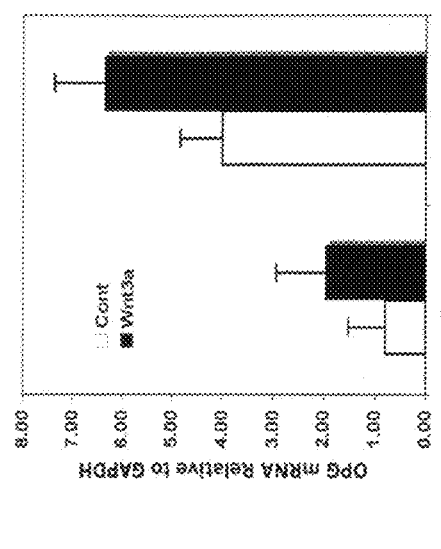
Fig.43A (panel a)
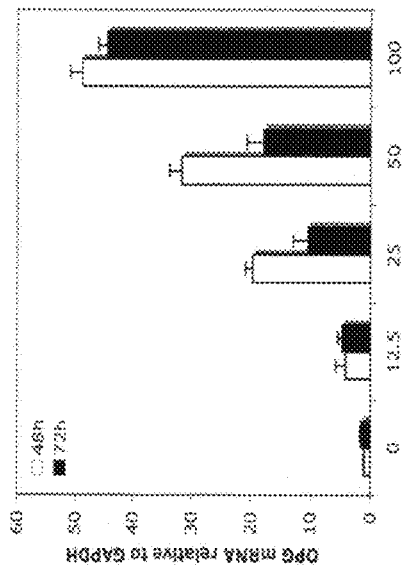
Fig.43A (panel b)
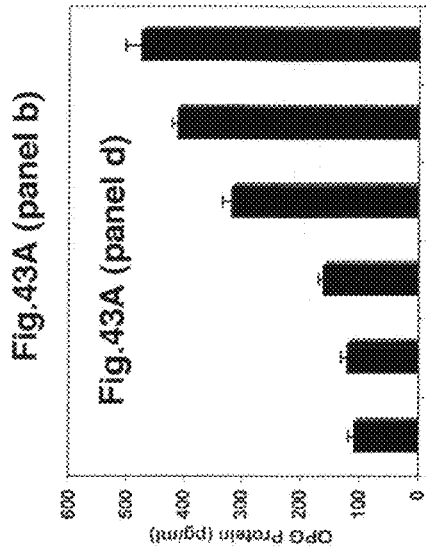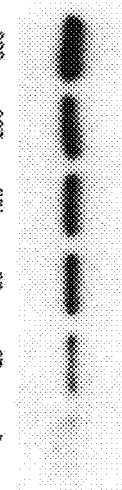
Fig.43A (panel c)
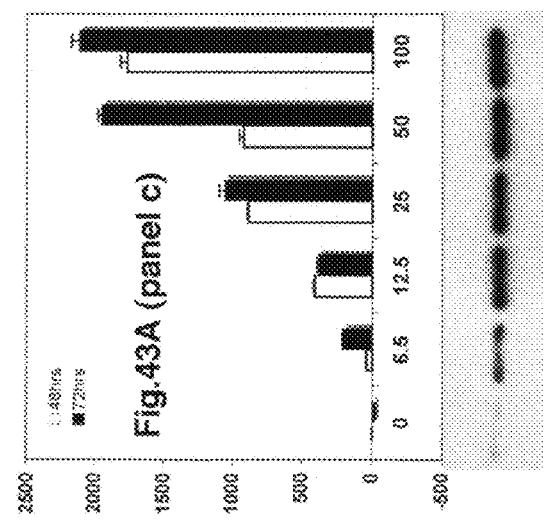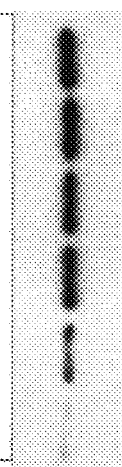
Fig.43A (panel d)

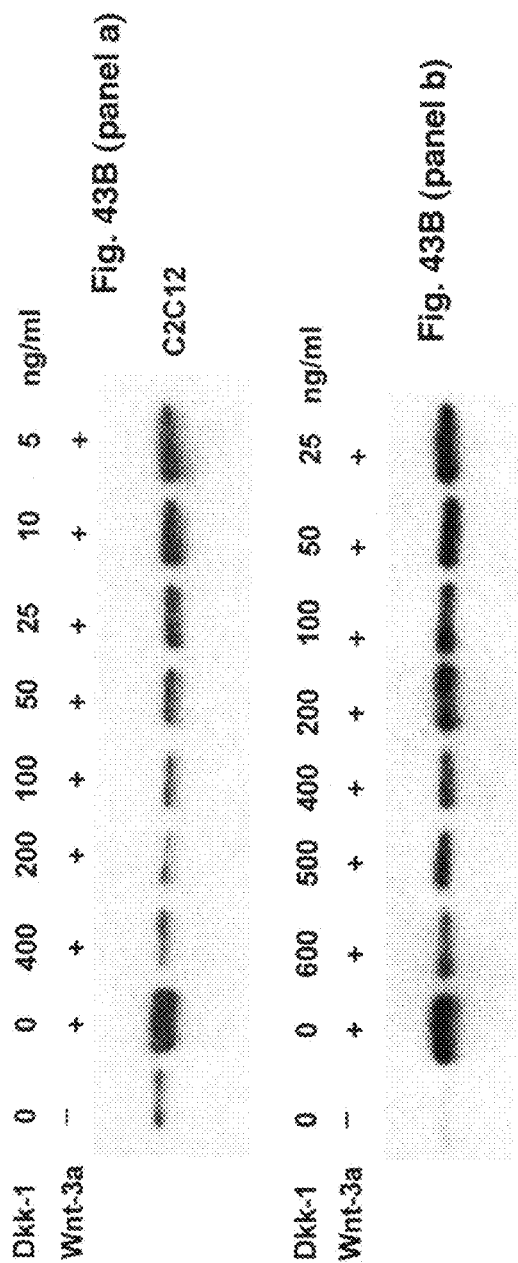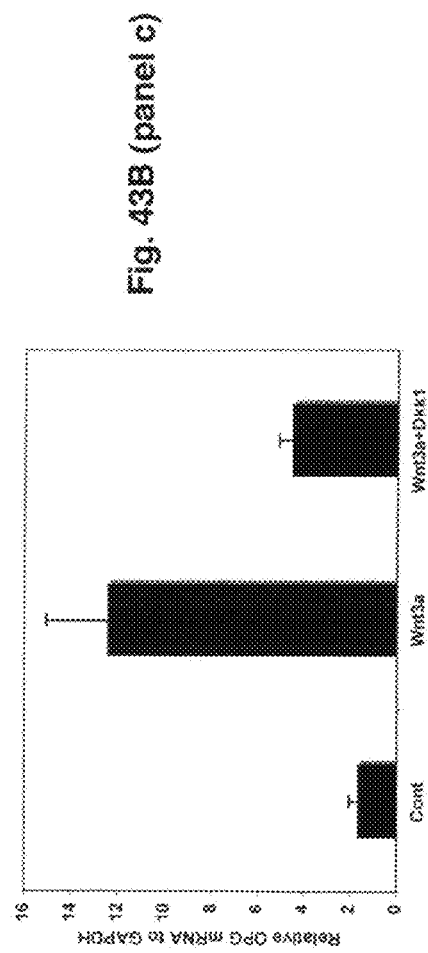

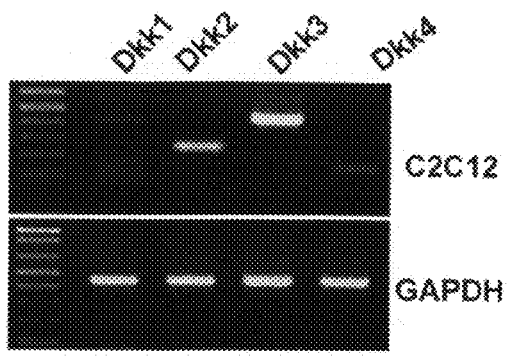
Fig. 43C (panel a)
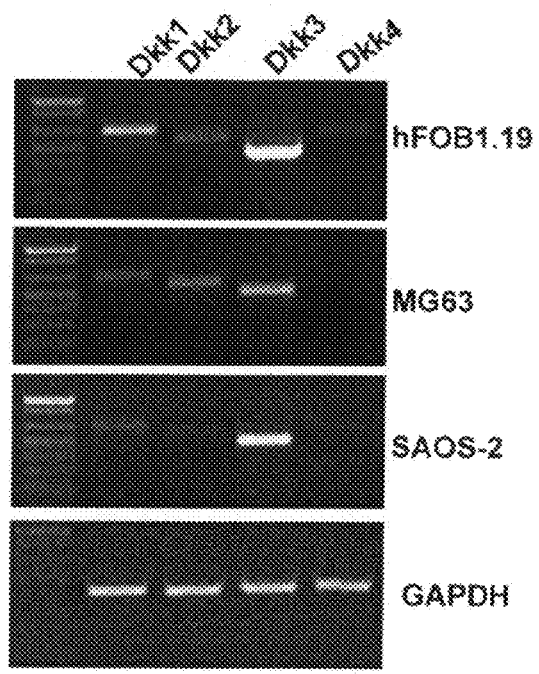
Fig. 43C (panel b)
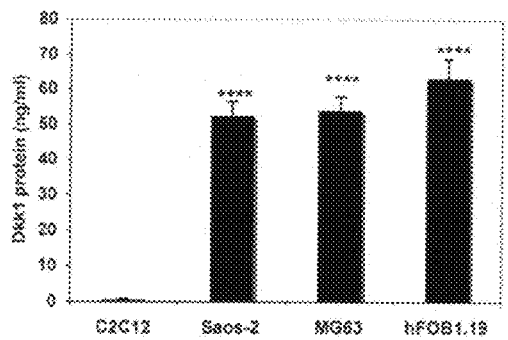
Fig. 43C (panel c)
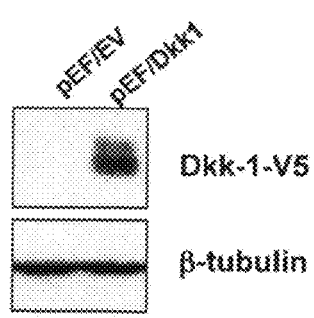
Fig. 43C (panel d)
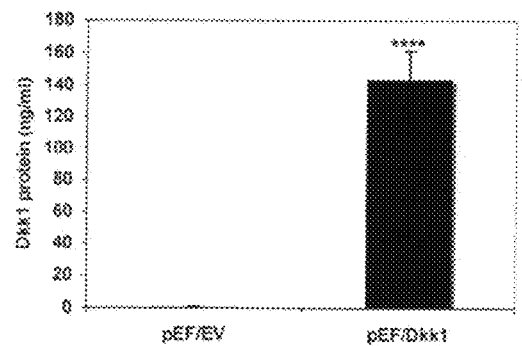
Fig. 43C (panel e)

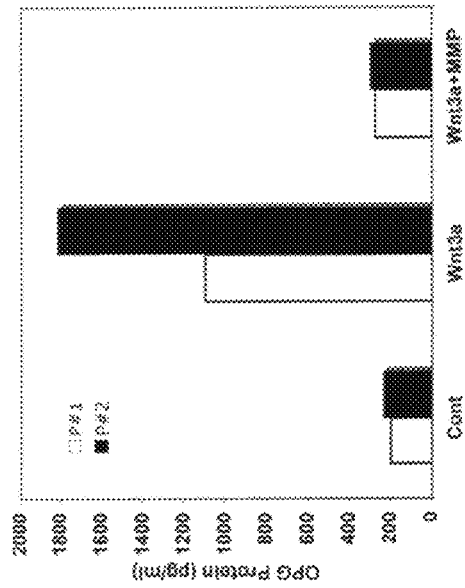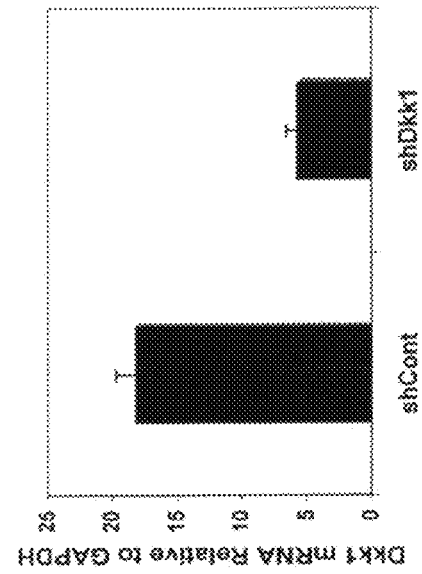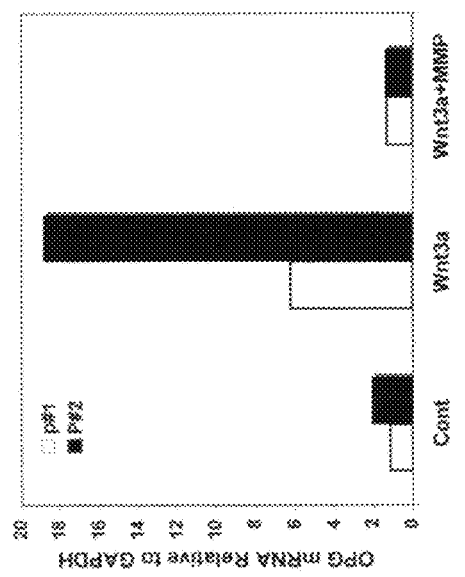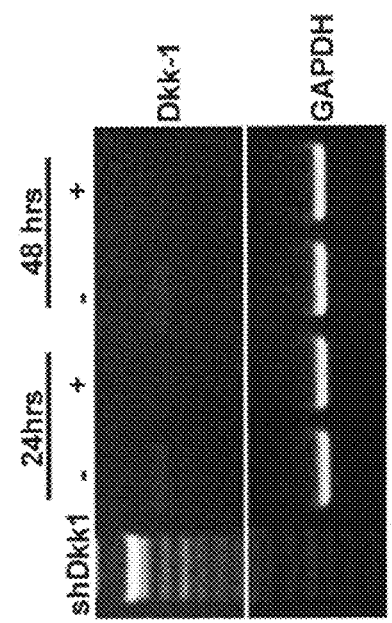

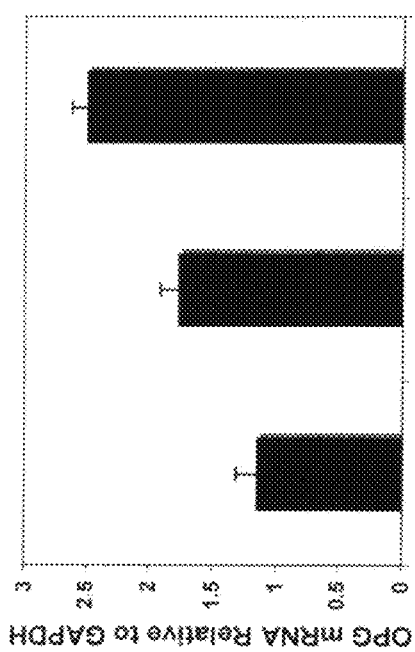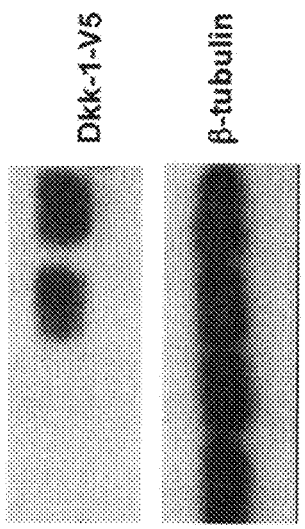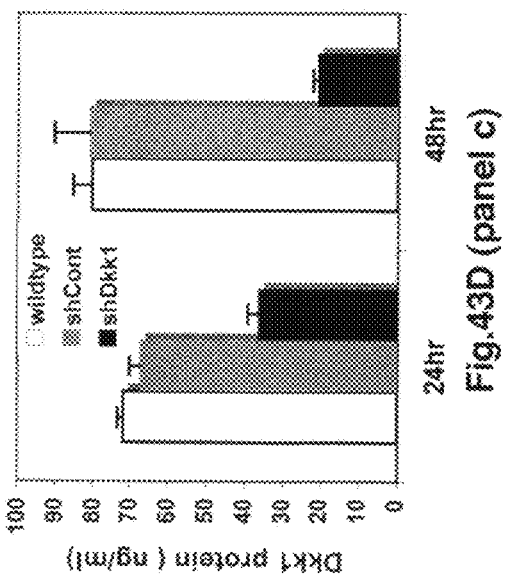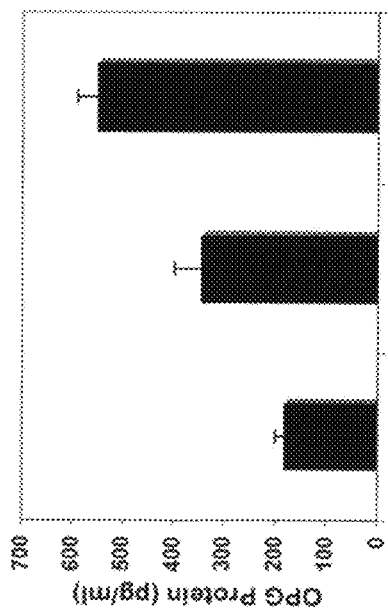

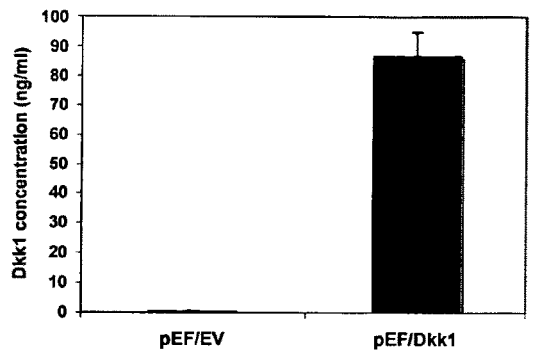
Fig. 43E (panel b)
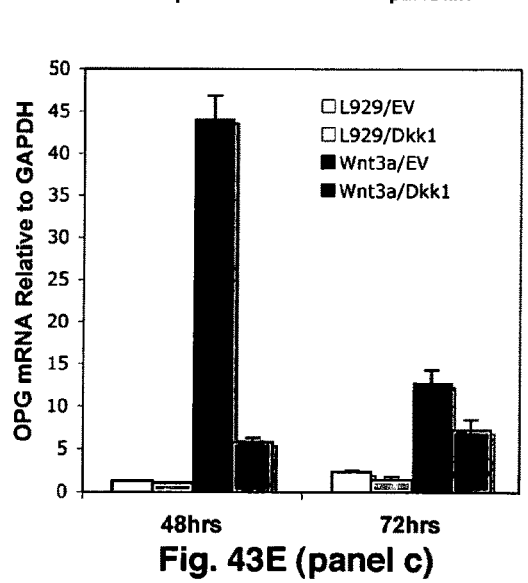
Fig. 43E (panel c)
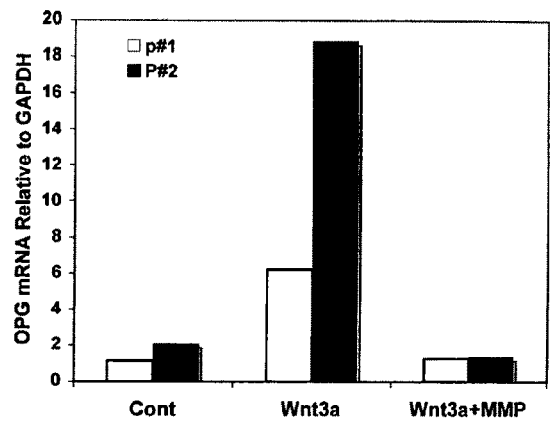
Fig. 43E (panel e)
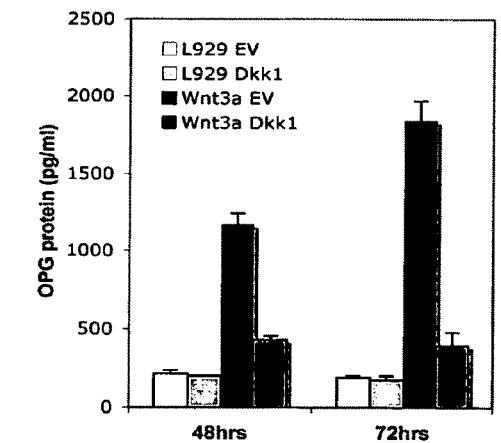
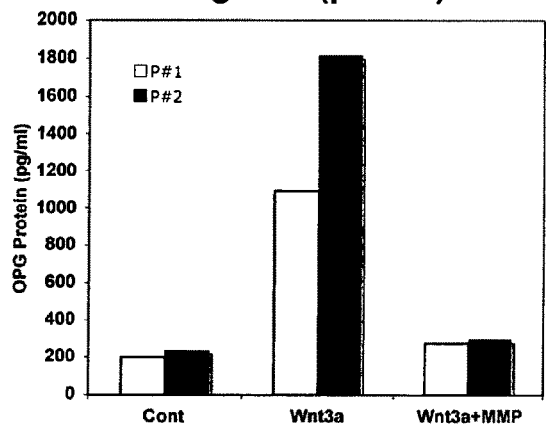
Fig. 43E (panel f)
Fig. 43E (panel d)

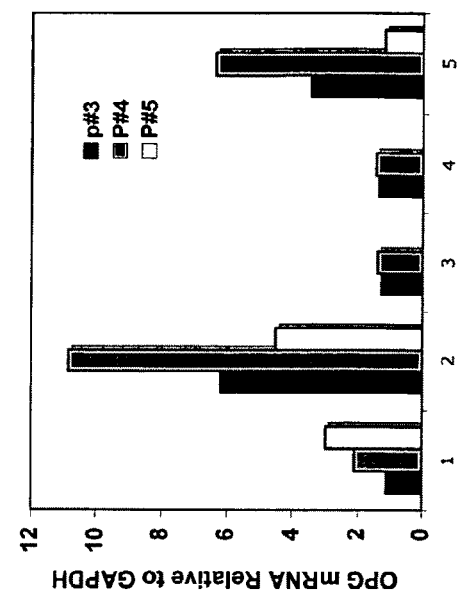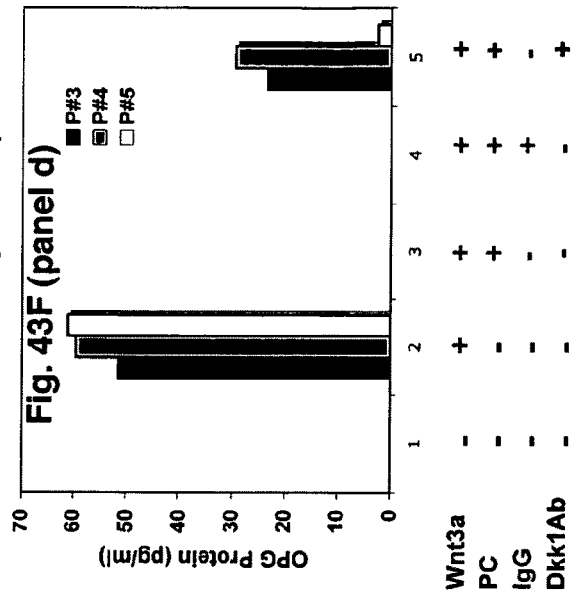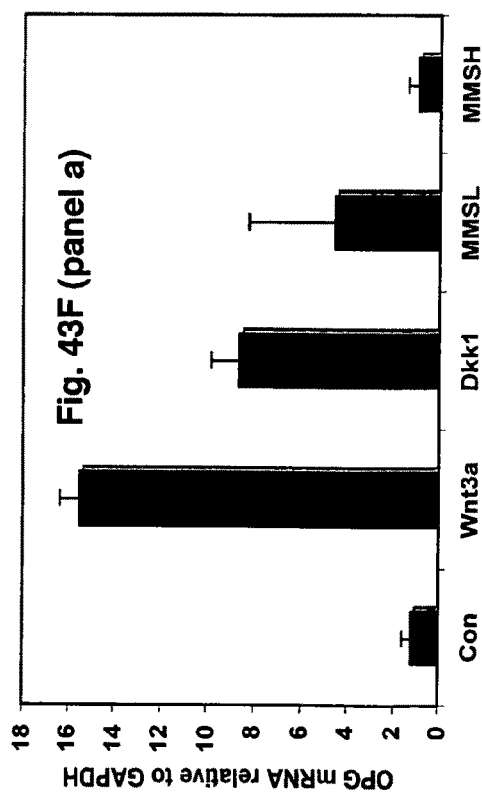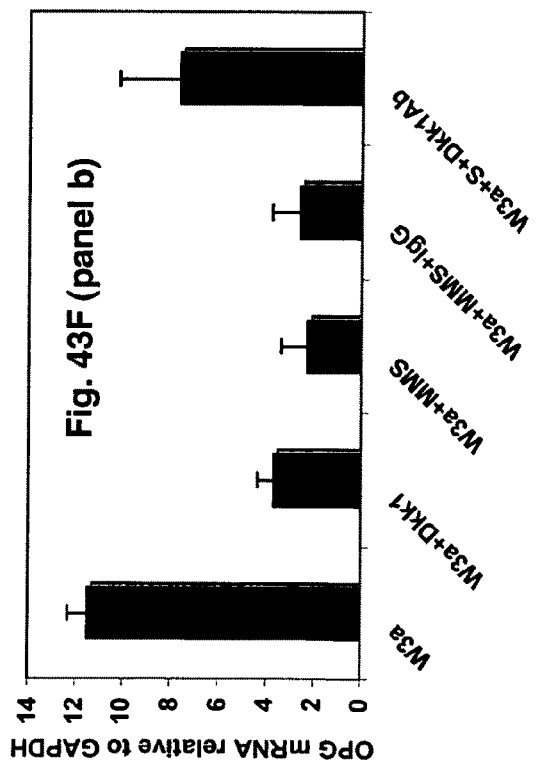
Fig. 43F (panel a)
Fig. 43F (panel b)
Fig. 43F (panel c)
Fig. 43F (panel d)

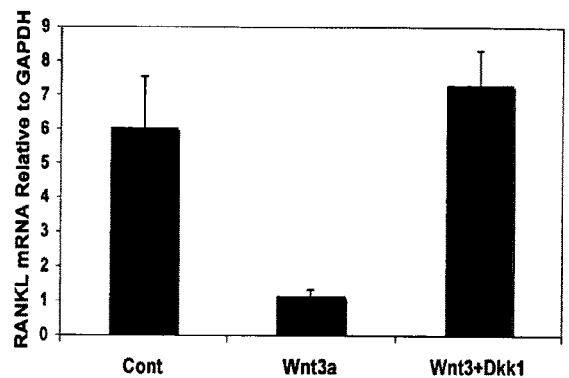
Fig. 43G (panel a)
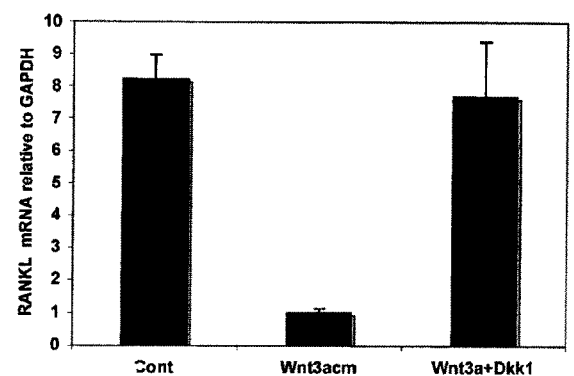
Fig. 43G (panel b)
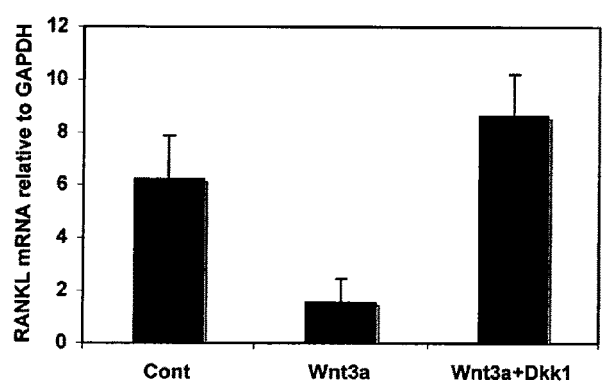
Fig. 43G (panel c)

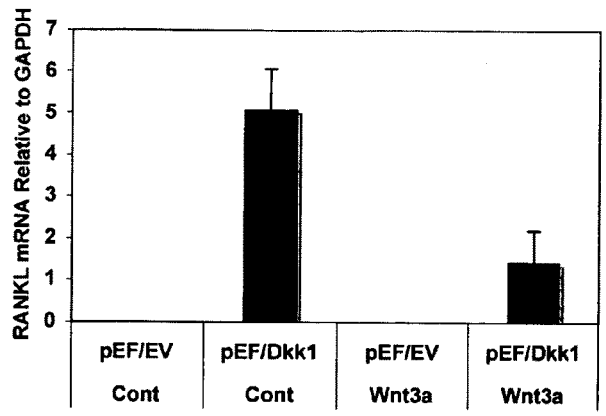
Fig. 43G (panel d)
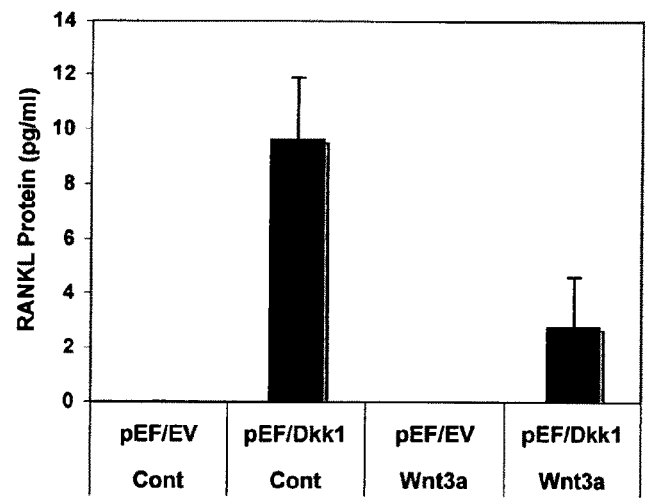
Fig. 43G (panel e)
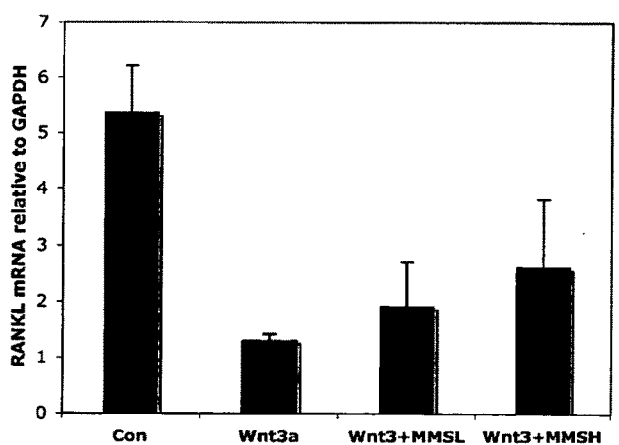
Fig. 43G (panel f)

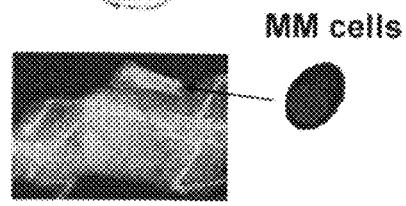
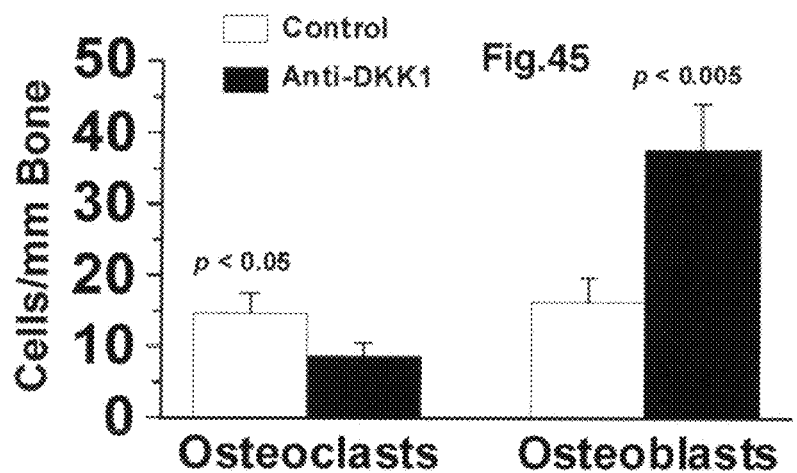
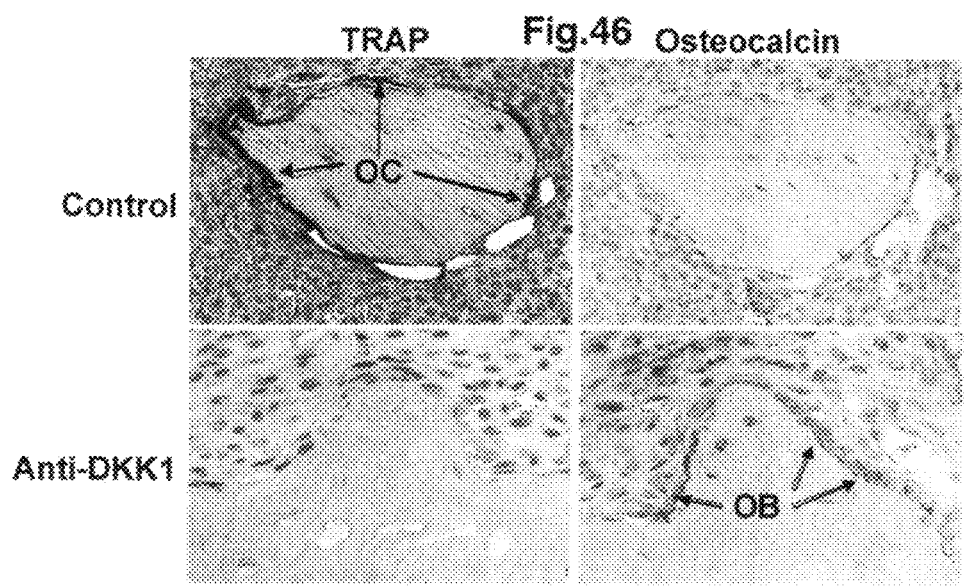

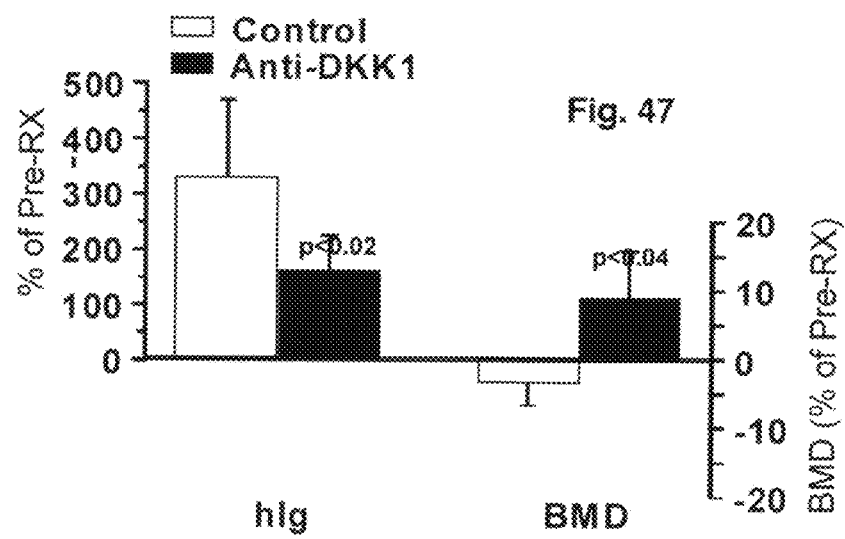
Fig. 47
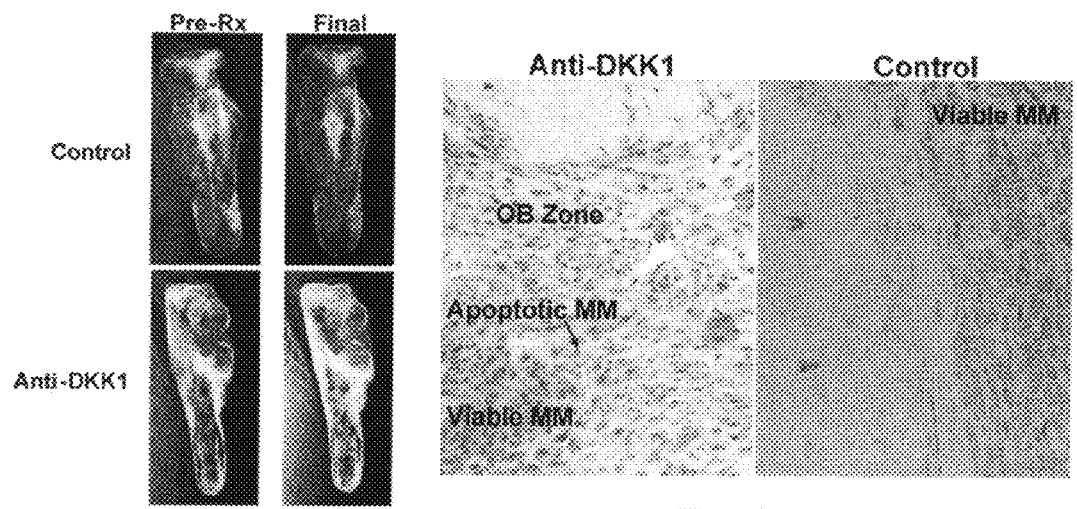
Fig. 48
Fig. 49

METHODS OF CONTROLLING BONE LOSS BY INHIBITING DKK1

CROSS-REFERENCE TO RELATED APPLICATION

This is a continuation-in-part of application U.S. Ser. No. 11/176,739, filed Jul. 7, 2005, now U.S. Pat. No. 7,642,238 which is a continuation-in-part of application U.S. Ser. No. 10/727,461, filed Dec. 4, 2003, now US Pat. No. 7,459,437 which claims benefit of provisional patent application U.S. Ser. No. 60/431,040, filed Dec. 5, 2002.

FEDERAL FUNDING LEGEND

This invention was created, in part, using funds from the federal government under National Cancer Institute grants CA93897, CA55819 and CA97513. Consequently, the U.S. government has certain rights in this invention.

BACKGROUND OF THE INVENTION

1. Field of the Invention

The present invention relates generally to the study of multiple myeloma. More specifically, the present invention relates to the identification and validation of molecular determinants of myeloma bone disease through comparative global gene expression profiling and employment of the SCID-rab mouse model for primary myeloma. Further, this invention relates to methods of treatment of bone disease by stimulating bone formation and reducing bone loss via targeting molecular determinants identified by the global gene expression profiling.

2. Description of the Related Art

Multiple myeloma (MM) is a rare, yet incurable malignancy of terminally differentiated plasma cells (PC) that affects approximately 15,000 persons per year in the United States, and represents the second most common hematopoietic malignancy. Multiple myeloma represents 13% of all lymphoid malignancies in the white population and 31% of lymphoid malignancies in the black population. The malignant plasma cells home to and expand in the bone marrow causing anemia and immunosuppression due to loss of normal hematopoiesis.

Multiple myeloma is also associated with systemic osteoporosis and local bone destruction leading to debilitating bone pain and susceptibility to fractures, spinal cord compression and hypercalcemia. Myeloma is the only hematological malignancy consistently associated with lytic bone disease and local bone destruction is limited to areas adjacent to plasma cells, suggesting that the malignant plasma cells secrete factors that enhance osteoclast function and/or osteoblast anergy. The prevalence of bone disease varies with the presentation of myeloma, from smoldering myeloma, often without bone involvement, to solitary plasmacytoma, to diffused or focal multiple myeloma where systemic losses of bone mineral density or focal lytic bone lesions are seen in approximately 80% of patients.

In recent years, it has become evident that lytic bone disease is not only a consequence of myeloma, but that it is intricately involved in promoting disease progression. Change in bone turnover rates predicts clinical progression from monoclonal gammopathy of undetermined significance (MGUS) to overt myeloma by up to 3 years. While initially osteoclast and osteoblast activity are coupled, the coupling is lost with disease progression. Osteoclast activity remains increased and osteoblast activity is diminished, with lytic bone disease as the consequence. Studies in the 5T2 murine myeloma and the SCID-hu model for primary human myeloma demonstrated that inhibition of osteoclast activity is associated with inhibition of myeloma growth and reduction of myeloma tumor burden. These studies support reports that inhibition of bone resorption with bisphosphonates had an anti-myeloma effect.

Whereas the biology of osteoclasts in myeloma-associated lytic bone disease has been investigated intensively, little is known about the disease-associated changes in osteoblast activity and their underlying mechanisms. It has been suggested that in myeloma, the ability of mesenchymal stem cells to differentiate into the osteogenic lineage is impaired. However, the mechanisms responsible for such impairment have not been elucidated.

The Wnt signaling pathway is involved in both normal skeletogenesis and cancer related bone disease. The first link between Wnt signaling and human bone disease came from observations that inactivating mutations in the Wnt co-receptor, LRP5, causes the osteoporosis-pseudoglioma syndrome (OPPG) (Gong et al., 2001). The canonical Wnt signaling pathway is regulated by large number of antagonists, including the DKK family and secreted frizzled-related protein (SRFPs). To date, four Dkk proteins have been identified in mammals (Kawano and Kyota, 2003), among which Dkk1 and Dkk2 have been well characterized. Subsequently it was shown that mutations in LRP5 that causes a high bone mass phenotype were distinct from those seen in osteoporosis-pseudoglioma syndrome and prevented binding of Dickkopf-1 (DKK1), a soluble inhibitor of Wnt and high affinity ligand for LRP5 (Boyden et al., 2002; Little et al., 2002). DKK1, antagonizing the canonical Wnt pathway by binding to LRP5/6 and Kremen (Bafico et al., 2001; Mao et al., 2002; Mao et al., 2001), blocks maturation of osteoblasts and formation of mineralized matrix (Baron and Rawadi, 2007; van der Horst et al., 2005).

Additionally, over-expression of DKK1 in transgenic mice leads to decreased bone mass (Baron and Rawadi, 2007), while deletion of a single allele of DKK1 in mouse osteoblasts results in increased bone formation and bone mass (Morvan et al., 2006). The osteolytic prostate cancer line PC-3, when transfected with shRNA targeting DKK1, reverted to an osteoblastic phenotype. In addition, transfection of DKK1 into the osteoblastic prostate cancer cell line C4-2B, which normally induces a mix of osteoblastic and osteolytic lesions, caused the cells to develop osteolytic tumors in SCID mice. Thus, the role of DKK1 in promoting bone lesion development appears not to be limited to MM, but has also been indicated in prostate cancer.

In addition to inhibiting osteoblastogenesis, elevated DKK1 levels may enhance osteoclastogenesis. Thus, bone destruction, a cardinal feature of multiple myeloma (MM) may result from uncoupling of osteoclast and osteoblast activities (Bataille et al., 1991; Roodman, 2004; Taube et al., 1992). Osteoclasts are activated by binding of receptor activator of nuclear factor kappa B ligand (RANKL) (Anderson et al., 1997; Kong et al., 1999; Lacey et al., 1998) to its cognate receptor, RANK, while osteoprotegerin (OPG) (Simonet et al., 1997) (a soluble member of the tumor necrosis receptor super-family) acts as a naturally occurring decoy receptor that competes with RANK for binding of RANKL (Suda et al., 1999). MM cells likely stimulate expression of RANKL and suppress expression of OPG by osteoblasts or their progenitors (Giuliani et al., 2001; Pearse et al., 2001). Increased serum levels of RANKL and decreased levels of OPG have been associated with a poor prognosis in MM (Terpos et al., 2003). Restoring the RANKL/OPG imbalance by RANKL antagonist or recombinant OPG not only reduce MM-associated bone lesions but also halt disease progression in animal models (Pearse et al., 2001; Vanderkerken et al., 2003; Yaccoby et al., 2002; Oyajobi et al., 2001).

Mechanistically, regulation of osteoclastogenesis by osteoblast-derived OPG (Glass et al., 2005; Holmen et al., 2005; Jackson et al., 2005) and RANKL (Holmen et al., 2005; Galli et al., 2006; Spencer et al., 2006) involves Wnt signaling, a pathway that is regulated by a large number of antagonists, including members of the Dickkopf family (Morvan et al., 2006), the family of secreted frizzled-related protein (sR-FPs) (Finch et al., 1997; Kawano and Kypta., 2003), and sclerostin (Semenov et al., 2005). Osteolytic bone lesion (OBL) in MM cells could be linked to DKK1 secretion by tumor cells (Tian et al., 2003; Giuliani et al., 2007; Haaber et al., 2007; Politou et al., 2006), inhibiting canonical Wnt in and differentiation of osteoblasts. Blocking DKK1 with a neutralizing antibody prevented MM-induced bone resorption in the SCID-rab model (Yaccoby et al., 2007). Although each appear to play an role in OBL, whether DKK1 might influence RANKL/OPG expression in myeloma has never been established.

The prior art is deficient in methods to diagnose and treat multiple myeloma bone diseases. Furthermore, the prior art is also deficient in understanding the disease-associated changes in osteoblast activity and the underlying mechanisms in multiple myeloma associated lytic bone diseases. The present invention fulfills this longstanding need and desire in the art.

SUMMARY OF THE INVENTION

The present invention is directed to a method of controlling bone loss in an individual. This method comprises the step of inhibiting a Wnt signaling antagonist at the nucleic acid or protein level. The present invention is also directed to a method of treating bone disease in an individual, comprising the step of administering to the individual a pharmacologically effective amount of an inhibitor of a Wnt signaling antagonist. Such a step results in blocking of induction of Wnt ligand, restoring the RANKL/OPG levels or both.

The present invention is also directed to a method of inhibiting tumor growth in bone of an individual. Such a method comprises the step of blocking the activity of DKK1.

The present invention is also directed to a method of screening for a compound that controls bone loss and inhibits human myeloma growth. Such a method comprises engrafting human myeloma cells in a rabbit bone implanted in a SCID-rab mouse. This is followed by administration of a candidate compound to the mouse. Subsequently, bone mineral density of the implanted bone and level of serum human monoclonal immunoglobulin in the mouse is compared with a control mouse that has not received the compound. An increase in the bone mineral density and a decrease in the level of the serum immunoglobulin in the treated mouse compared to the control mouse indicates that the compound controls bone loss and inhibits human myeloma growth. The present invention is further directed to a method of inhibiting multiple myeloma growth. Such a method comprises blocking of the DKK1 activity.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

So that the matter in which the above-recited features, advantages and objects of the invention as well as others which will become clear are attained and can be understood in detail, more particular descriptions and certain embodiments of the invention briefly summarized above are illustrated in the appended drawings. These drawings form a part of the specification. It is to be noted, however, that the appended drawings illustrate preferred embodiments of the invention and therefore are not to be considered limiting in their scope.

FIGS. 1A and 1B show global gene expression patterns reflecting bone lesions in myeloma. FIG. 1A shows cluster-view of normalized expression levels of 57 genes identified by logistic regression analysis as being significantly differentially expressed in malignant plasma cells from patients with no (n=36) and 1+MRI focal lesions (n=137) (P<0.0001). The 28 genes exhibiting elevated expression in plasma cells from patients with 1+MRI lesions are ordered from top to bottom based on rank of significance. Likewise the 30 genes showing significant elevation in patients with no MRI-lesions are ordered from bottom to top based on significance rank. Gene symbols (Affymetrix probe set identifiers when the gene is unnamed) are listed to the left. Normalized expression scales range from −30 (blue) to +30 (red) as indicated below the data display. The four genes remaining significant after permutation adjustment are underlined. FIG. 1B shows a bar graph of DKK1 gene expression in plasma cells from normal bone marrow (BPC), patients with monoclonal gammopathy of undetermined significance (MGUS), Waldenström's macroglobulinemia (WM), and multiple myeloma (MM) presented on the x-axis. MM samples are broken down into three bone lesion groups: no MRI/no x-ray lesions, 1+MRI/no x-ray lesions, and 1+MRI/1+x-ray lesions. The Affymetrix Signal, a quantitative measure of gene expression derived from MAS 5.01, is indicated on the y-axis. DKK1 gene expression level in each sample is indicated by a bar, with the height of the bar proportional to gene expression intensity. Samples are ordered from the lowest to highest DKK1 gene expression from left to right on the x-axis. The number of samples in each group is indicated below each group designator. Statistics for comparisons between the MM subgroups are indicated in the text.

FIG. 5 shows MIP-1a and CCR1 were "spike" genes in multiple myeloma, but they were not correlated with lytic lesions. Black bar: CCR1; gray bar: MIP-1a.

FIG. 13 shows FRZB was elevated in monoclonal gammopathy of undetermined significance (MGUS), and had higher expression in smoldering multiple myeloma (SMM) and newly diagnosed multiple myeloma (MM).

FIG. 14 shows the expression of DKK-1 and FRZB in monoclonal gammopathy of undetermined significance (MGUS) and smoldering multiple myeloma (SMM).

FIG. 16 shows the expression of DKK-1 and FRZB tend to be higher in plasma cells from medullary PCT than those from iliac crest. PCT, FNA.

FIGS. 40A and 40B show DKK1 protein in the bone marrow plasma is highly correlated with DKK1 gene expression and the presence of bone lesions. FIG. 40A shows the expression of DKK1 mRNA was detected by microarray and DKK1 protein by ELISA in a total of 107 cases of newly diagnosed myeloma. Results of both assays were transformed by the log base 2 and normalized to give a mean of 0 and variance of 1. Each bar indicates the relative relationship of gene expression and protein expression in each sample. There was a significant correlation between DKK1 mRNA in myeloma plasma cells and protein in bone marrow plasma (r=0.65, P<0.001). FIG. 40B shows bar view of DKK1 protein levels in bone marrow plasma cells from normal donors (BPC), patients with monoclonal gammopathy of undetermined significance (MGUS), Waldenstrom's macroglobulinemia (WM), and multiple myeloma (MM) are presented on the x-axis. MM samples are broken down into three bone lesion groups: no MRI/no x-ray lesions, I+MRI/no x-ray lesions, and 1+MRI/1+x-ray lesions. The DKK1 protein concentration (ng/ml) is indicated on the y-axis. To enable comparisons of DKK1 protein levels in the lower ranges, 200 ng/ml was made the maximum value. This resulted in the truncation of a single sample with DKK1 concentration of 476 ng/ml. DKK1 protein level in each sample is indicated by a bar, with the height of the bar proportional to DKK1 protein levels. Samples are ordered from the lowest to highest DKK1 protein levels from left to right on the x-axis. The number of samples in each group is indicated below each group.

FIGS. 41A and 41B show recombinant DKK1 and MM plasma can block alkaline phosphatase production in BMP-2 treated C2C12 cells in a DKK1-dependent manner. FIG. 41A shows alkaline phosphatase levels, a marker of osteoblast differentiation (y-axis) were measured in C2C12 cells after 5 days of culture in the presence of 5 percent fetal calf serum alone or with BMP2, BMP2+DKK1, BMP2+DKK1+anti-DKK1, or BMP-2+DKK1+ polyclonal IgG. Each bar represents the mean (±SEM) of triplicate experiments. Note that activity of alkaline phosphatase increased in the presence of BMP-2 and significant reduction of this protein by co-incubation with recombinant DKK1. Also note that anti-DKK1 antibody, but not polyclonal IgG can block the repressive activity of DKK1. FIG. 41B shows alkaline phosphatase levels (y-axis) were tested in C2C12 cells after culturing these cells for 5 days in 5 percent fetal calf serum alone or 50 ng/ml BMP-2+10 percent normal bone marrow plasma (NS) or BMP-2+10 percent myeloma bone marrow plasma from 10 patients with newly diagnosed myeloma (sample identified provided), or BMP2+10 percent myeloma patient plasma+anti-DKK1 or goat polyclonal IgG. Each bar represents the mean (±SEM) of triplicate experiments. DKK1 concentration from each bone marrow plasma samples was determined by ELISA and final concentrations in culture after 1:10 dilution are indicated on the x-axis. Note that samples with >12 ng/ml DKK1 had an effect on alkaline phosphatase production. A star indicates P<0.05 in comparison to alkaline phosphatase in BMP2+10 percent normal human bone marrow plasma.

FIGS. 42A-42I show that DKK1 blocks the osteoblast differentiation by blocking an endogenous Wnt signal being made by the osteoblast precursor. FIG. 42A shows that Frizzled (Fz) and LRP5/6 mRNAs are expressed in osteoblast cells. Total RNA was extracted from indicated cell lines. RT-PCR was performed with mouse (FIG. 42A (panel a) and human (FIG. 42A (panel b) primers specific for Fz1 through 10 and LRP5/6 (mouse, FIG. 42A (panel c); human, (FIG. 42A (panel d)), respectively. GAPDH was included as control. FIG. 42B shows that canonical Wnt signaling is functional in osteoblast (OB) cells. OB cells were treated with Wnt3a CM or control CM for indicated time and cell lysate harvested. Lysate protein was subjected to GST-E-cadherin assay and Immunoblotting analysis using anti-_-catenin antibody (FIG. 42B (panel a) and anti-non-phosphorylated form (FIG. 42B (panel b)). RT-PCR was performed using specific primers for indicated mouse (FIG. 42B (panel c)) and human (FIG. 42B (panel d)) genes in indicated cell lines. C2C12 cells transfected using wild type (TOPflash) or mutant (FOPflash) LEF/TCF reporter luciferase constructs and pSV-b-galactosidase vector (transfection efficiency internal control) (FIG. 42B (panel e)) were treated with Wnt3a CM or control CM prior to determination of luciferase activity. Results are shown as mean ±SD (n=3) and are representative of three independent experiments. **P<0.01 versus control.

FIG. 42C shows that Dkk-1 and MM patient sera inhibit Wnt3a induced accumulation of b-catenin in OB cells. In FIG. 42C (panel a), the indicated cells were treated with recombinant Dkk-1 at indicated concentrations and then stimulated with Wnt3a or control CM. proteins in cell lysate were subjected to GST-E-cadherin assay and Immunoblotting analysis using anti-non-phosphorylated b-catenin. In FIG. 42C (panel b), Dkk1 protein in cell lysate (upper panel) and CM (middle panel) from OPM-2 clones expressing PEF6/V5-His-TOPO-Dkk-1 (Dkk1) or vector (EV) was confirmed by Immunoblotting blotting with anti-V5 antibody. In FIG. 42C (panel c), C2C12 cells were incubated with Dkk1 or EV CM from OPM-2 transfected cells then treated with Wnt3a or control CM. proteins in lysates were analyzed as in FIG. 42B using indicated antibody. In FIG. 42C (panel d) C2C12 cells were incubated with sera from MM patients containing low (L1) or high (H1-4) concentrations of Dkk1 protein. Cells were then treated with Wnt3a or control CM and lysates prepared and analyzed as in FIG. 42C (panel c).

FIG. 42D shows that Dkk1 inhibits BMP-2 induced alkaline phosphatase activity. C2C12 (FIG. 42D (panel a)), Saos-2 (FIG. 42D (panel b)), and hFOB1.19 (FIG. 42D (panel c)) cells were cultured for 72 hrs in DMEM with 2% horse serum containing Wnt3a, BMP-2, or Dkk1 either alone or in the indicated combinations. Cells were lysed and ALP activity measured and normalized to protein concentration. Data represent the mean ±SD (n=3). *p<0.05, P<0.01, *P<0.001. ***<0.00001 versus control or BMP-2 versus BMP-2 plus DKK1. FIG. 42E shows that blocking the canonical b-catenin pathway inhibits TCF/LEF mediated transcription and BMP-2 induced alkaline phosphatase activity. In FIG. 42E (panel a), C2C12 cells were transfected with dominant negative b-catenin (DN-b-Cat) or control (pcDNA4his) constructs and the expressions were confirmed by the indicated antibody by Immunoblotting analysis. In FIG. 42E (panel b), the positive clones were co-transfected with wild type (TOPflash) or mutant (FOPflash) LEF/TCF reporter luciferase constructs. After transfection, the cells were treated and subjected to luciferase assay as in FIG. 2 E. C2C12 pcDNAhis or DN-b-Cat clone #4 (FIG. 42E (panel c)) and #5 (FIG. 42E (panel d)) cells were cultured in DMEM containing 2% horse serum or 100 ng/ml of BMP-2 for 72 hrs after which ALP activity was measured. In FIG. 42E (panel e), C2C12 cells were transfected with empty vector or Dkk1- and Dkk2-expressing vectors and the expression of the proteins were determined as in FIG. 42C (panel b). The positive clones and control vector were treated with BMP-2 and subjected to ALP activity assay as in FIG. 42E (panel d). Results are shown as mean ±SD (n=3) and are representative of three independent experiments (FIG. 42E (panel f)). P<0.01 and ***p<0.001 versus control. FIG. 42F shows that silencing LRP5/6 mRNA blocks BMP-2 induced alkaline phosphatase activity. C2C12 cells were transiently transfected with 1.0 mg/ml (FIG. 42F (panel a) or serial concentration of siRNA specific for LRP5 (FIG. 42F (panel b)) or LRP6 (FIG. 42F (panel c)). Forty eight hrs after transfection RNA was isolated and subjected to RT-PCR (FIG. 42F (panel a) or qPCR (FIG. 42F (panels b and c). In FIG. 42F (panel d), the cells transfected with 0.25 or 0.5 mg/ml of siRNA specific for LRP5 or LRP6 were cultured in medium containing 100 ng/ml of BMP-2 in DMEM. Cells were lysed after 72 hrs and alkaline phosphatase activity determined. Data represent the mean ±SD (n=3) of representative experiments. *p<0.05, p<0.01, *p<0.001 versus control.

FIG. 42G shows that Wnt3a mediated increase in b-catenin is independent of BMP-2. In FIG. 42G (panel a), C2C12, hFOB1.19, MG63, and Saos-2 cells were treated with Wnt3a CM, control CM or 100 ng/ml of BMP2. Lysate protein was subjected to GST-E-cadherin assay and Immunoblotting analysis by anti-b-catenin antibody as described in Materials and Methods. In FIG. 42G (panel b), 50 mg aliquots of protein from cell lysates were resolved on 8% SDS-PAGE and analyzed with the indicated antibodies. In FIG. 42H, C2C12 cells were transfected with wild type (TOPflash) LEF/TCF reporter luciferase constructs. After transfection, the cells were treated with 100 ng/ml of Wnt3a, BMP2 (100 ng/ml) or combined with Wnt3a and BMP2 or with Dkk1 (100 ng/ml) for 24 hours and then subjected to luciferase assay. Results are shown as mean ±SD (n=3) and representative of three independent experiments. P<0.01 versus control. In FIG. 42I, C2C12 cells were treated with 100 ng/ml of Wnt3a, BMP2 (100 ng/ml) or combined BMP2 with Dkk1 at indicated time. Results are shown as mean ±SD (n=3) and representative of three independent experiments. P<0.01 and ****P<0.0001 versus control.

FIGS. 43A-43G show that myeloma-derived DKK-1 disrupts Wnt-regulated osteoprotegerin and RANKL production by osteoblasts. FIG. 43A shows that Wnt3a induced increase in OPG mRNA and protein in osteoblast progenitor cells. C2C12 cells (panel a and panel c) and Saos-2 cells (panel b and panel d) were treated with serial concentrations of recombinant Wnt3a for indicated times. The OPG mRNA (panels a and b) was amplified by qPCR analysis. The supernatant of treated cells (panels c and d) was harvested and subjected to ELISA for measurement of OPG protein. Protein in lysate (1 mg) was subjected to the GSTE-cadherin assay. Following SDS-PAGE analysis, uncomplexed beta-catenin was detected by anti-beta-catenin antibody (panels c and d). The results are a mean ±SD (n=4). Results are representative of three independent experiments. *P<0.05 versus control.

FIG. 43B shows that DKK-1 inhibition of Wnt3a induced OPG mRNA and protein in osteoblast cells. C2C12 (panel a)

Figure 1B:
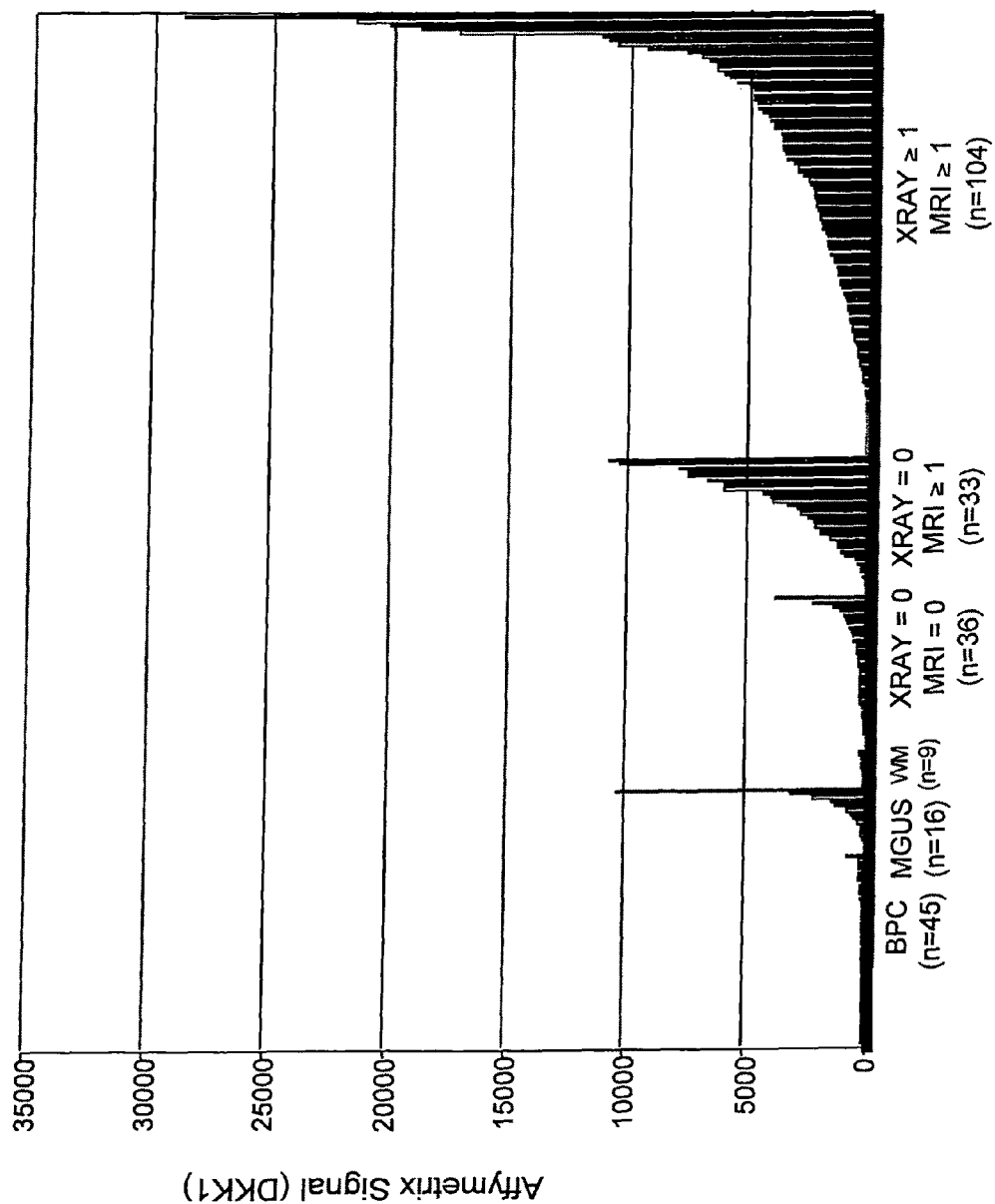

and Saos-2 (panel b) cells were stimulated with or without Wnt3a after prior treatment with recombinant DKK-1 with indicated concentrations and then lysed. 0.5 mg of protein from cell lysates was subjected to the GST-E-cadherin assay. Following SDS-PAGE, uncomplexed b-catenin was detected by anti-b-catenin antibody. Total RNA was isolated from treated C2C12 (panel c) and Saos-2 (panel d) cells and OPG mRNA quantified. The supernatant of C2C12 (panel e) and Saos-2 (panel f) cells treated, as above for 72 hours, was harvested and subjected to ELISA for measurement of OPG. The results are shown as mean SD (n=3). Results are representative of three independent experiments. $P<0.01$, *$P<0.001$, ****$p<0.00001$ versus control.

FIG. 43C shows that ectopic expression of DKK1 diminished Wnt3a induced OPG mRNA and protein in osteoblast cells. The expression of DKK family members in C2C12 (panel a) and human osteoblast cell lines (panel b) as determined by RT-PCR analysis are presented. Concentration of DKK1 protein in culture supernatant of indicated cell lines by ELISA analysis (panel c). C2C12 cells were stable transfected with an empty vector or DKK1-expressing vector. DKK1 protein expression was detected by the anti-V5 antibody (panel d) and the concentration of DKK1 protein is shown in panel e. The cells were treated with recombinant 100 ng/ml of rWnt3a. Relative OPG mRNA (panel f) and OPG protein concentration (panel g) was measured by qPCR or ELISA analysis as described in FIG. 43A. Data represent the mean ±SD (n=3) of representative experiments. *$P<0.05$, *$p<0.001$, and **$p<0.00001$ versus control.

FIG. 43D shows that knockdown of DKK1 by shRNA restored Wnt3a induced OPG in Osteoblast. C2C12 cells were transiently infected with supernatant containing control siRNA (shCont) or shRNA specific for DKK1 for indicated times. Total RNA was then isolated and subjected to RT-PCR for detecting DKK1 mRNA (panel a). cDNA from 24 hours was subject to qPCR to confirm DKK1 mRNA expression (panel b). Supernatants of the cells were harvested and subjected to ELISA for measuring DKK1 protein (panel c). The infected cells were treated with rWnt3a for 48 hours and RNA and supernatants were harvested and subjected to qPCR and ELISA analysis for OPG mRNA (panel d) and protein (panel e). Data represent the mean ±SD (n=3) of representative experiments. $P<0.01$, *$p<0.001$, versus control.

FIG. 43E shows that co-culturing osteoblast cells with DKK1 expressing MM cells inhibits Wnt3a-induced OPG. A MM cell line, OPM-2 was transfected with pEF6 vector (pEF/EV) or pEF6/DKK-1. DKK1 protein in pEF/EV or pEF/DKK1 was determined (panel a). The concentration of DKK1 protein in culture supernatants in pEF/EV and pEF/DKK1 was measured by ELISA (panel b). C2C12 cells were co-cultured with pEF/EV or pEF/DKK1 cells in presence rWnt3a or control for the indicted times. OPG synthesis in these cells, as measured by qPCR, is presented (panel c). Supernatants of the C2C12 were harvested and subjected to ELISA analysis to measure OPG protein concentration (panel d). The results are shown as mean ±SD (n=4). Results are representative of three independent experiments. $P<0.01$, *$P<0.001$, ****$p<0.00001$ versus control. C2C12 cells were cultured with primary CD1380-positive plasma cells from two MM pateins (P#1 and P#2) for 48 hours in the presence or absence of rWnt3a for 48 hours. The OPG mRNA in C2C12 cells was determined by qPCR (panel e). OPG protein in supernatant of the cultures was measured by ELISA (panel f).

FIG. 43F shows that neutralization of DKK1 rescues OPG expression in osteoblasts grown in the presence of MM sera or primary MM cells. C2C12 cells were treated with rWnt3a or vehicle after prior treatment with bone marrow sera from MM patients (n=8) containing low (L) (2.7 to 8.5 ng/ml) or high (H) (104.5 to 273.5 ng/ml) concentration of DKK 1 or recombinant DKK1 (100 ng/ml) as positive control for 48 hours (panel a). The cells were treated with rWnt3a or control vehicle after prior treatment with 25% sera from MM patients (n=21) containing mouse Ig or anti-DKK1 antibody for 48 hrs. C2C12 cells were co-cultured with CD138 positive plasma cells from MM in the presence or absence of Wnt3a, control IgG or anti-DKK1 antibody. OPG mRNA was determined by qPCR from the RNA, and OPG protein measured by ELISA of cell culture supernatants (panels a-d). $P<0.01$, *$P<0.001$, ****$p<0.00001$ versus control.

FIG. 43G shows that DKK1 and sera from MM pateints inhibits Wnt3a-induced suppression of RANKL in osteoblast. C2C12 (panel a), Saos-2 (panel b) and MG63 (panel c) cells were treated with Wnt3a-CM or Cont-CM after prior treatment with 100 ng/ml of DKK1 protein for 48 hours. RANKL mRNA was analyzed by qPCR. C2C12 cells transfected with empty vector (pEF/EV) or the vector carrying DKK1 cDNA (pEF/DKK1) were cultured in the presence of 100 ng/ml of BMP-2 and presence or absence of rWnt3a protein (100 ng/ml). The RNA and supernatant were harvested and subjected to (panel d) qPCR of RANKL mRNA (panel e) or ELISA for RANKL protein (panel e). C2C12 cells were treated with Wnt3a protein after prior incubation with sera from MM pateints (n=8) containing lower (<10 ng/ml) or higher concentration of DKK1 (>100 ng/ml) for 48 hours (panel f). RANKL mRNA was analyzed by qPCR. The results are shown as mean ±SD (n=3). *$P<0.01$, **$P<0.001$, versus control.

FIG. 44 shows the SCID-rab model for primary myeloma. A small piece of rabbit bone was implanted subcutaneously in SCID mice. Myeloma cells from different patients were injected directly into the implanted bone. Myeloma cells from more than 85% of patients were successfully engrafted in this model.

FIG. 45 shows that anti-DKK1 treatment is associated with an increased number of osteoblasts and a reduced number of osteoclasts in myelomatous bone of SCID-rab mice. Bone sections were stained for TRAP to identify osteoclasts and for osteocalcin to identify osteoblasts.

FIG. 46 shows that anti-DKK1 treatment increases osteoblast activity and reduces osteoclast numbers in myelomatous SCID-rab mice. Sequential sections were stained for TRAP and osteocalcin. Note that whereas control bone had increased osteoclast numbers and diminished osteoblasts, anti-DKK1 treatment resulted in increased osteoblast numbers and reduced those of the osteoclasts.

FIG. 47 shows that anti-DKK1 increases bone marrow density (BMD) and inhibits myeloma growth in myeloma-bearing SCID-rab mice. Myelomatous rabbit bone marrow density and circulating human immunoglobulins (hIg) were measured before treatment and at the end of the experiment.

FIG. 48 shows that blocking DKK1 increases bone mass in myelomatous SCID-rab mice. X-ray radiographs of the implanted rabbit bone of control and anti-DKK1-treated mice, before initiation of treatment (Pre-Rx) and at the end of the experiment (final) are shown. Many lytic lesions were evident in both mice at Pre-Rx. However, although the bone loss continued to increase in the control mouse, anti-DKK1 treatment resulted in increased bone mass and partial repair of lytic lesions.

FIG. 49 shows that increased osteoblast activity is associated with reduced tumor burden in SCID-rab mice treated with anti-DKK1. Myelomatous bone section from control and anti-DKK1-treated mice were immunohistochemically stained for osteocalcin. The bone treated with anti-DKK1 but not the control antibody was associated with remarkable increase in osteoblast (OB) number (stained brown). This area designated as OB zone was depleted of viable myeloma cells.

Figure 50A:
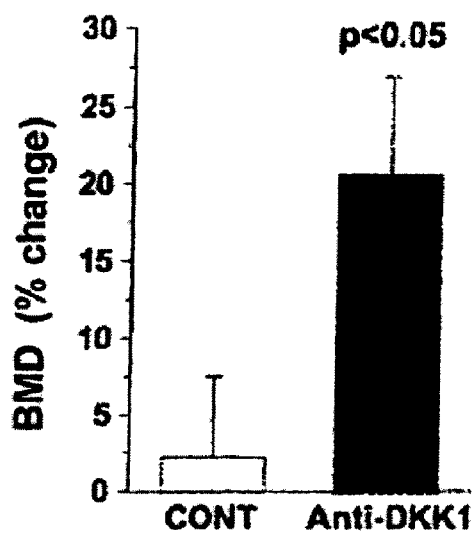
Figure 50B:
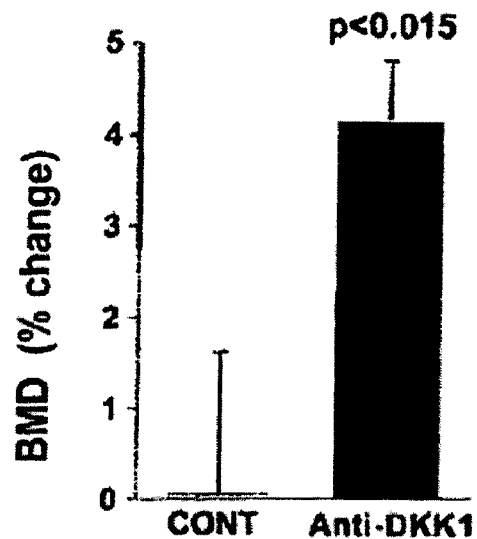
Figure 50C:
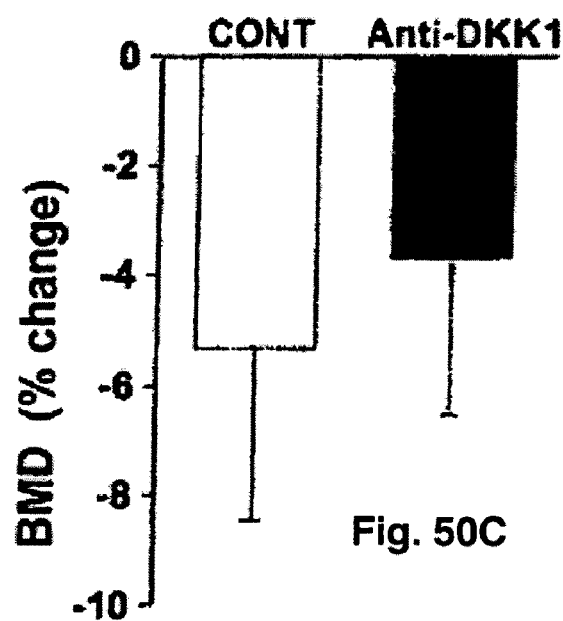

FIGS. 50A-50C show that DKK1 neutralizing antibody promotes bone formation in nonmyelomatous bones. FIGS. 50A-50B demonstrates changes in bone marrow density of the implanted bones (FIG. 50A) and mouse femur (FIG. 50B) in mice treated with control IgG and anti-DKK1 neutralizing antibody. FIG. 50C shows changes in bone marrow density of the uninvolved mouse femur in myelomatous hosts treated with the control IgG and anti-DKK1 neutralizing antibody.

DETAILED DESCRIPTION OF THE INVENTION

The present invention demonstrates that the secreted WNT signaling antagonists DKK-1 and FRZB mediate bone destruction seen in multiple myeloma. These data strongly implicate these factors in causing osteoblast anergy and contributing to multiple myeloma bone disease by suppressing the normal compensatory bone production that follows bone loss.

The role of multiple myeloma plasma cells in stimulating osteoclast activity has been intensely investigated and several key links established. Data presented herein provide for the first time evidence of a possible mechanistic explanation of osteoblast dysfunction in multiple myeloma. These are significant observations in that inhibition of WNT signaling causes defects in osteoblast function. The secreted DKK-1 and FRZB could account for both the systemic osteoporosis seen in multiple myeloma as well as the exaggerated local bone destruction proximal to plasma cells foci.

Importantly, DKK-1 and FRZB act to inhibit WNT signaling through independent mechanisms, indicating that their co-expression may have synergistic effects. Thus, these genes could be used to predict extent of bone disease and future risk of developing bone disease. Moreover, inhibitors of these proteins could be used to block bone disease. It is also possible that these factors play a role in osteoporosis in the general population.

WNT Signaling Pathway

Wnt genes comprise a large family of secreted polypeptides that are expressed in spatially and tissue-restricted patterns during vertebrate embryonic development. Mutational analysis in mice has shown the importance of Wnts in controlling diverse developmental processes such as patterning of the body axis, central nervous system and limbs, and the regulation of inductive events during organogenesis. The Wnt family of secreted growth factors initiates signaling via the Frizzled (Fz) receptor and its coreceptor, LDL receptor-related protein 5 or 6 (LPR5 or LRP6), presumably through Fz-LPR5/LRP6 complex formation induced by Wnt.

Secreted antagonists of Wnt include Frizzled (Fz)-related proteins (FRPs), Cerberus, Wnt inhibitory factor (WIF) and Dickkopf (DKK). Frizzled (Fz)-related proteins, Cerberus and Wnt inhibitory factor have all been shown to act by binding and sequestering Wnt. Unlike Wnt antagonists which exert their effects by molecular mimicry of Fz or Wnt sequestration through other mechanisms, Dickkopf-1 (DKK-1) specifically inhibits canonical Wnt signalling by binding to the LPR5/LRP6 component of the receptor complex.

DKK-1 is a head inducer secreted from the vertebrate head organizer and induces anterior development by antagonizing Wnt signaling. DKK-1 is a high-affinity ligand for LRP6 and inhibits Wnt signaling by preventing Fz-LRP6 complex formation induced by Wnt. DKK-1 binds neither Wnt nor Fz, nor does it affect Wnt-Fz interaction. DKK-1 function in head induction and Wnt signaling inhibition strictly correlates with its ability to bind LPR5/LRP6 and to disrupt the Fz-LPR5/LRP6 association. LPR5/LRP6 function and DKK-1 inhibition appear to be specific for the Wnt/Fz beta-catenin pathway. These findings thus reveal a novel mechanism for Wnt signal modulation.

WNT Signaling and Osteoblast Differentiation

Recent studies have shown that the Wnt signaling pathway is critical for osteoblast differentiation and function. Mice with a targeted disruption in the gene for low-density lipoprotein receptor-related protein 5 (LRP5) developed a low bone mass phenotype. LRP5 is expressed in osteoblasts and is required for optimal Wnt signaling in osteoblasts. In vivo and in vitro analyses indicated that this phenotype becomes evident postnatally, and it was secondary to decreased osteoblast proliferation and function in a Cbfa1-independent manner. In humans, mutations in LRP5 cause the autosomal recessive disorder osteoporosis-pseudoglioma syndrome (OPPG). Osteoporosis-pseudoglioma syndrome carriers have reduced bone mass when compared to age- and gender-matched controls.

Importantly, separate and distinct mutations in LRP result in a high bone mass phenotype. In contrast to the osteoporosis-psuedoglioma mutations, the high bone mass traits are gain of function mutations. Markers of bone resorption were normal in the affected subjects, whereas markers of bone formation such as osteocalcin were markedly elevated. Levels of fibronectin, a known target of signaling by Wnt, were also elevated. In vitro studies showed that the normal inhibition of Wnt signaling by Dickkopf-1 (DKK-1) was defective in the presence of the mutation and that this resulted in increased signaling due to unopposed Wnt activity. These findings demonstrated the role of altered LRP5 function in high bone mass and point to DKK as a potential target for the prevention or treatment of osteoporosis.

WNT Signaling and Bone Disease in Multiple Myeloma

Indirect evidence of a role of DKK-1 in osteoblast function has been provided by identification of gain of function mutations in LRP-5 being linked to a high bone mass phenotype. In addition, targeted disruption of secreted firzzled-related protein (SFRP-1), a homologue of FRZB (SFRP-3), leads to decreased osteoblast and osteocyte apoptosis and increased trabecular bone formation.

A quantitative trait loci (QTL) influencing bone mass has been localized to the LRP-5 region, suggesting that the population at large have different risk of developing osteoporosis. It is conceivable that multiple myeloma bone disease may be influenced by the combined effects of DKK-1/FRZB expression with an inherited predisposition to low bone mass conferred by inherited LRP-5 alleles. Multiple myeloma cases may be genotyped for LRP-5 allele variations and correlate this information with bone disease, and DKK-1 and FRZB expression.

Monoclonal gammopathy of undetermined significance (MGUS), a plasma cell dyscrasia that is predisposed to develop into multiple myeloma, is differentiated from multiple myeloma by the lack of obvious bone disease. The significance of discovering DKK-1 and/or FRZB expression in a third of monoclonal gammopathy of undetermined significance is unclear but could suggest that these cases may be at higher risk for developing multiple myeloma. As with multiple myeloma, this predisposition may also be related to inherited LRP5 alleles. Alternatively, these monoclonal gammopathy of undetermined significance cases could have underlying preclinical bone disease that is not yet apparent by radiological scans.

Data presented herein suggests a model for how DKK-1 expression by multiple myeloma plasma cells can be linked to multiple myeloma disease growth control and bone destruction and how these two phenomena can be integrated by one molecule. In the model, primary multiple myeloma express high levels of DKK and these levels can be increased with drug therapies used to treat the disease. High levels of DKK-1 likely induce apoptosis of multiple myeloma cells and could explain the relatively slow progression of the disease in its early phase as cell growth is tempered by high rate of DKK-1 induced apoptosis. However, as the disease progresses there is an osteoclast-induced reduction in JUN and DKK-1 that eventually develops into a constitutive loss of JUN and DKK-1 expression as seen in extramedullary disease.

Thus, if one were to view DKK-1 expression from the perspective of the multiple myeloma plasma cells, high levels of DKK-1 expression could be seen as positive feature of the disease. However, with the mesenchymal cell lineage being exquisitely sensitive to DKK-1 induced apoptosis, the high levels of this secreted product likely has a double edge to it in that it also induces massive programmed cell death of osteoblast precursors and possibly even mesenchymal stem cells. It is expected that high levels of DKK-1 early in the disease could lead to a permanent loss of mesenchymal stem cells, a notion supported by the observed lack of bone repair after remission induction or during disease progression when osteoclasts likely suppress DKK-1 secretion by multiple myeloma plasma cells. Thus, exploitation of this knowledge might lead to the development of new therapies for multiple myeloma that accentuate DKK-1's effects on multiple myeloma plasma cells, but at the same time prevent DKK's bone damaging effects on osteoblast or their precursors.

The present invention also describes a molecular mechanism by which DKK1 likely inhibits osteoblast differentiation and contributes to myeloma bone disease. Initial experiments (FIGS. 42A and 42B) demonstrated that mouse and human pluripotent mesenchymal cell lines are capable of transducing a canonical Wnt signal. These cells expressed mRNA corresponding to multiple Wnt receptors and the LRP5/6 co-receptors, suggesting pre-osteoblasts are capable of interacting with Wnt ligand. Treatment with exogenous Wnt3a led to enhanced activation of a functional signaling pathway as evidenced by increases of both uncomplexed and transcriptionally active forms of b-catenin in the cytosol. Accumulation of beta-catenin in the cytoplasm leads to nuclear translocation and binding of TCF/LEF family members to form complexes capable of activating transcription. RT-PCR analysis (FIG. 42B) revealed that all members of the TCF family are expressed in mouse C2C12 cells, and TCF 1, 4, and LEF 1 are expressed in human osteoblast-like cell lines. Moreover, functional activation of these transcription factors following Wnt3a treatment was demonstrated using a luciferase reporter construct.

It has been reported that exogenous Dkk1 blocks Wnt3a-induced stabilization of b-catenin and inhibits activation of the canonical Wnt pathway in MM cells (qiang and Rudikoff, 2004; Qiang et al., 2003). In the present invention (FIG. 42C), it was observed that Dkk1 can similarly regulate Wnt-induced stabilization of beta-catenin in mouse and human pre-osteoblasts as Dkk1 protein produced by MM cell lines stably expressing the protein, or MM patient bone marrow plasma containing high levels of Dkk1, inhibited stabilization of b-catenin by Wnt3a. It is also noted that Dkk1 completely attenuates Wnt3a-induced TCF/LEF transcriptional activity in mouse pre-osteoblasts. Conflicting results exist as to the role of Dkk2 and other Dkk family members on pre-osteoblast differentiation (Li et al., 2005; van der Horst et al., 2005). Analysis of mRNA expression in the tested cell lines revealed relative expression of Dkk family mRNAs in the following order: Dkk3>Dkk2>Dkk1=Dkk4. Treatment of pre-osteoblast cells with supernatants containing Dkk2 inhibited b-catenin stabilization similarly to that observed with Dkk1. In addition, over-expression of Dkk1 or Dkk2 directly in C2C12 cells reduced endogenous b-catenin levels.

Although osteoblasts clearly respond to Wnt3a by enhanced activation of the canonical Wnt/b-catenin pathway, Wnt3a alone had no apparent effect on differentiation of osteoblast precursors as reflected by ALP production. Surprisingly, Dkk1 (or Dkk2) significantly blocked BMP-2-induced differentiation (FIG. 42D). These results indicate that an autocrine canonical Wnt signal present in OB precursor cells is necessary for BMP-2-induced differentiation. This conclusion is supported by several additional observations. First, abundant expression of multiple Wnt mRNAs was observed in all cell lines (unpublished data), in addition to Fz and LRP5/6 receptors (FIG. 42A). Second, silencing of LRP5 or LRP6 mRNA expression completely abrogated BMP-2-induced ALP activity (FIG. 42F). This result is consistent with previous reports showing that lack of LRP5 (Kato et al., 2002) and LRP6 (Kokubu et al., 2004) reduced bone formation and osteoblast differentiation in a mouse model. Third, higher levels of uncomplexed and transcriptionally active beta-catenin protein exist in these cells relative to osteoclasts, MM cells and other cell types. Fourth, blockage of endogenous b-catenin by a dominant negative b-catenin construct significantly inhibited BMP-2-induced C2C12 differentiation (FIG. 42E) in agreement with data indicating that over-expression of active b-catenin increased bone mass (Glass et al., 2005). Finally, constitutive expression of Dkk1 (or Dkk2, not shown) led to, not only reduced endogenous levels of uncomplexed and transcriptionally active b-catenin, but also decreased ALP activity following BMP-2 treatment. These results are consistent with previous in vivo studies showing that deletion of Dkk1 leads to increased bone formation and bone mass (Morvan et al., 2006; van der Horst, 2005), and over-expression of Dkk1 in transgenic mice results in osteopenia (Li et al., 2006). The present study provides direct evidence that endogenous b-catenin levels in mesenchymal cells are necessary for osteoblast differentiation, and Dkk1 from MM cells inhibits this process.

Since Dkk1 can block BMP-2 induced ALP production and Wnt signaling is necessary to induce differentiation, the possibility exists for cross regulation between these two pathways. Experiments to test this hypothesis revealed that BMP-2 treatment alone did not induce increased levels of beta-catenin over steady state (FIG. 42G), nor did it affect TCF/LEF transcriptional activity, nor did Wnt3a increase ALP activity (FIG. 42D). Furthermore, no association was observed between Dkk1 and BMP-2 receptors, and neither Wnt3a nor Dkk1 treatment led to activation of Smad-1, -5, and -8 (important downstream targets of BMP-2 activation that play a pivotal role in BMP-2-induced mesenchymal cell differentiation) (Canalis et al., 2003). Moreover, Cbfa-1/Runx2 transcription factor activity and increase in Smad6 mRNA induced by BMP treatment did not change in response to Wnt or DKK1, further indicating that Wnt-signaling does not activate the BMP pathway. However, the fact that Dkk1 did inhibit the canonical Wnt pathway and also BMP-2-induced osteoblast differentiation in the present study suggests that there is indeed co-regulation between BMP-2 and Wnt signaling of osteoblast differentiation. The nature of this co-regulation is the focus of active investigation.

In contrast to the lack of cross regulation described above, other studies have suggested that BMP-2 increases endogenous Wnt mRNA expression to promote increased ALP activity (Rawadi et al., 2003; Chen et al., 2006). Furthermore, BMP-2 and a b-catenin mutant with constitutive transcriptional activity (DeltaN151) synergized to stimulate ALP activity, osteocalcin gene expression, and matrix mineralization (Mhalaviele et al., 2005). However, in the present experiments, BMP-2 did not induce increased stabilization of cytosolic, free b-catenin in mouse and human pre-osteoblast cells, nor BMP-2 alone is able induced TCF/LEF transcriptal activity, nor did BMP-2 synerzies Wnt3a-induced TCF/LEF activity indicating that, under these conditions, BMP-2 is unlikely to alter baseline or steady state levels of Wnt signaling sufficient, and required, for BMP-2 induced differentiation. It appears that cross talk between BMP-2 and a canonical Wnt pathway does not occur at, or above, the analyzed downstream targets of each signaling pathway. Consistent with this hypothesis, Nakashima and colleagues have previously reported that BMP-2 alone failed to increase TCF/LEF activity (Nakashima et al., 2005) although these two pathways are required for preosteoblast differentiation. Moreover, Mbalaviele and colleagues provided in vivo evidence that BMP-2 does not influence TCF/LEF activity related to that activated by b-catenin mutant (ΔN151) in C3H10T1/2 cells (Mhalaviele et al., 2005). However, the possibility that interactions between Wnt and BMP-2 signaling pathways occur through alternate cascades cannot be excluded. In fact, in other systems, it has been reported that beta-catenin and LEF/TCF form complexes with Smads (Hu and Rosenblum, 2005). Additionally, Wnt3a and BMP-2 (Willert et al., 2002) can induce expression of the ID2 gene and both induced MSX1 gene expression (Binato et al., 2006). Further studies will be required to clarify these differences.

Since it is thought that LRP5 or LRP6 can act redundantly, the reasons for observing an almost complete loss of BMP-2 induced ALP activity, when only one of the two was silenced are not clear. It may be that the amount of LRP5 or LRP6 on cell surface tightly regulates Wnt signaling required for BMP-2 induced ALP. While required, either alone is not sufficient. Indeed, Wnt-1 induced TCF/LEF transcriptional activity was almost completed blocked in fibroblast in LRP6 null mice in the presence of LRP5 (Kokubu et al., 2004). On the other hand, expression of loss-function of LRP5 mutant almost completely abolishes BMP-2 induced ALP activity in the presence of LRP6 in ST2 pluripotent bone marrow stromal cells (Gong et al., 2001). Another explanation could be that the trafficking of LRP5 and LRP6 on the cell surface might regulate Wnt signaling. This is consistent with recent studies that show that R-Spondin-1 regulates LRP6 cell surface levels of LRP6 by interfering with Dkk1/Kremen-mediated internalization of LRP6 (Binnerts et al., 2007). Further studies will be needed to distinguish these hypotheses In conclusion the above studies have revealed that autocrine Wnt signaling in osteoblasts is necessary to promote BMP-2-mediated differentiation of pre-osteoblast cells, while Wnt signaling alone is not capable of inducing such differentiation. Dkk1 inhibits this process and may be a key factor regulating pre-osteoblast differentiation, thereby emphasizing the importance of Dkk1 as a molecular target for novel therapeutic approaches to modulate myeloma bone disease.

The present invention also demonstrates that DKK1 may contribute to osteolytic bone lesion in MM by attenuating Wnt signaling in osteoblasts that prevents their differentiation and hence alters the expression of OPG and RANKL in favor of RANKL, which in turn leads to increased osteoclastogenesis in the local environment surrounding the plasma cell foci within the bone. The evidence supporting this model are the following: 1) DKK1 inhibits Wnt3a-induced stabilization of beta-catenin and reduces free-beta-catenin in both mouse and human osteoblast cells, 2) exogenous administration of DKK1 or constitutive expression of DKK1 dramatically diminished Wnt3a induced OPG expression in osteoblasts, 3) silencing DKK1 expression in human osteoblast-like cells expressing endogenous DKK1 increases sensitivity and reaction to Wnt3a stimulation as determined by increases in OPG expression, 4) MM bone marrow serum containing high DKK1 blocked Wnt3-mediated OPG expression, 5) mimicking the interaction between osteoblasts and MM cells in the bone marrow, a co-culture system also revealed that the DKK1-secreting OPM-2 mM cell line and primary CD138-selected plasma cells from MM patients dramatically attenuated Wnt3a-induced OPG mRNA and protein production by osteoblasts, and 6) a neutralizing DKK1-antibody could restore OPG expression in osteoblasts that was inhibited by the presence of MM bone marrow serum or primary MM plasma cells. Taken together, these results support the notion that DKK1 interrupts Wnt signaling-regulated bone resorption through regulation of osteoclastogenesis by inhibiting OPG expression. Indeed, OPG levels are decreased in myeloma relative to healthy controls (Lipton et al., 2002; Seidel et al., 2001). The importance of OPG is evidenced by the fact that administration of recombinant OPG or OPG peptidomimetic, OP34, can inhibit bone resorption and MM-associated osteolytic bone disease in murine models (Vanderkerken et al., 2003; Heath et al., 2007). In fact, Wnt signaling appears to indirectly inhibit osteoclastogenesis as well. It was observed that supernatants from osteoblast cells transfected with domain negative beta-catenin contain higher RANKL and lower OPG levels and these supernatants increase human osteoclasts from CD34 mononuclear cells isolated from bone marrow of MM patients relative to control supernatant (Ya-Wei Qiang unpublished data, 2007). This is consistent with in-vivo data that show that deletion of beta-catenin results in marked increase in osteoclast cell number (Holmen et al., 2005).

In contrast to the inhibitory effect of DKK1 on Wnt-stimulated OPG expression in osteoblast cells interacting with MM cells, DKK1 restores RANKL expression in osteoblast cells. Supporting this hypothesis are the following observations: 1) DKK1 significantly reversed Wnt3a-mediated downreglation of RANKL expression in mouse and human osteoblast-like cell lines, and 2) overexpression of DKK1 in osteoblast cells and MM serum with high DKK1 levels reversed Wnt3a-mediated downregulation of RANKL expression in mouse and human osteoblast-like cell lines. These results are consistent with studies in which DKK1 increases RANKL expression in the mouse osteoblast cell line C3H10T1/2. A role of Wnt signaling in the regulation of RANKL expression was first recognized by Holmen and colleagues who reported that an increase in canonical Wnt signaling by deletion of the Wnt inhibitory molecule APC results in an increase in RANKL expression in normal osteoblast cells in mice (Holmen et al., 2005). More recently, Spencer and colleagues illustrated that the human RANKL promoter contains TCF/LEF binding sites and overexpression of full-length beta-catenin inhibits RANKL promoter activity through a currently unknown mechanism in MC3T3-E1 cells (Spencer et al., 2006). Although the source of RANKL is controversial, several groups have reported a role for RANKL in MM-triggered bone lesions. RANKL is upregulated in myeloma cells (Giuliani et al., 2001; Pearse et al., 2001) and increased levels of RANKL in MM serum is used as prognostic index for indicating a survival in MM patients (Terpos et al., 2003).

To reach comparable levels of beta-catenin stabilization, higher concentrations of Wnt3a were required in human osteoblasts than mouse osteoblasts, which may be attributable to dramatically higher levels (approximately 50-fold) of endogenous DKK1 in human osteoblast lines, since mouse and human lines have similar expression patterns of endogenous Wnt ligands and LRP5/6 co-receptor and Fz receptors. Consequently, ectopic constitutive expression of DKK1 in mouse C2C12 cells, which lack DKK1 expression, blocked Wnt3a-induced OPG expression to an extent similar to that seen with human osteoblast cells, which express high levels of endogenous DKK1. In contrast, knockdown of endogenous DKK1 expression in human osteoblast cells restored sensitivity to Wnt3a stimulation as exhibited by an increase in OPG expression. Thus, endogenous DKK1 in osteoblasts appears to be a key factor determining sensitivity to exogenous Wnt stimulation. The difference in DKK1 expression between these cells might represent the different specific stage of osteoblast differentiation that the cells represent, as the mouse osteoblast progenitor cell line C2C12 represents more immature progenitor cell the human osteosarcoma cells used (Katagiri et al., 1994). This notion is supported by the fact that DKK1 expression is high in late-stage osteoblast cell line KS463 (van der Horst et al., 2005). One can not exclude the possibility that this difference might reflect differences between mouse and man as human bone marrow derived mesenchymal cells express high levels of DKK1 (Giuliani et al., 2007) and DKK1 regulates human, but not mouse, mesenchymal cell differentiation into adipocytes or osteoblasts. Hence, the endogenous DKK1 levels in osteoblast cells should be considered an important factor when selecting as a model for studies role of Wnt signaling in regulation of OPG and RANKL Although Wnt3a regulates both OPG and RANKL expression and DKK1 interrupts this process, it is interesting to note that Wnt3a stimulation had stronger effects on OPG expression than that of RANKL in these experiments. Wnt3a induced a much higher increase in OPG expression in response to Wnt3a compared with the inhibitory effect on RANKL expression. In addition, while anti-DKK1 antibody restored DKK1-suppressed OPG expression, it had no effect on DKK1-mediated increase of RANKL in osteoblast cells in coculture with primary MM cells. Thus, OPG seems to be more sensitive to Wnt signaling than RANKL. However, it has clearly been shown that overexpression of DKK1 and blockage of endogenous canonical Wnt signaling by expression of dominant negative b-catenin significantly increases RANKL mRNA and protein. Thus, it is likely that DKK1-mediated suppression of OPG, rather than its effect to release a block to RANKL expression, may be the more important event contributing to MM OBL. However, the possibility that endogenous Wnt ligands regulate OPG and RANKL and as such regulate homeostasis of osteoclastogenesis in normal physiological conditions cannot be excluded since osteoblast cells express many Wnt ligands. Another possibility that was not addressed herein was whether endogenous Wnt signaling modulates RANKL expression at levels that are bellow the levels of sensitivity of current methods used to detect RANKL protein. This is supported by the fact that constitutive expression of DKK1 and lack of transcriptional activity of beta-catenin in osteoblast cells restores RANKL expression.

It is noteworthy that Gunn and colleagues have shown that conditioned media from MSCs can induce multiple myeloma cells lines to produce DKK1 and that these cells also produce high levels of IL-6 (Gregory et al., 2003; Gunn et al., 2006) a myeloma growth factor (Kishimoto, 2005). Importantly, Gunn et al showed that IL-6-dependent myeloma cell lines growth in MSC conditioned media and that this growth is inhibited when a neutralizing antibody to IL-6 is added to the cultures.

Furthermore, the present invention also demonstrated that blocking of DKK1 activity in primary human myeloma-bearing SCID-rab mice was associated with increased osteoblast numbers and reduced osteoclast activity. This decreased osteoclast numbers in myelomatous bones from SCID-Hu mice could be due to a reduction of RANKL and increase in OPG. These effects resulted in prevention of bone resorption, increased bone formation and most importantly inhibition of tumor burden. The present invention also establishes, that Multiple Myeloma bone disease and tumor growth are interdependent, as blocking DKK1 activity, was accompanied by inhibition of Multiple Myeloma by blocking DKK1 activity progression. These in vivo data confirmed that DKK1 is critical factor involved in myeloma bone disease and tumor progression. Thus, therapeutic approaches to inhibit DKK1 activity in patients with myeloma will not only improve skeletal complications and quality of life but also help control myeloma. In addition, the present invention also demonstrated, that blocking of DKK1 activity in SCID-rab mice had bone anabolic effects on non-myelomatous bones, suggesting that DKK1 neutralization may have broad applications in bone disorders.

Taken together, the present invention proposes a working hypothesis that myeloma-derived DKK1 can act as a master regulator of OBL and myeloma disease survival. DKK1-mediated inhibition of Wnt-regulated osteoblast differention results in a loss of their functional activity to replace bone resorbed by osteoclasts. This leads to increased expression of IL-6, an essential survival factor for myeloma. This block of Wnt signaling also leads to a loss of expression of OPG and increased expression of RANKL. It is contemplated that the shift in the RANKL-to-OPG ratios, at the site of boney plasmacytomas, being propagated by high local concentrations of IL-6, results in increased local osteoclastogenesis and increased bone resorption with no anabolic response. Thus, DKK1 represents an important new and therapeutically tractable target as has been suggested herein and by preclinical studies.

In one embodiment of the present invention, there is provided a method of controlling bone loss in an individual, comprising the step of inhibiting a WNT signaling antagonist at the nucleic acid or protein level. Specifically, the inhibition of Wnt signaling antagonist may block induction of Wnt ligand, restore RANKL/OPG levels or both. Examples of WNT signaling antagonist may include but are not limited to soluble frizzled related protein 3 (SFRP-3/FRZB) or the human homologue of Dickkopf-1 (DKK1). The inhibition at the nucleic acid level may be due to Wnt antagonist specific peptide nucleic acid or siRNA. Alternatively, the inhibition at the protein level may be due to said Wnt antagonist specific antibodies, anti-sense oligonucleotides or small molecule inhibitors. Examples of individual who may benefit from such a method may include but are not limited to ones with multiple myeloma, osteoporosis, post-menopausal osteoporosis and malignancy-related bone loss. The malignancy-related bone loss may be caused by breast cancer metastasis to the bone or prostate cancer metastasis to the bone.

In another embodiment of the present invention, there is a method of treating bone disease in an individual, comprising the step of: administering to the individual a pharmacologically effective amount of an inhibitor of a WNT signaling antagonist such that the administration blocks induction of Wnt ligand, restores RANKL/OPG levels or both. Examples of the WNT signaling antagonist may include but are not limited to soluble frizzled related protein 3 (SFRP-3/FRZB) or the human homologue of Dickkopf-1 (DKK1). The inhibitor may inhibit the Wnt signaling antagonist at the nucleic acid or protein level. Examples of the inhibitor at the nucleic acid level and protein level and those individuals benefiting from such a method are same as discussed supra. Additionally, the inhibitor may treat the bone disease by preventing bone resorption, increasing bone formation or both.

In yet another embodiment of the present invention, there is a method of inhibiting tumor growth in bone of an individual, the method comprising the step of blocking the activity of DKK1. Generally, the DKK1 activity is blocked by administering anti-DKK1 antibodies, DKK1 anti-sense oligonucleotides or small molecule inhibitor to the individual. Moreover, an individual who will benefit from such a method although not limited to includes one who has multiple myeloma, metastatic breast cancer or prostate cancer.

In another embodiment of the present invention, there is a method of screening for a compound that controls bone loss and inhibits human myeloma cell growth, comprising: engrafting human myeloma cells in a rabbit bone implanted in a SCID-rab mouse, administering the compound to the mouse; and comparing bone mineral density of the implanted bone and level of serum human monoclonal immunoglobulin in the mouse with a control SCID-rab mouse that has not received the compound, where an increase in the bone mineral density and a decrease in the level of serum immunoglobulin in the treated mouse compared to the control mouse indicates that the compound controls bone loss and inhibits human myeloma growth. Generally, the compound is an inhibitor of WNT signaling antagonist. Specifically, the WNT signaling antagonist is human homologue of Dickkopf-1 (DKK1) or soluble frizzled related protein 3 (SFRP-3/FRZB).

In yet another embodiment of the present invention, there is a method of inhibiting multiple myeloma growth in an individual suffering from multiple myeloma, said method comprising the step of blocking the activity of DKK1. This method may further comprise increasing osteoblastogenesis and decreasing osteoclastogenesis. The increase in osteoblastogenesis and the decrease in osteoclastogenesis is due to blocking of induction of Wnt ligand, restoring RANKL/OPG levels or both. Examples of inhibitors blocking the DKK1 activity are the same as discussed supra.

As used herein, the term, "a" or "an" may mean one or more. As used herein in the claim(s), when used in conjunction with the word "comprising", the words "a" or "an" may mean one or more than one. As used herein "another" or "other" may mean at least a second or more of the same or different claim element or components thereof.

As discussed herein, the inhibitor of Wnt antagonist described herein may be used in vitro or ex vivo by exposing the cell culture to the composition in a suitable medium. In vivo may be achieved by any known methods in the art.

The inhibitor of Wnt antagonist described herein or known in the art may be administered independently one or more times to achieve, maintain or improve upon a therapeutic effect. It is well within the skill of an artisan to determine dosage or whether a suitable dosage of such an inhibitor comprises a single administered dose or multiple administered doses. An appropriate dosage depends on the subject's health, the repair of the lytic bone lesion and prevention of tumor progression, the route of administration and the formulation used.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

EXAMPLE 1

Patients 174 patients with newly diagnosed multiple myeloma, 16 patients with monoclonal gammopathy of undetermined significance, 9 with Waldenstrom's 5 macroglobulinemia, and 45 normal persons were studied. Table 1 shows the characteristics of the patients with multiple myeloma.

TABLE 1

Myeloma patient characteristics and their relationship to MRI lesions

| Variable | n/N | % | MRI = 1+ | MRI = 0 | P value |
|---|---|---|---|---|---|
| Age ≧65 yr | 23/169 | 14 | 17/132 (12.9%) | 6/36 (16.7%) | 0.59* |
| Caucasian | 147/169 | 87 | 113/132 (85.6%) | 33/36 (91.7%) | 0.42* |
| Female | 68/169 | 40 | 55/132 (41.7%) | 13/36 (36.1%) | 0.55 |
| Kappa light chain | 104/165 | 63 | 79/128 (61.7%) | 24/36 (66.7%) | 0.59 |
| Lambda light chain | 61/165 | 37 | 49/128 (38.3%) | 12/36 (33.3%) | 0.59 |
| IgA subtype | 39/169 | 23 | 25/132 (18.9%) | 14/36 (38.9%) | 0.012 |
| B2M ≧4 mg/L | 60/169 | 36 | 47/132 (35.6%) | 13/36 (36.1%) | 0.96 |
| CRP ≧4 mg/L | 12/166 | 7 | 11/129 (8.5%) | 1/36 (2.8%) | 0.47* |
| Creatinine ≧2 mg/dL | 19/169 | 11 | 16/132 (12.1%) | 3/36 (8.3%) | 0.77* |
| LDH ≧190 UI/L | 52/169 | 31 | 44/132 (33.3%) | 8/36 (22.2%) | 0.20 |
| Albumin <3.5 g/dL | 23/169 | 14 | 19/132 (14.4%) | 4/36 (11.1%) | 0.79* |
| Hgb <10 g/dL | 40/169 | 24 | 31/132 (23.5%) | 8/36 (22.2%) | 0.87 |
| PCLI ≧1% | 23/150 | 15 | 18/119 (15.1%) | 4/30 (13.3%) | 1.00* |
| ASPC ≧33% | 109/166 | 66 | 82/129 (63.6%) | 26/36 (72.2%) | 0.33 |
| BMPC ≧33% | 104/166 | 63 | 79/129 (61.2%) | 24/36 (66.7%) | 0.55 |

TABLE 1-continued

Myeloma patient characteristics and their relationship to MRI lesions

| Variable | n/N | % | MRI = 1+ | MRI = 0 | P value |
|---|---|---|---|---|---|
| Cytogenetic abnormalities | 52/156 | 33 | 45/121 (37.2%) | 6/34 (17.6%) | 0.032 |
| CA13 or hypodiploid | 33/52 | 63 | 31/121 (25.6%) | 3/34 (8.8%) | 0.037 |
| Other CA | 19/52 | 37 | 53/103 (51.5%) | 16/32 (50.0%) | 0.89 |
| FISH13 | 69/136 | 51 | 103/136 (75.7%) | 28/36 (77.8%) | 0.80 |
| Osteopenia | 131/173 | 76 | | | |
| 1+ Lesions by MRI | 137/173 | 79 | | | |
| 3+ Lesions by MRI | 108/173 | 62 | | | |
| 1+ Lesions by X-ray | 105/174 | 60 | | | |
| 3+ Lesions by X-ray | 69/174 | 40 | | | |

*Fisher's Exact test, otherwise Chi-square test

EXAMPLE 2

Bone Imaging

Images were reviewed, without prior knowledge of gene expression data, using a Canon PACS (Picture Archiving and Cataloging System). MRI scans were performed on 1.5 Tesla GE Signa™ scanners. X-rays were digitized from film in accordance with American College of Radiology standards. MRI scans and x-rays were linked to the Canon PACS system using the ACR's DICOM (Digital Imaging and Communications in Medicine) standard. Imaging was done in accordance with manufacturers' specifications. MRI images were created with pre- and post-gadolinium T1-weighting and STIR (short-tau inversion recovery) weighting.

EXAMPLE 3

Plasma Cell Isolation and Gene Expression Profiling

Following Ficoll-Hypaque gradient centrifugation, plasma cells obtained from the bone marrow were isolated from the mononuclear cell fraction by immunomagnetic bead selection using a monoclonal mouse anti-human CD138 antibody (Miltenyi-Biotec, Auburn, Calif.). More than 90 percent of the cells used for gene expression profiling were plasma cells, as shown by two-color flow cytometry using CD138$^+$/CD45$^-$ and CD38$^+$/CD45$^-$ markers, the presence of cytoplasmic immunoglobulin light chains by immunocytochemistry, and morphology by Wright-Giemsa staining. Total RNA was isolated with RNeasy Mini Kit (Qiagen, Valencia, Calif.). Preparation of labeled cRNA and hybridization to U95Av2 microarrays containing approximately 10,000 genes (Affymetrix, Santa Clara, Calif.) was performed as previously described (Zhan et al., 2002; Zhan et al., 2003). RNA amplification was not required.

EXAMPLE 4

Immunohistochemistry

An antibody from a goat that was immunized against the entire human DKK1 protein (R&D Systems, Minneapolis, Minn.) was diluted 1:200 in Tris-buffer and added to formalin-fixed, paraffin-embedded bone marrow biopsy sections for 2 hours at room temperature. Adjacent sections were stained with H & E. Antigen-antibody reactions were developed with DAB (after biotinylated anti-goat antibody [Vector Laboratories, Burlingame, Calif.][1:400 dilution] and streptavidin-horse radish peroxidase [Dako] staining), and counterstained with Hematoxylin-2.

EXAMPLE 5

Enzyme Linked Immunosorbent Assay (ELISA)

Nunc-Immuno MaxiSorp surface microtiter plates were coated with 50 ml of anti-DKK1 antibody at 1 mg/ml in 1× phosphate buffered saline, pH 7.2 at 4° C. overnight, and blocked with 4 percent bovine serum albumin. Bone marrow plasma was diluted 1:50 in dilution buffer (1× phosphate buffered saline+0.1 Tween-20+1 percent bovine serum albumin). A total of 50 µl was loaded per well and incubated overnight at 4° C., washed and incubated with biotinylated goat anti-human DKK1 IgG (R&D Systems) diluted to 0.2 mg/ml in dilution buffer, followed by addition of 50 µl of 1:10,000 dilution of streptavidin-horse radish peroxidase (Vector Laboratories), all according to manufacturer's recommendations. Color development was achieved with the OPD substrate system (Dako) based on manufacturer's instructions. Serial dilutions of recombinant human DKK1 (R&D Systems) were used to establish a standard curve. The cell line T293, which does not express endogenous DKK1 and T293 with stably transfected DKK1 (Fedi, et al., 1999) were used to validate the ELISA assay.

EXAMPLE 6

Osteoblast Differentiation Assays

C2C12 mesenchymal precursor cells (American Type Tissue Culture, Reston, Va.) were cultured in DMEM (Invitrogen, Carlsbad, Calif.) supplemented with 10 percent heat-inactivated fetal calf serum. Alkaline phosphatase activity in C2C12 cells was measured as described (Gallea, et al., 2001; Spinella-Jaegle, et al., 2001). Cell lysates were analyzed for protein content using the micro-BCA assay kit (Pierce, Rockford, Ill.).

EXAMPLE 7

Statistical Analyses

Bone disease in multiple myeloma patients was modeled using logistic regression. Independent variables considered were gene expression intensity values (average difference calls) from ~10,000 genes (12,625 probe sets) measured using version 5.01 MAS (Affymetrix, Santa Clara, Calif.) from 174 cases of newly diagnosed multiple myeloma. The "Signal", a quantitative measure of gene expression, for each probe set was transformed to $\log_2$ before entry into the logistic regression model and permutation-adjustment analysis. There was no prior hypothesis with regard to genes that might be associated with bone disease in myeloma. As a result a univariate model of bone disease for each of the 12,625 probe sets was used. Candidate genes were refined using t-tests with permutation-adjusted significance levels (Westfall and Young, 1993). The Westfall and Young analysis was used to adjust for the multiple univariate hypothesis tests. Group differences in DKK1 signal and DKK1 protein levels were tested using the Wilcoxon rank sum test. Significant differences in patient characteristics by status of bone disease were tested using either the Fisher's exact test or the chi-square test. Expression intensities of genes identified by logistic regression were visualized with Clusterview (Golub, et. al., 1999). Spearman's correlation coefficient was used to measure correlation of gene expression and protein levels. Significant differences, in osteoblast differentiation, between the control and each experimental condition were tested using the Wilcoxon rank sum test; separate comparisons were made for each unique C2C12 experiment. Two-sided p-values less than 0.05 were considered significant and two-sided p-values less than 0.10 were considered marginally significant.

EXAMPLE 8

Gene Expression Profiling of Myeloma Cells

To identify genes that were overexpressed and associated with the presence of bone lesions, comparing microarray data from patients with or without bone lesions were performed. As MRI-defined focal lesions of bone can occur before radiologically identifiable lytic lesions, T1-weighted and STIR-weighted imaging to evaluate bone lesions were used. The gene expression patterns of approximately 10,000 genes in purified plasma cells from the marrow of patients with no bone lesions (n=36) and those with 1 or more (1+) MRI-defined focal lesions (n=137) were modeled by logistic regression analysis. The model identified 57 genes that were expressed differently (P<0.0001) in the two groups of patients (FIG. 1A). These 57 genes were further analyzed by t-tests with permutation-adjusted significance (Westfall and Young, 1993). These statistical tests showed that 4 of the 57 genes were overexpressed in patients with 1+MRI lesions: dihydrofolate reductase (DHFR), proteasome activator subunit (PSME2), CDC28 protein kinase 2 (CKS2), and dick-kopf homolog 1 (DKK1). Given that the gene for the Wnt/β-catenin signaling antagonist DKK1 is the only one of the four that codes for a secreted factor and that Wnt/β-catenin signaling is implicated in bone biology, further tests on DKK1 were carried out. An analysis of the results from the 173 patients with myeloma showed that DKK1 signal for patients with I+MRI and no x-ray lesions differ significantly compared to patients with no MRI and no x-ray lesions (median signal: 2,220 vs. 285; p<0.001) but does not differ significantly compared to patients with I+MRI and 1+x-ray (median signal: 2,220 vs. 1,865; p=0.63) (FIG. 1B, Table 2).

Monoclonal gammopathy of undetermined significance (MGUS) is a plasma cell dyscrasia without lytic bone lesions and can precede multiple myeloma. In 15 of 16 cases of MGUS, DKK1 was expressed by bone marrow plasma cells at levels comparable to those in multiple myeloma with no MRI or x-ray lesions of bone (FIG. 1B). DKK1 was undetectable in plasma cells from 45 normal donors, and 9 patients with Waldenström's macroglobulinemia a plasma cell malignancy of the bone lacking bone lesions (FIG. 1B).

TABLE 2

DKK1 mRNA and protein levels in MRI/X-ray-lesion defined subgroups of MM

|  |  | No MRI/No X-ray | 1+ MRI/No X-ray | 1+ MRI/1+ X-ray |
|---|---|---|---|---|
|  | N | 36 | 33 | 104 |
| DKK1 (Signal) (mRNA) | Mean | 536.1 | 3146.5 | 3415.1 |
|  | (Std) | (720.7) | (3079.9) | (4870.8) |
| DKK1 (Signal) (protein) | Min, | 19.2, | 16.4, | 9.4, |
|  | Median, | 284.9, | 2220.2, | 1864.7, |
|  | Max | 3810.2 | 10828.4 | 28859.1 |
|  | N | 18 | 9 | 41 |
| DKK1 (ng/ml) (mRNA) | Mean | 9.0 | 24.0 | 34.3 |
|  | (Std) | (4.7) | (17.7) | (75.3) |
| DKK1 (ng/ml) (protein) | Min, | 1.8, | 7.4, | 2.5, |
|  | Median, | 8.7, | 20.4, | 13.5, |
|  | Max | 19.7 | 61.8 | 475.8 |

EXAMPLE 9

Global Gene Expression Reveals DKK-1 and FRZB Linked to Lytic Bone Lesion in Multiple Myeloma In order to further identify the molecular determinants of lytic bone disease, the expression profiles of ~12,000 genes in CD138-enriched plasma cells from newly diagnosed multiple myeloma patients exhibiting no radiological evidence of lytic lesions on bone surveys (n=28) were compared to those with ≧3 lytic lesions (n=47). The Chi-square test of absolute calls (a qualitative measure of gene expression) was used to identify 30 genes that distinguished the two forms of disease (P<0.05). The Wilcoxon Rank Sum (WRS) test of the signal call (a quantitative measure of gene expression) revealed that 104 genes (49 up- and 55 down-regulated) differentiated the two disease subtypes (P<0.001).

Figure 2:
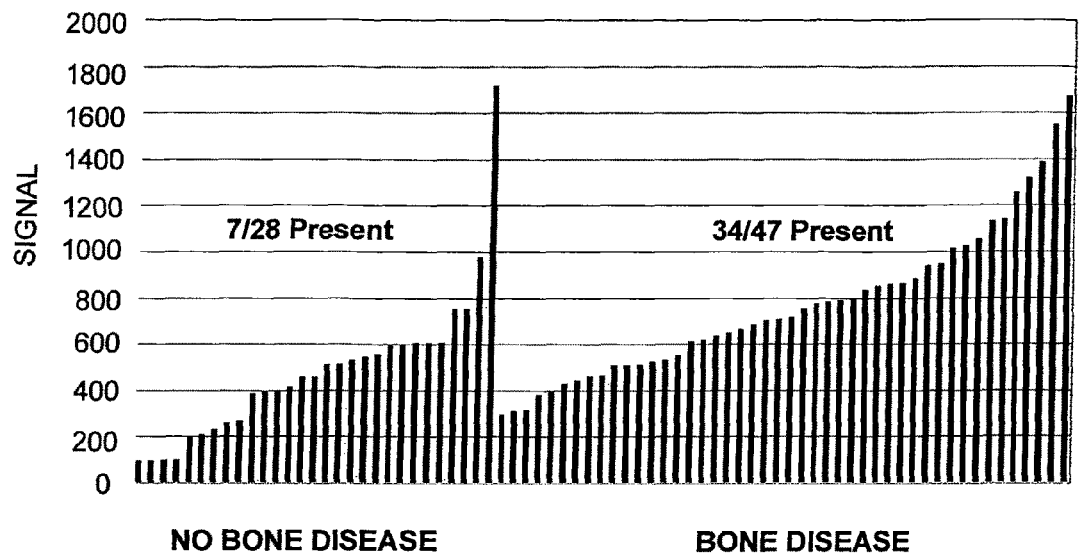
FIG. 2 shows RHAMM was up-regulated in multiple myeloma patients with bone lesions.
Figure 3:
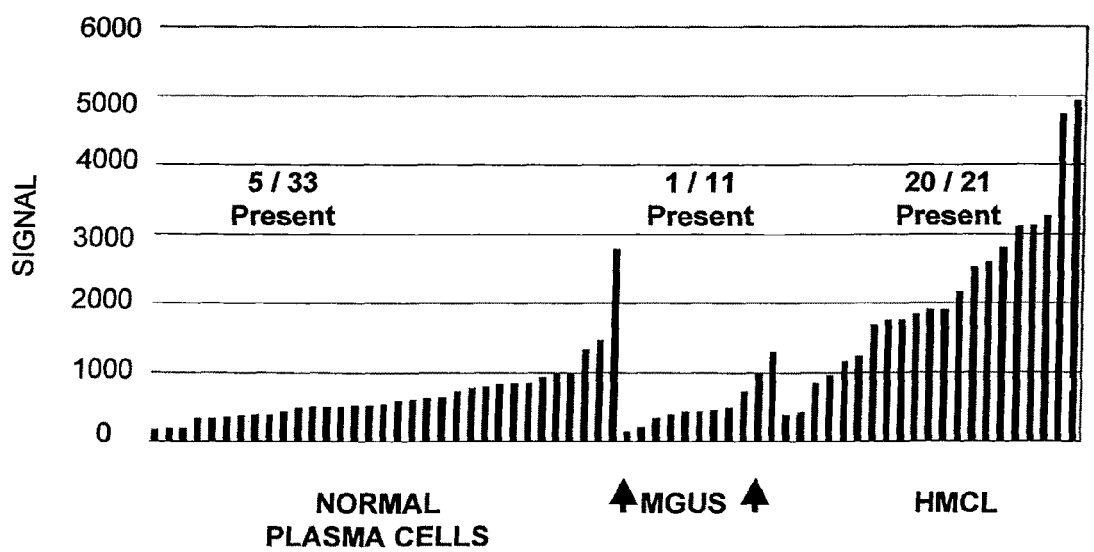
FIG. 3 shows RHAMM rarely present in normal plasma cells and monoclonal gammopathy of undetermined significance (MGUS), but it was present in virtually all human myeloma cell lines.

The Chi-square test identified the RHAMM proto-oncogene as the most significant discriminator between the two groups. It was expressed in only 7 of 28 patients with no bone disease compared with 34 of 47 patients with bone disease (FIG. 2). As expected, plasma cells from only 1 of 11 monoclonal gammopathy of undetermined significance expressed RHAMM (FIG. 3). WRS ranked RHAMM as the 14$^{th}$ most significant discriminator between the lytic lesion group and no lytic lesion group. NCALD, a calcium binding protein involved in neuronal signal transduction, was present in 11/28 (40%) of no lytic lesion group but only in 2/47 (4%) lytic lesion group. Other notable genes identified by Chi-square analysis included FRZB, an antagonist of Wnt signaling, that was present in 40/47 (85%) of lytic lesion group and 15/28 (53%) of no lytic lesion group. CBFA2/AML1B has been linked to MIP1α expression and was present in 50% of the no lytic lesion group and in 79% of the lytic lesion group.

Figure 4:
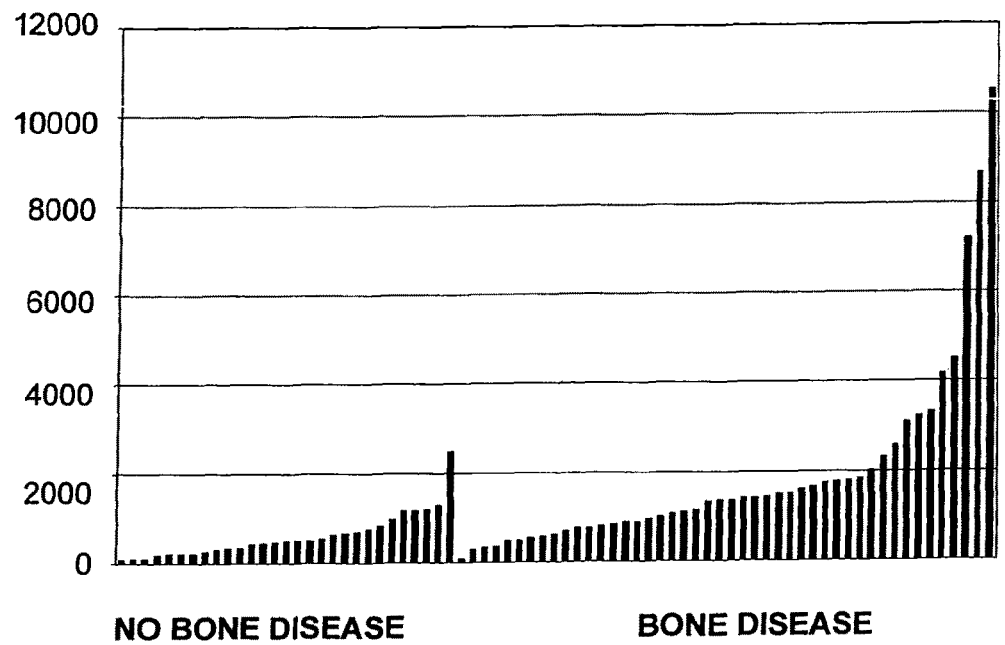
FIG. 4 shows securin was up-regulated in multiple myeloma patients with bone disease.
Figure 5:
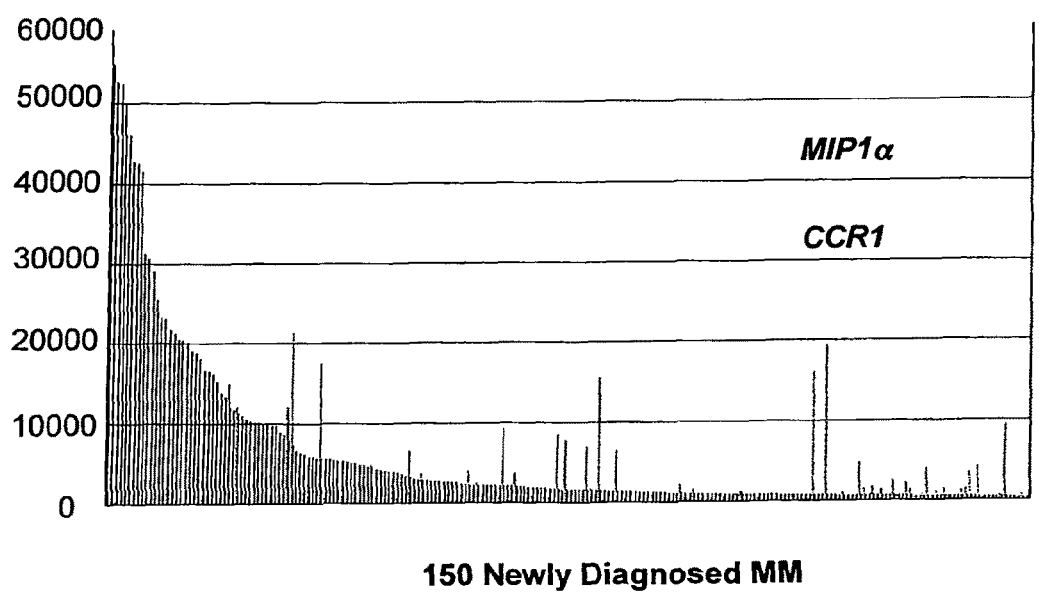
Figure 6:
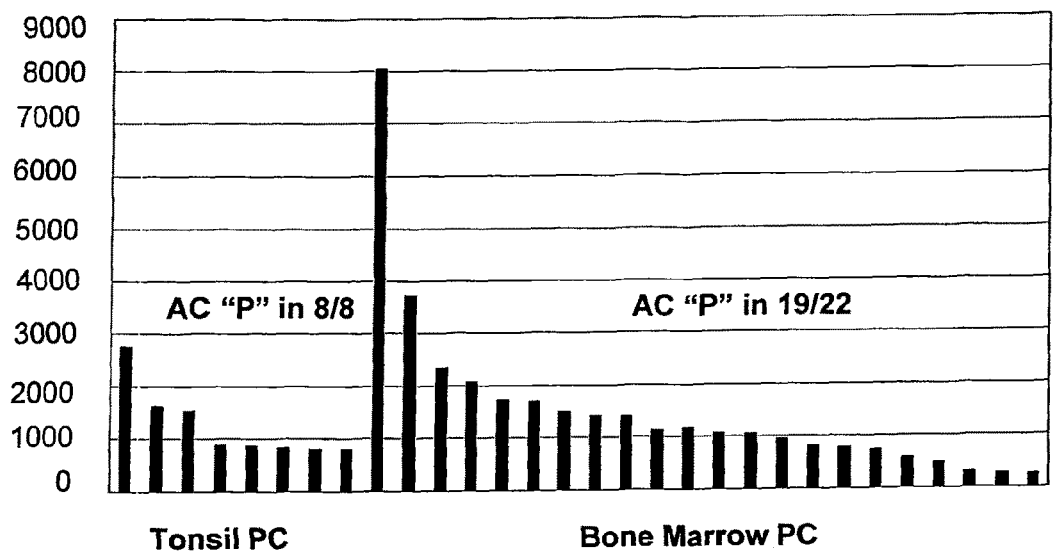
FIG. 6 shows MIP-1a was expressed at low level in normal plasma cells (PC).
Figure 7:
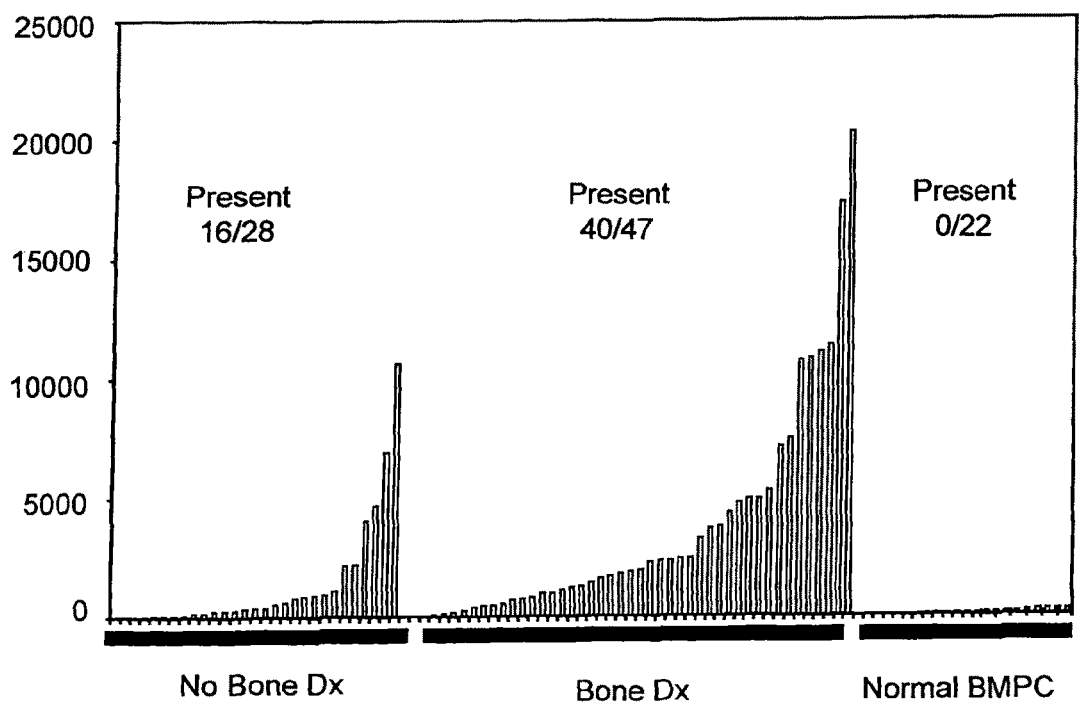
FIG. 7 shows the expression of WNT antagonist DKK-1 in multiple myeloma with bone lesions.
Figure 8:
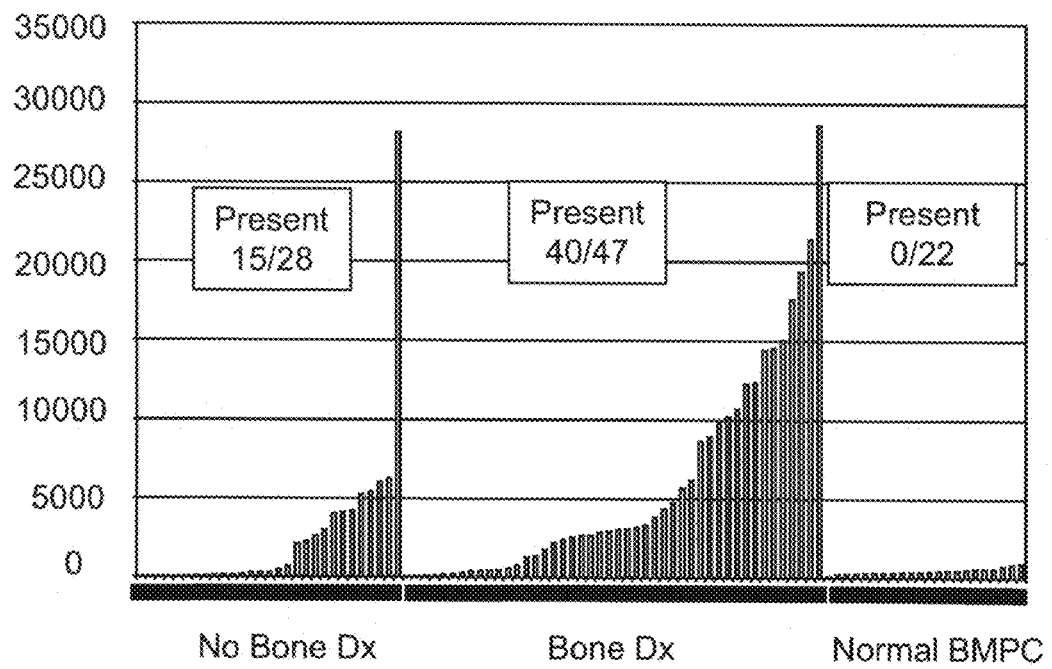
FIG. 8 shows the expression of WNT decoy receptor FRZB in multiple myeloma with lytic bone lesions.
Figure 9:
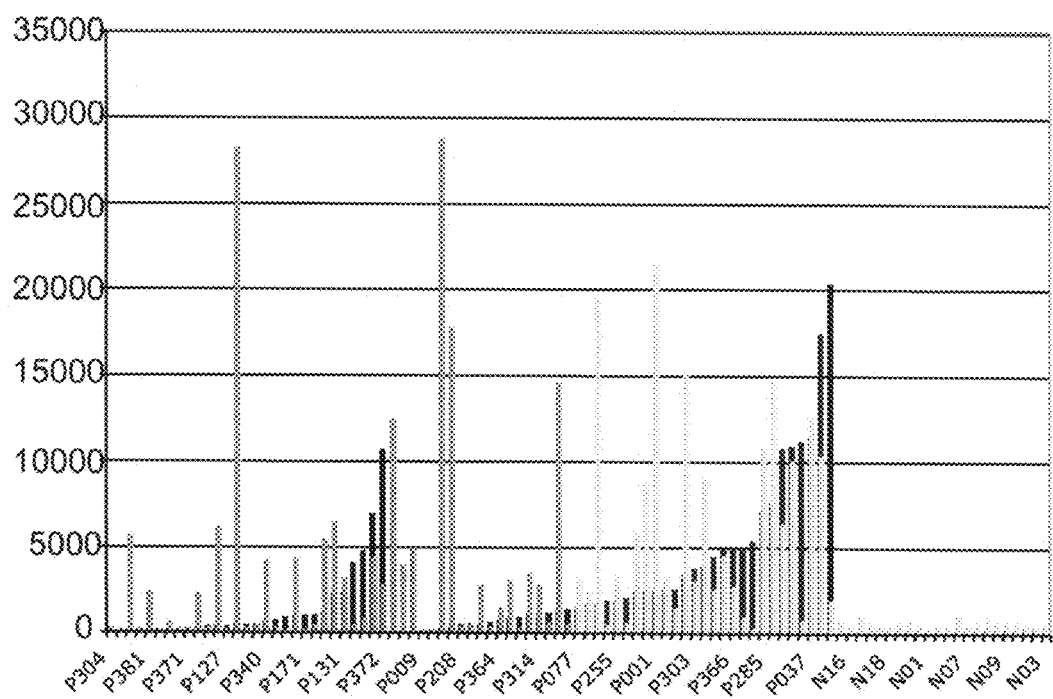
FIG. 9 shows the expression of DKK-1 and FRZB in multiple myeloma with lytic bone lesions. Black bar: DKK-1; gray bar: FRZB.
Figure 10:
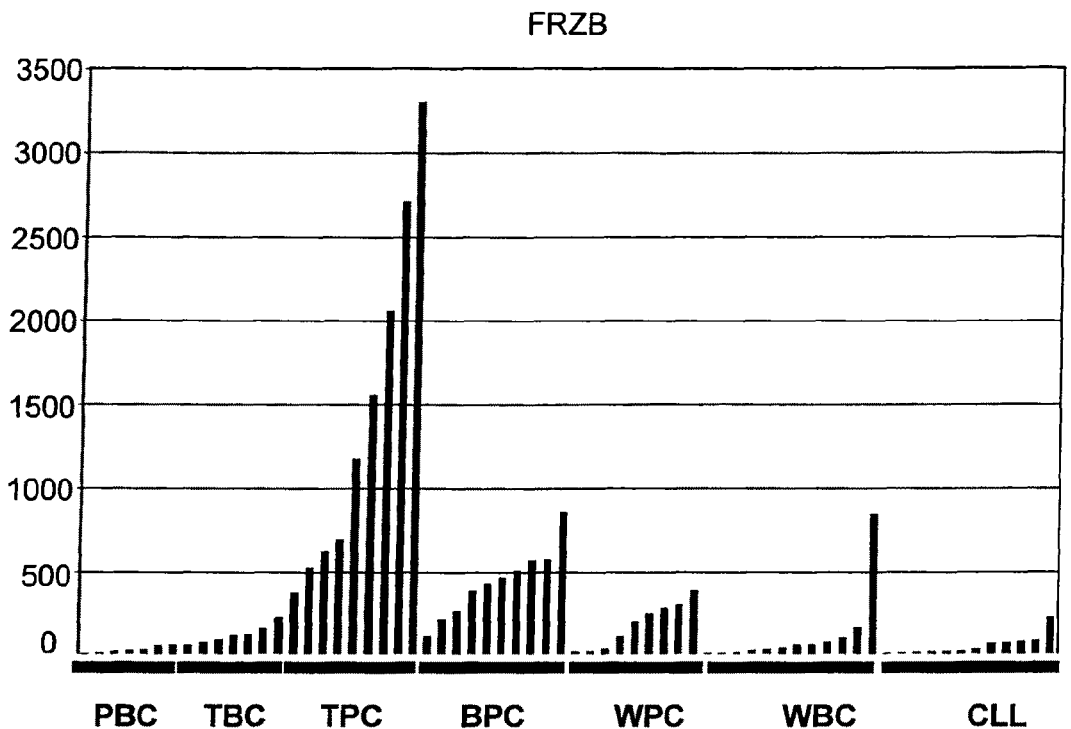
FIG. 10 shows FRZB was expressed in tonsil plasma cells. PBC, TBC, tonsil B cells; TPC, tonsil plasma cells; BPC, bone marrow plasma cells; WPC, WBC, CLL.
Figure 11:
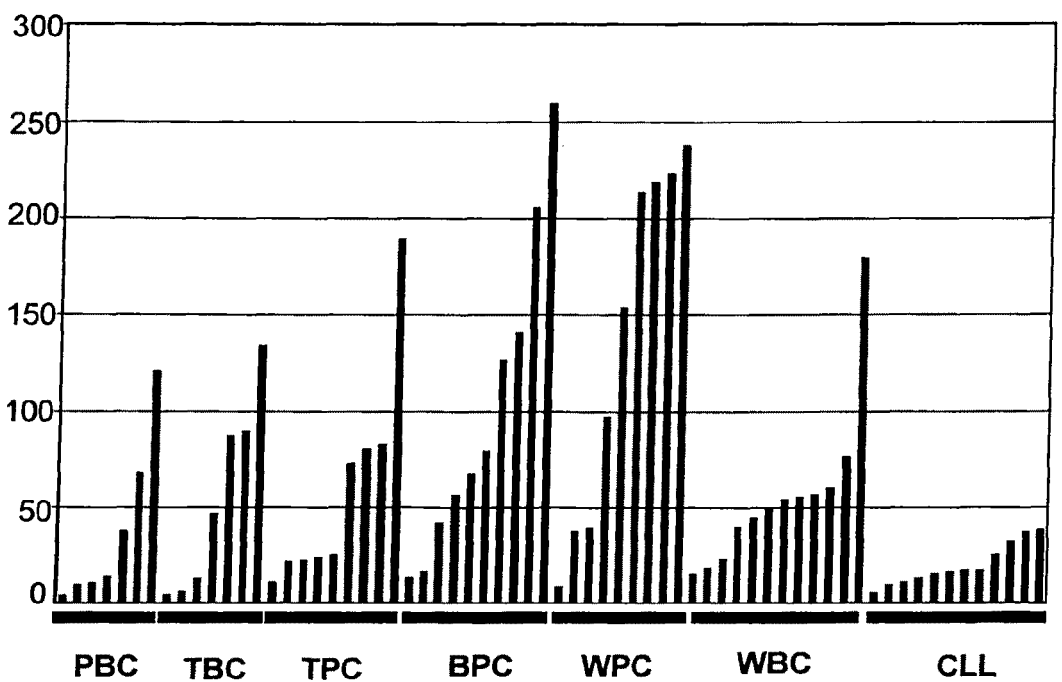
FIG. 11 shows DKK-1 was not expressed in normal B cells or plasma cells. PBC, TBC, tonsil B cells; TPC, tonsil plasma cells; BPC, bone marrow plasma cells; WPC, WBC, CLL.
Figure 12:
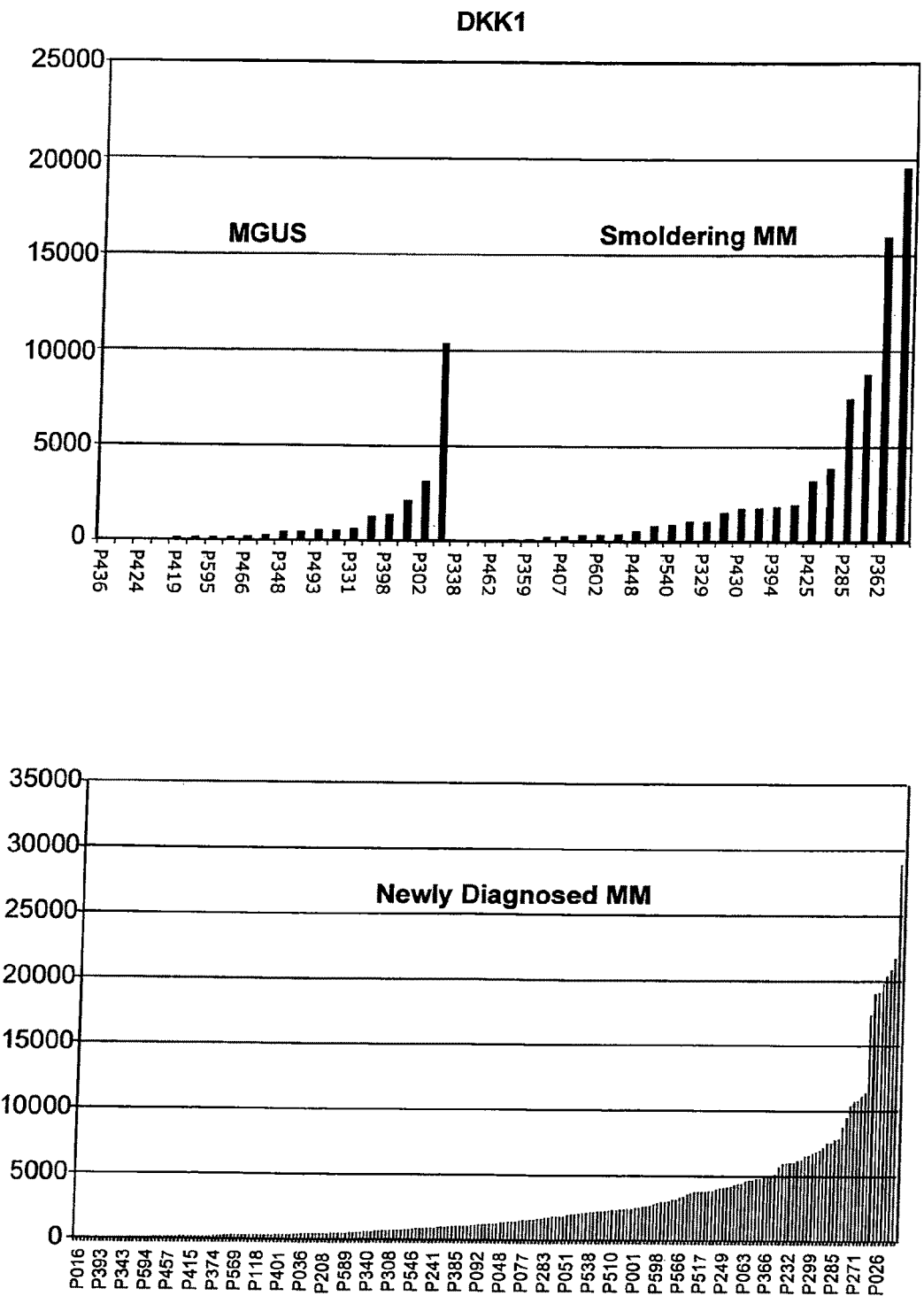
FIG. 12 shows DKK-1 expression in monoclonal gammopathy of undetermined significance (MGUS) was low relative to smoldering multiple myeloma (SMM) and newly diagnosed multiple myeloma (MM).

PTTG1 (securin) involved in chromosome segregation was identified by WRS as the most significant discriminating gene ($P=4\times10^{-6}$). It was called present in 11% of no lytic lesion group but present in 50% of the lytic lesion group (FIG. 4). Other notable genes in the WRS test included the TSC-22 homologue DSIPI which was expressed at lower levels in lytic lesion group ($P=3\times10^{-5}$). DSIPI is also down-regulated in 12 of 12 multiple myeloma plasma cells after ex-vivo co-culture with osteoclasts.

In addition, 4 so called "spike genes" were identified that were more frequently found in lytic lesion group versus no lytic lesion group (p<0.05): IL6, showing spikes in 0/28 no lytic lesion group and 7/47 lytic lesion group (p=0.032); Osteonidogen (NID2) showing spikes in 0/28 no lytic lesion group and 7/47 lytic lesion group (p=0.032); Regulator of G protein signaling (RGS13) showing spikes in 1/28 no lytic lesion group and 11/47 lytic lesion group (p=0.023); and pyromidinergic receptor P2Y (P2RY6) showing spikes in 1/28 no lytic lesion group and 1/47 lytic lesion group p=0.023).

Thus, these data suggest that gene expression patterns may be linked to bone disease. In addition to being potentially useful as predictors of the emergence of lytic bone disease and conversion from monoclonal gammopathy of undetermined significance to overt multiple myeloma, they may also identify targets for potential intervention.

EXAMPLE 10

DDK1 and FRZB Tend to be Expressed at Higher Levels in Plasma Cells from Focal Lesions than from Random Marrow Given the relationship of DKK-1 and FRZB to lytic lesions, DKK-1 and FRZB expressions were compared in plasma cells derived from random bone marrow aspirates of the iliac crest with those derived by CT-guided fine needle aspiration of focal lesions of the spine. These results showed significantly higher levels of expression in plasma cells from focal lesions.

EXAMPLE 11

Figure 20:
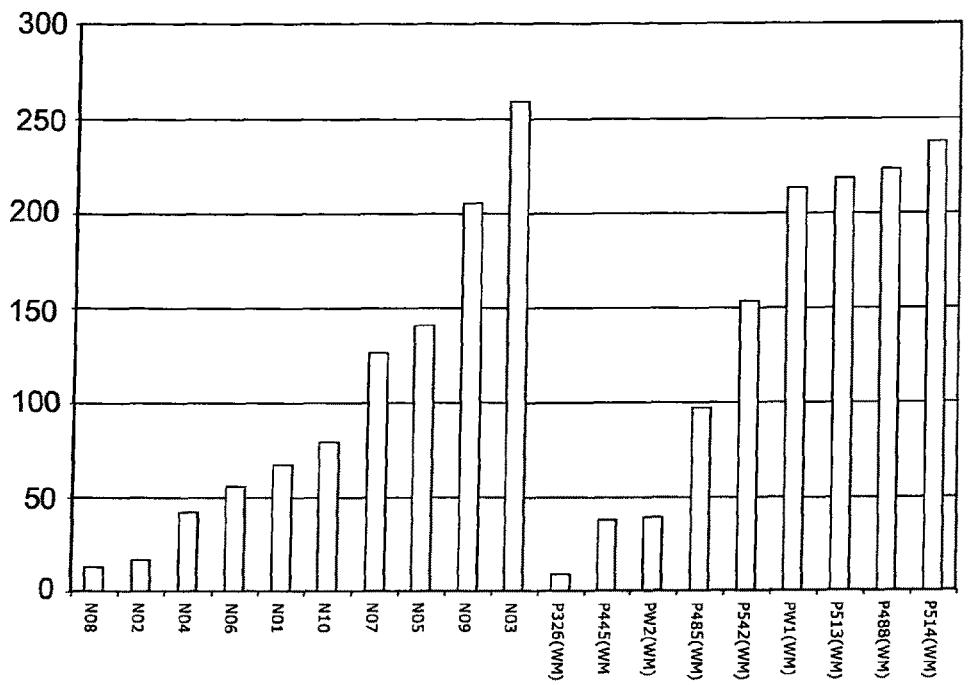
FIG. 20 shows DKK-1 was not expressed in plasma cells from Waldenstrom's macroglobulinemia.
Figure 21:
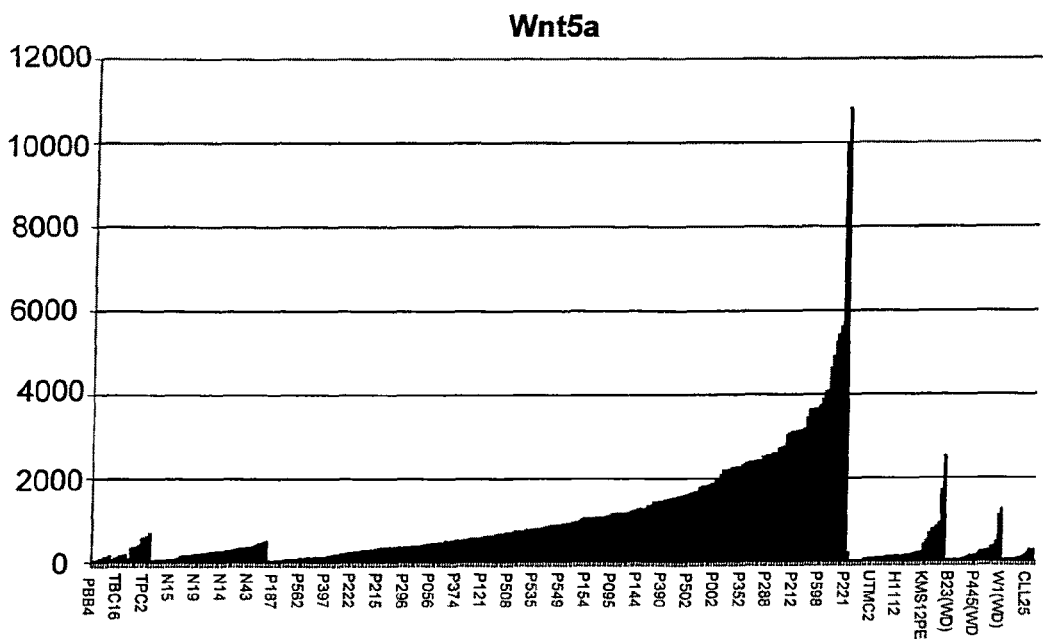
FIG. 21 shows WNT5A was elevated in newly diagnosed multiple myeloma.
Figure 22:
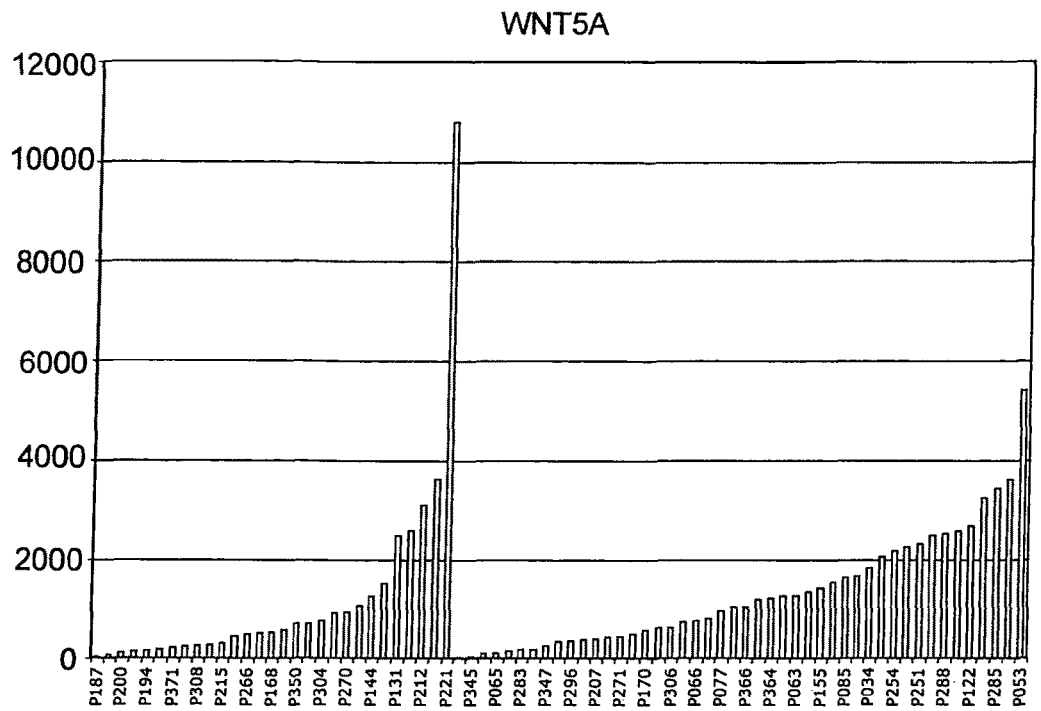
FIG. 22 shows WNT5A tends to be higher in multiple myeloma with lytic lesions.
Figure 23:
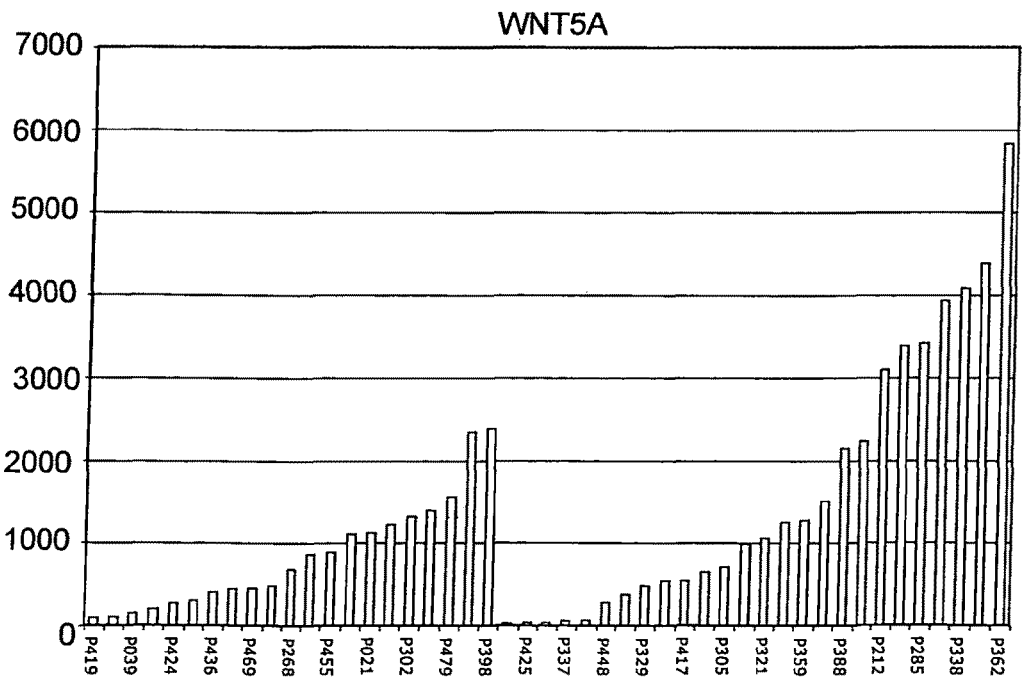
FIG. 23 shows WNT5A was also elevated in monoclonal gammopathy of undetermined significance (MGUS) and smoldering multiple myeloma (SMM).
Figure 24:
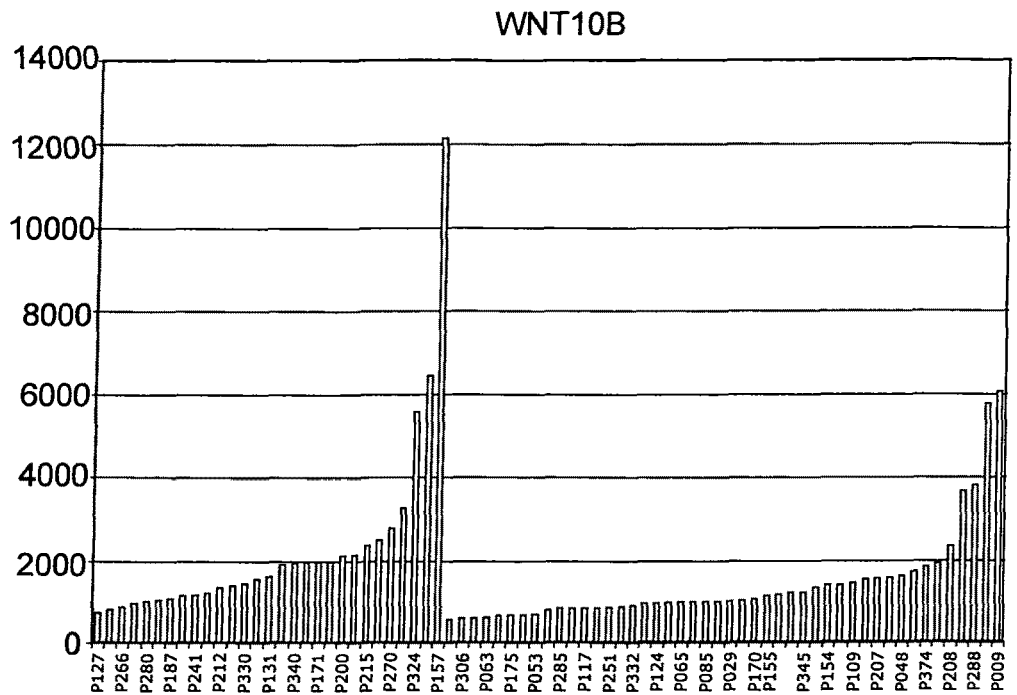
FIG. 24 shows WNT10B tends to be lower in multiple myeloma with lytic lesions.
Figure 25:
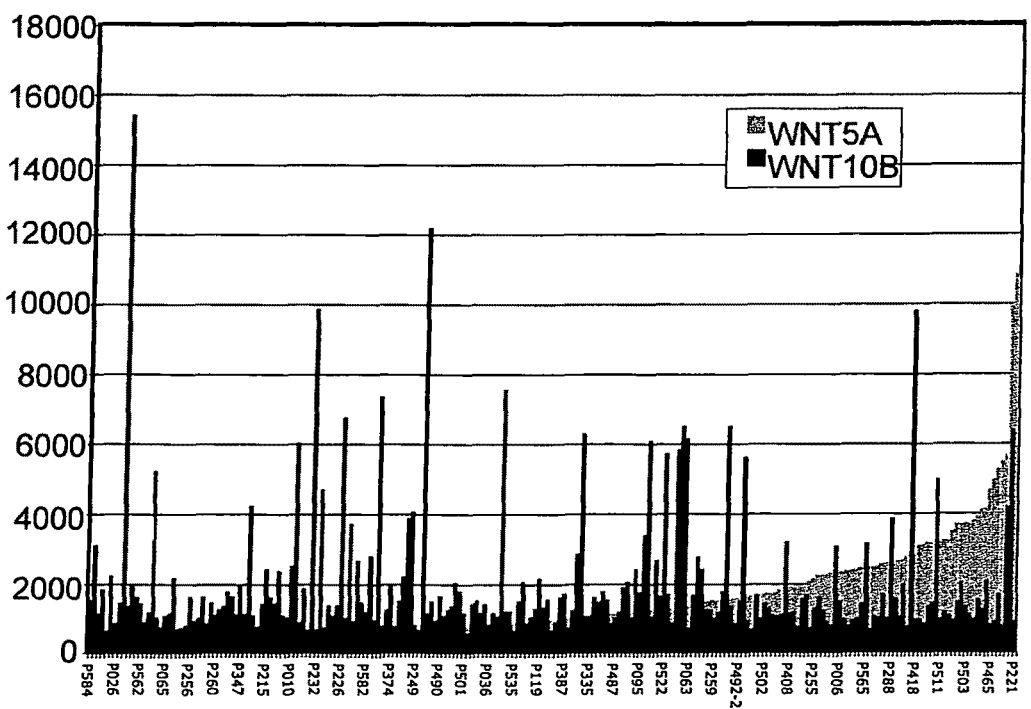
FIG. 25 shows WNT5A and WNT10B tend to be inversely correlated. Black bar: WNT10B; gray bar: WNT5A.
Figure 26:
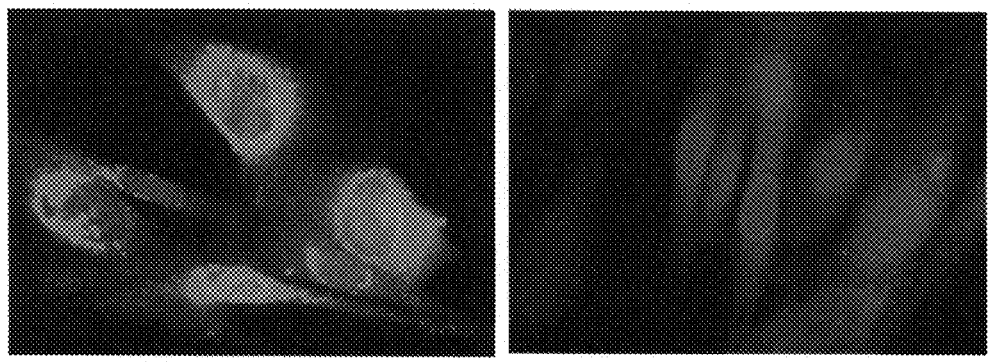
FIG. 26 shows DKK-1 was present in an SK-LMS cell line.
Figure 27:
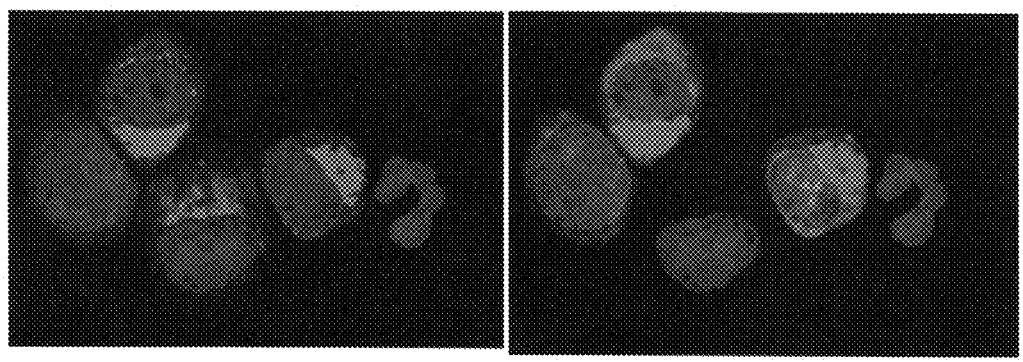
FIG. 27 shows primary multiple myeloma synthesized DKK-1 protein.
Figure 28:
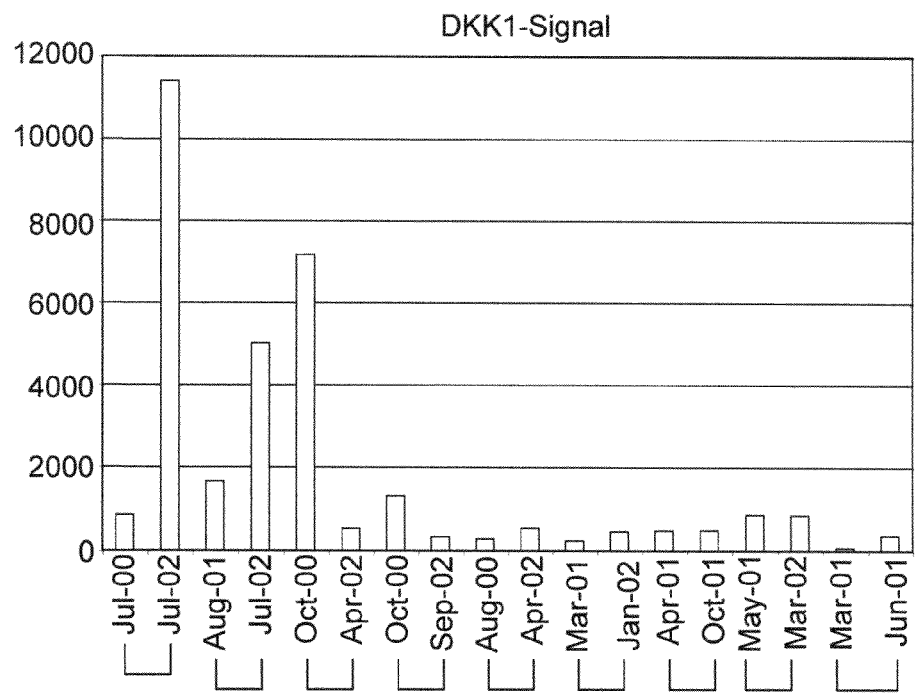
FIG. 28 shows low DKK-J expression in relapsed and primary refractory multiple myeloma.

DKK-1 and FRZB are not Expressed in Plasma Cells from Waldenstrom's Macroglobulinemia Waldenstrom's macroglobulinemia is a rare plasma cell dyscrasia characterized by a monoclonal IgM paraproteinemia and lymphoplasmacytic infiltration of bone marrow, lymph nodes and spleen. Its clinical presentation is variable as is the clinical course, yet unlike multiple myeloma, bone lesions are rare. Although global gene expression profiling of CD138-enriched bone marrow plasma cells from 10 cases of Waldenstrom's Macroglobulinemia reveled gross abnormalities, these cells, like normal bone marrow plasma cells, lack expression of FRZB and DKK (FIG. 20).

EXAMPLE 12

FRZB and Endothelin Receptor B Are Correlated With DKK-1

Figure 31:
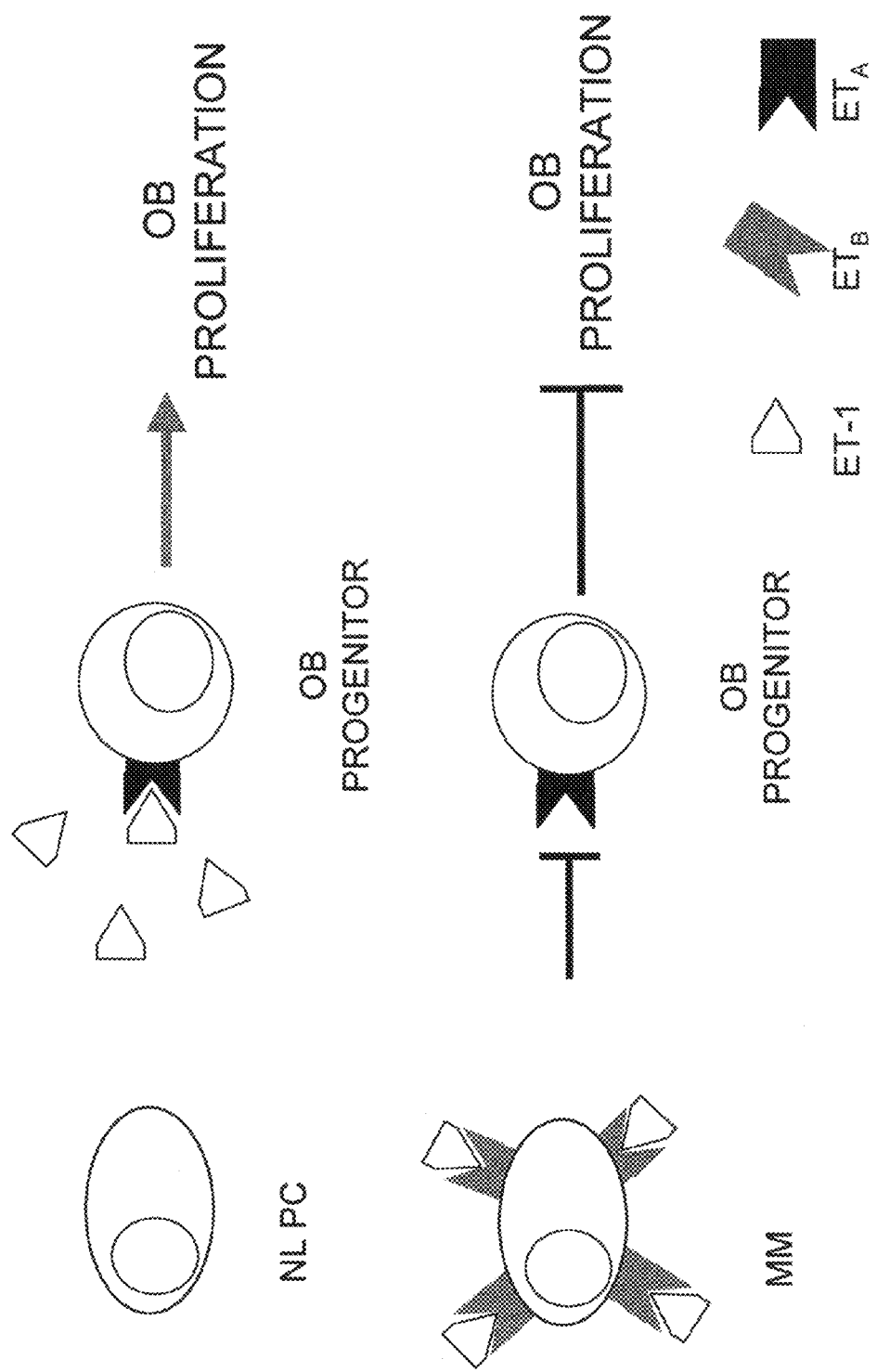
FIG. 31 shows the involvement of endothelin receptor B in bone formation.

Endothelin 1 is a 21 amino acids vasoconstrictor. Two receptors for endothelin, receptors A and B, have been identified. Breast and prostate cancer cells can produce endothelin 1, and increased concentrations of endothelin 1 and endothelin receptor A have been found in advanced prostate cancer with bone metastases. Breast cancer cells that produced endothelin 1 caused osteoblastic metastases in female mice. Conditioned media and exogenous endothelin 1 stimulated osteoblasts proliferation and new bone formation in mouse calvariae cultures (FIG. 31). These results suggest that endothelin is linked to bone formation.

Figure 29:
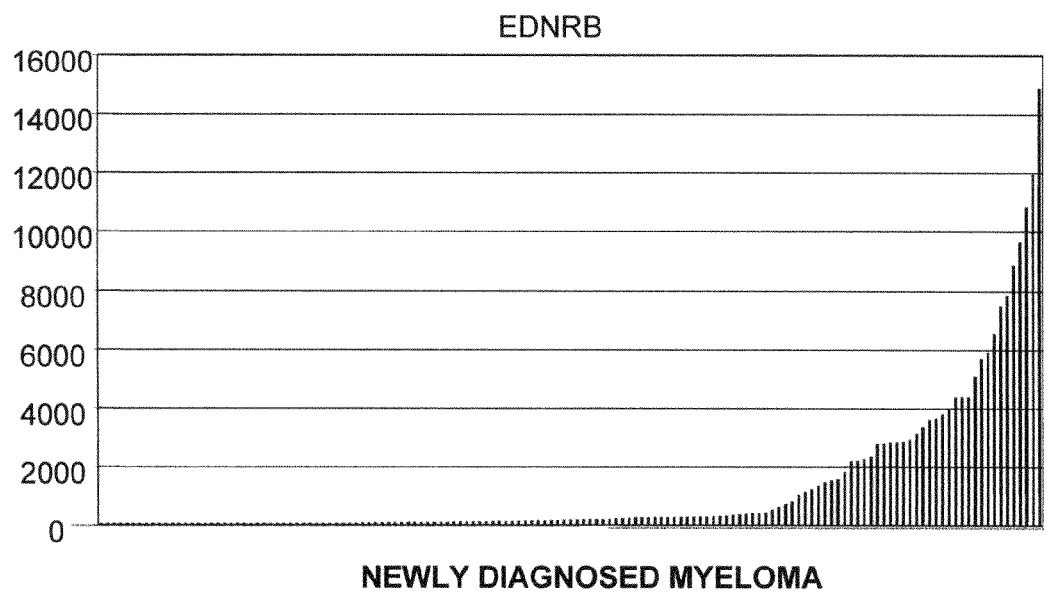
FIG. 29 shows endothelin receptor B was a "spike" gene in one third of newly diagnosed multiple myeloma.
Figure 30:
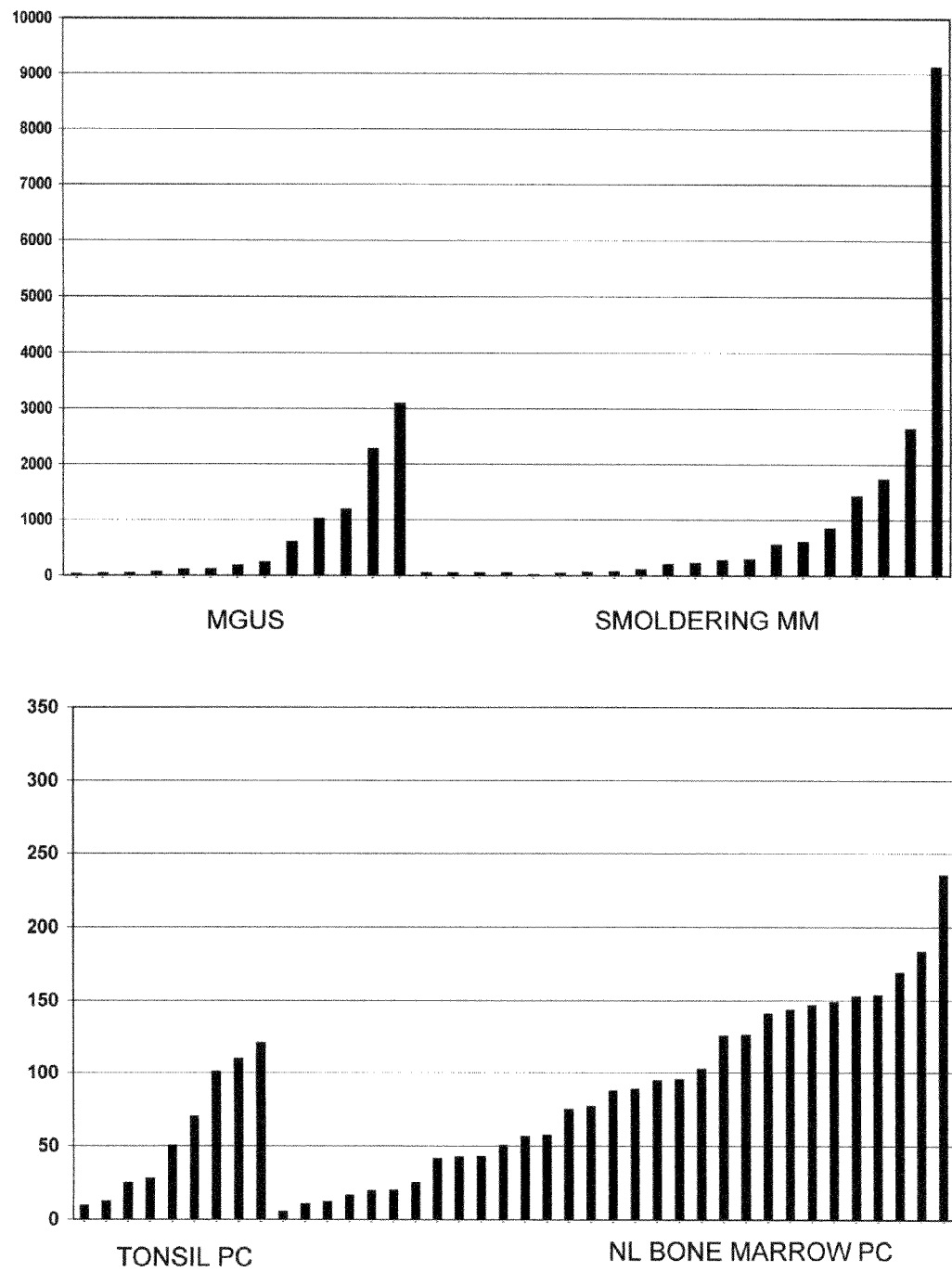
FIG. 30 shows the expression of endothelin receptor B in monoclonal gammopathy of undetermined significance (MGUS) and smoldering multiple myeloma. Normal plasma cells do not express endothelin receptor B.

Table 3 shows that the expression of endothelin receptor B (ENDRB) was correlated with that of DKK-1. Endothelin receptor B was a 'spike' gene in one third of newly diagnosed multiple myeloma (FIG. 29). Endothelin receptor B was also expressed in subsets of monoclonal gammopathy of undetermined significance (MGUS) and smoldering multiple myeloma but not in normal plasma cells (FIG. 30).

TABLE 3

Correlation Between Endothelin Receptor B (EDNRB) and DKK-1

| Gene Symbol | Asymp. Significance (two-tailed) |
| --- | --- |
| DKK-1 | $6.35 \times 10^{-14}$ |
| FRZB | $6.59 \times 10^{-8}$ |
| EDNRB | 0.00014 |
| DKFZP564G202 | $4.83 \times 10^{-11}$ |
| IFI27 | $1.43 \times 10^{-6}$ |
| SLC13A3 | 0.00011 |
| CCND1 | 0.00010 |
| SYN47 | $4.27 \times 10^{-10}$ |
| PCDH9 | 0.00029 |

EXAMPLE 13

In Vivo Drug Treatment Upregulates DKK-1

Figure 15:
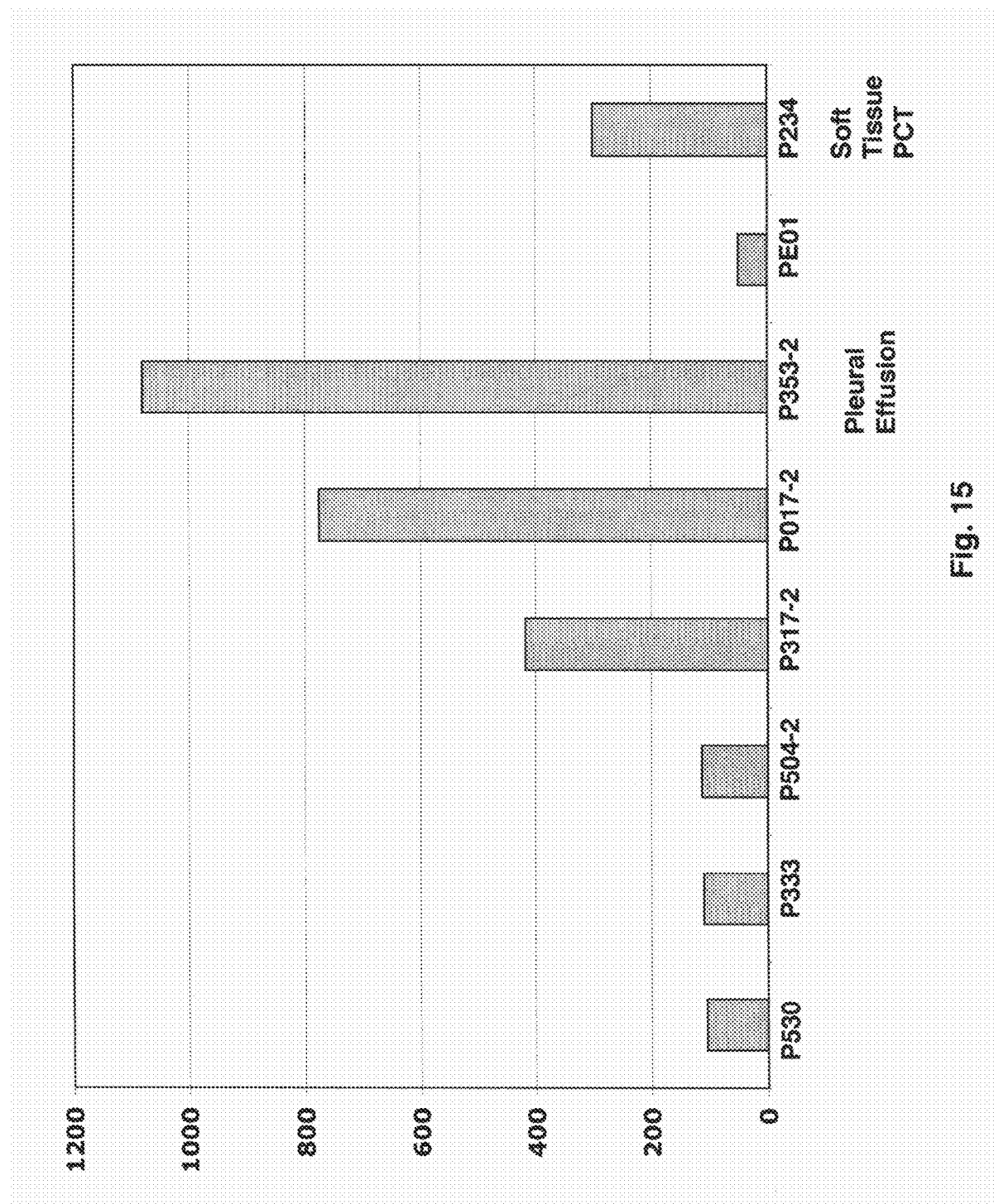
FIG. 15 shows low expression of DKK-1 in extramedullary disease.
Figure 17:
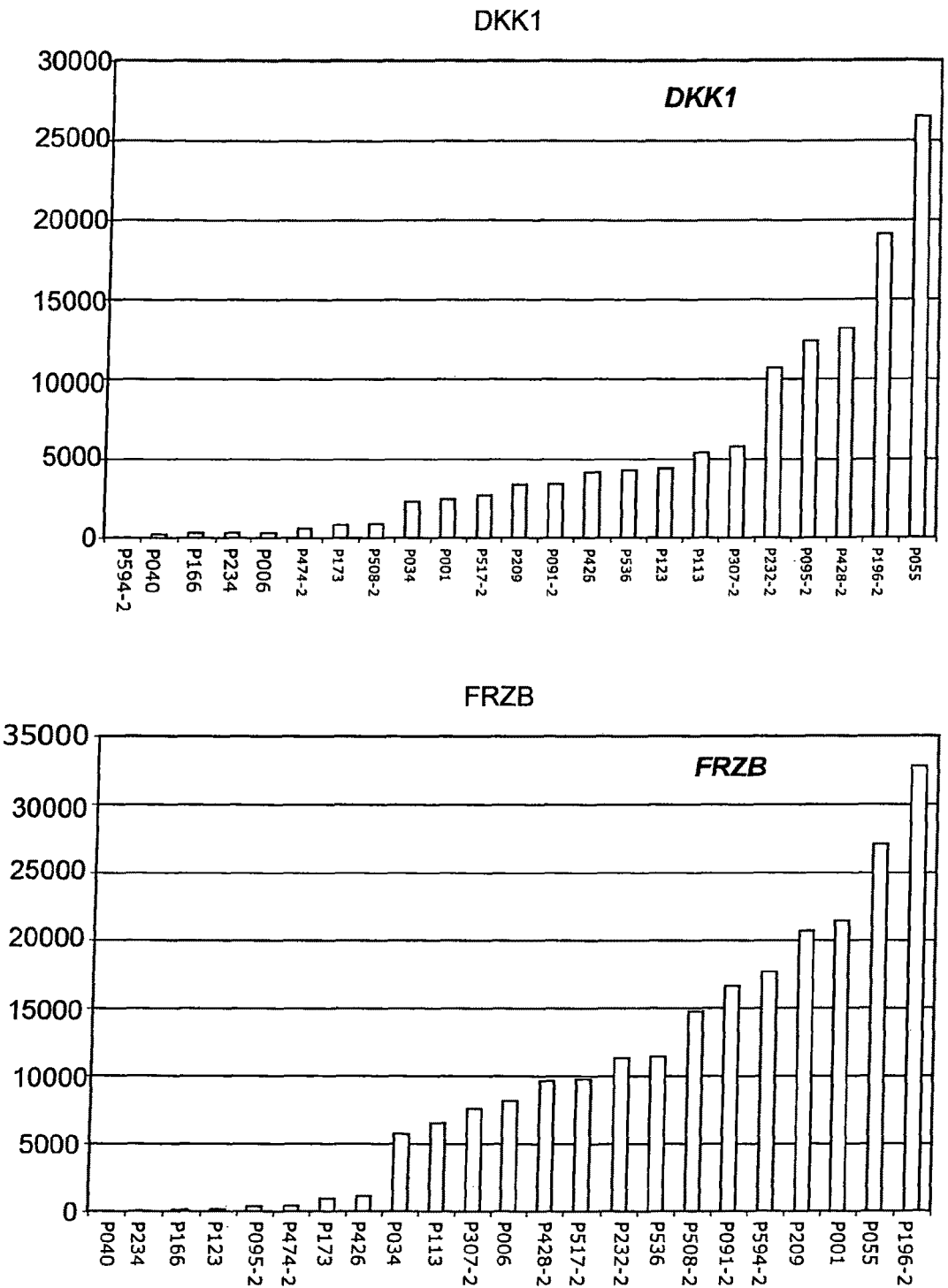
FIG. 17 shows the expression of DKK-1 and FRZB in fine needle aspirates of medullary PCT.
Figure 18:
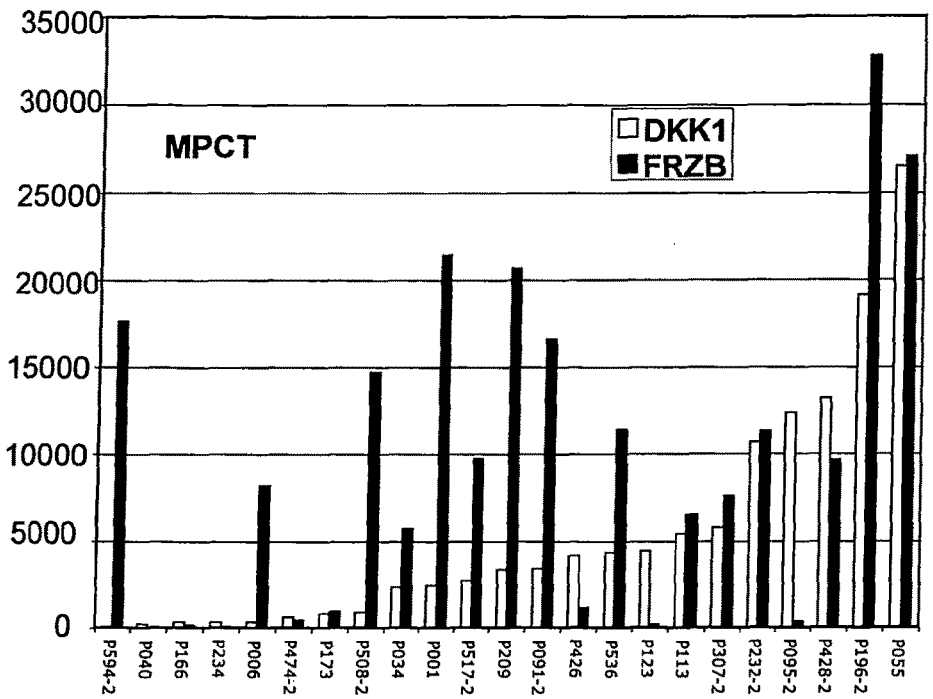
FIG. 18 shows high expression of DKK-1 and FRZB in medullary plasmacytoma.
Figure 19:
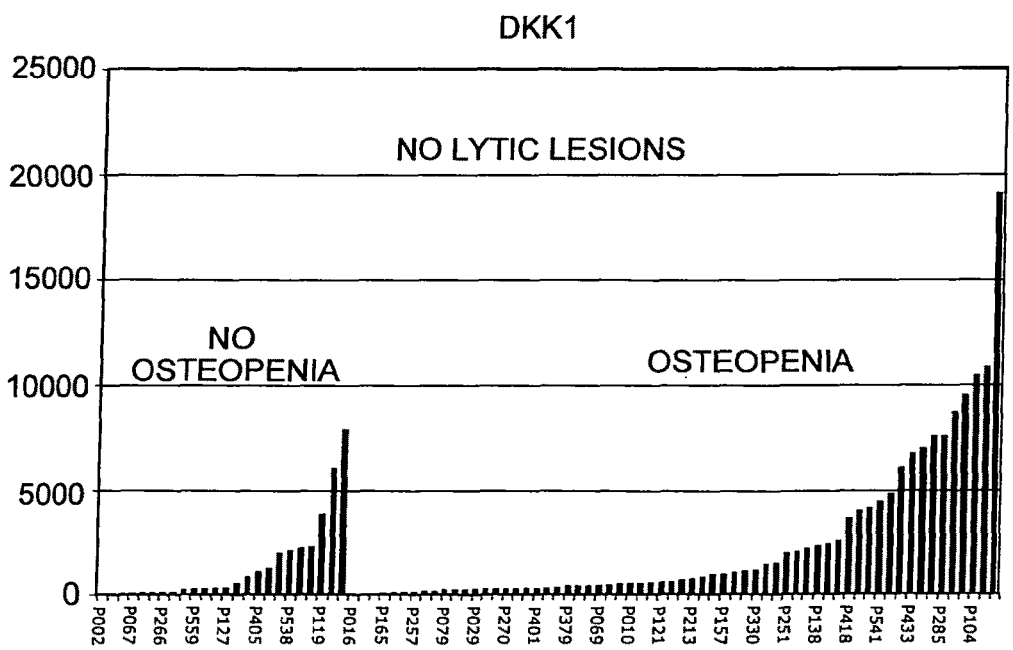
FIG. 19 shows higher expression of DKK-1 in multiple myeloma with osteopenia.
Figure 32:
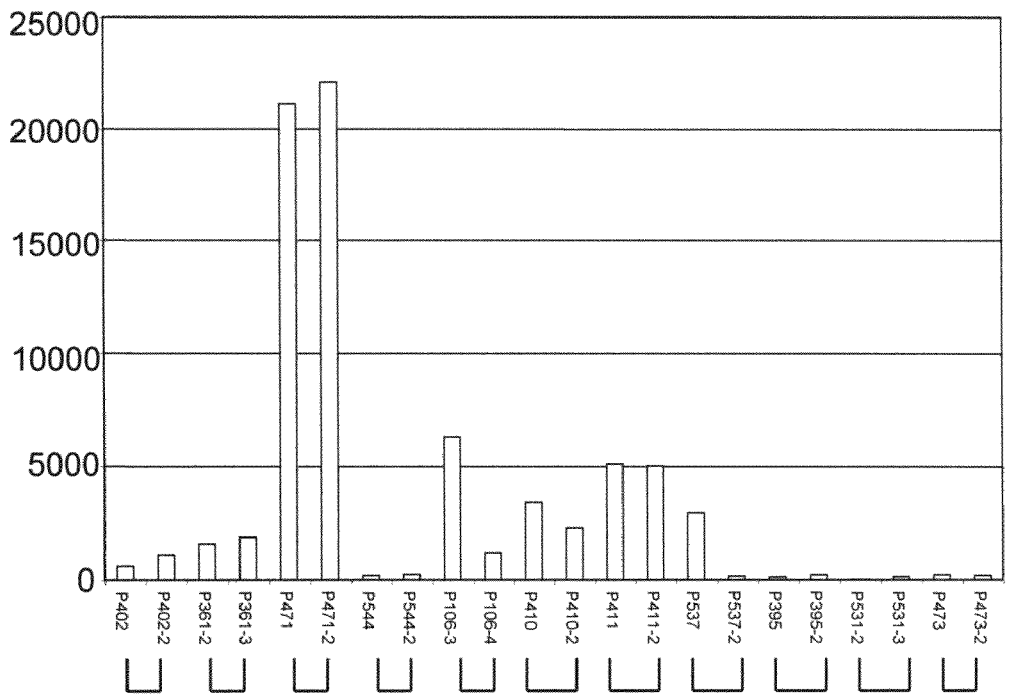
FIG. 32 shows DKK-1 expression after treatment with PS-341.
Figure 33:
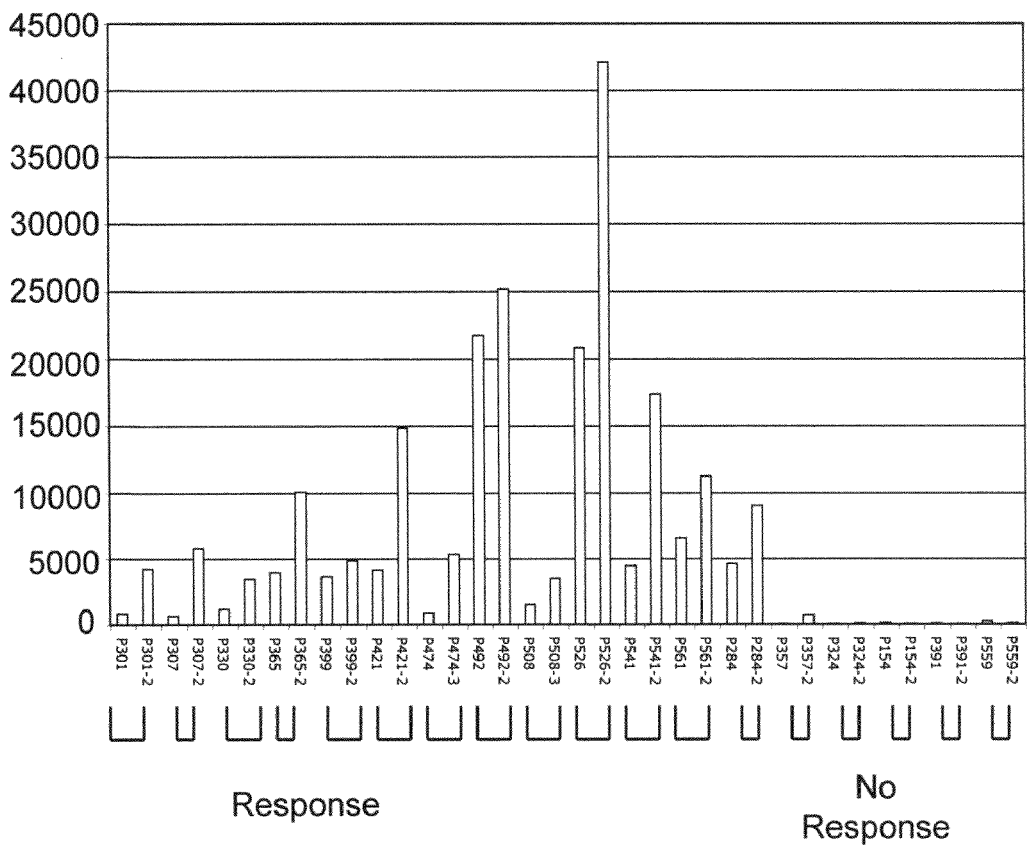
FIG. 33 shows DKK-1 expression after treatment with thalidomide in newly diagnosed multiple myeloma.
Figure 34:
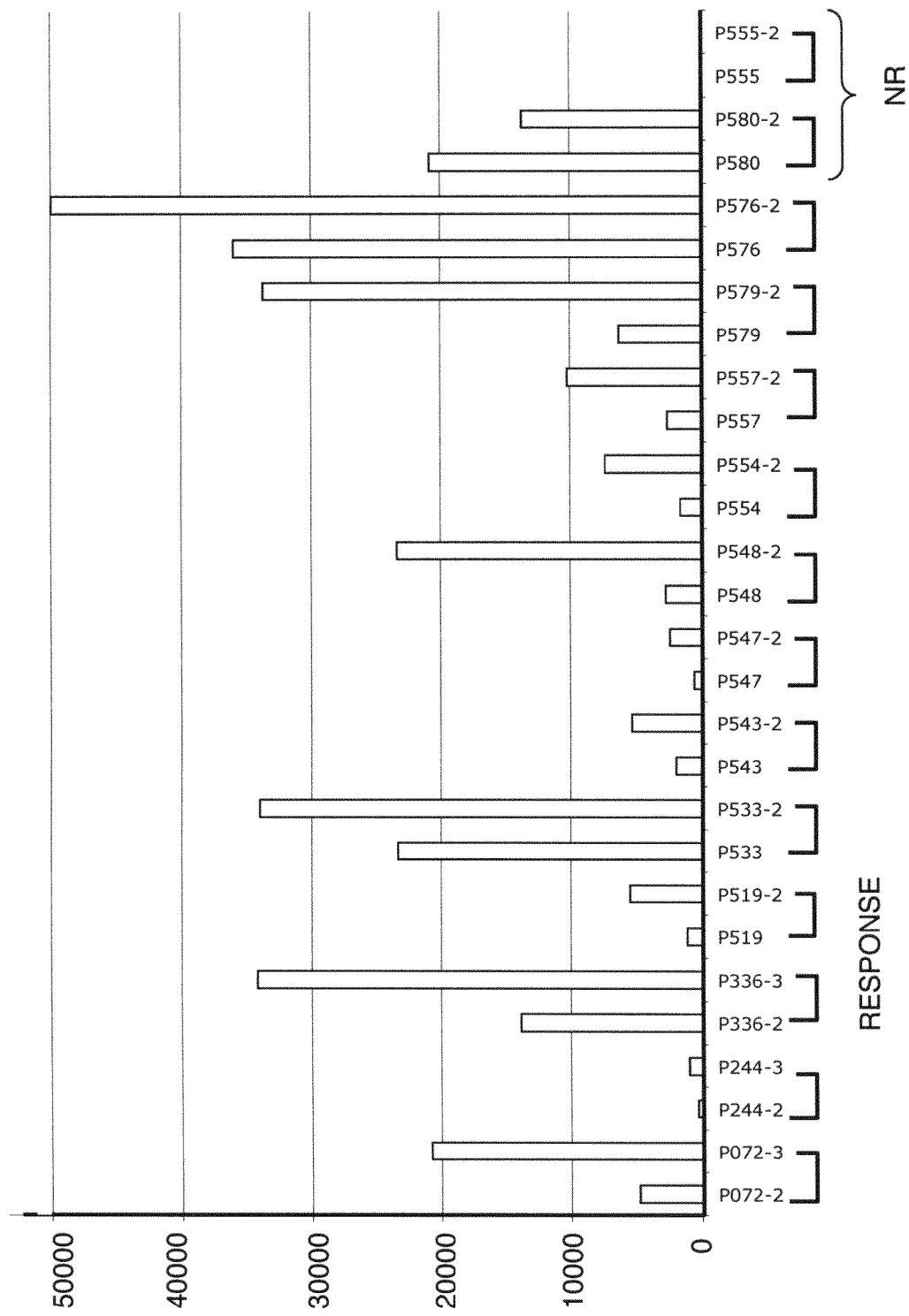
FIG. 34 shows DKK-1 expression after treatment with IMiD.
Figure 35:
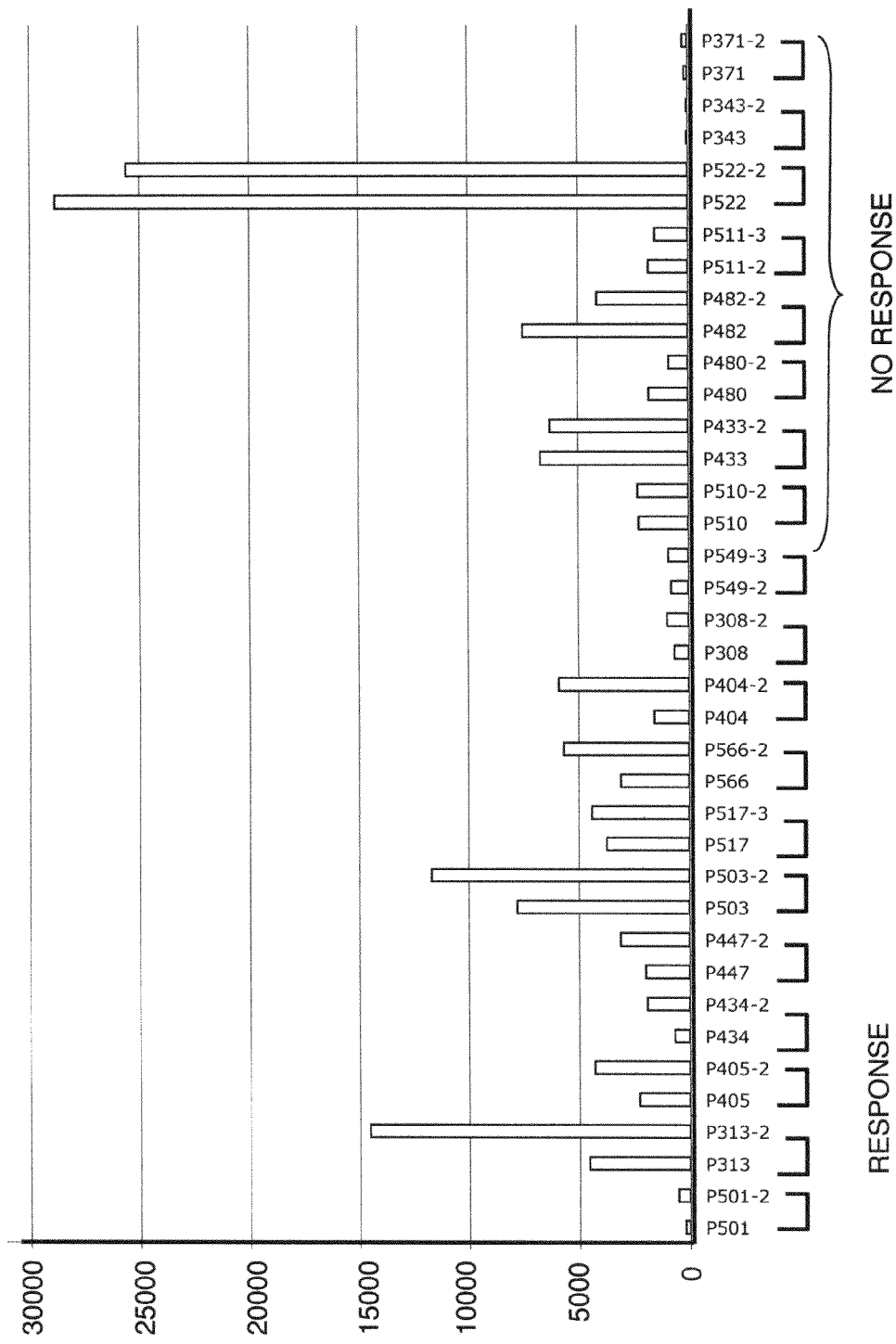
FIG. 35 shows DKK-1 expression after treatment with dexamethsone in newly diagnosed multiple myeloma.
Figure 36:
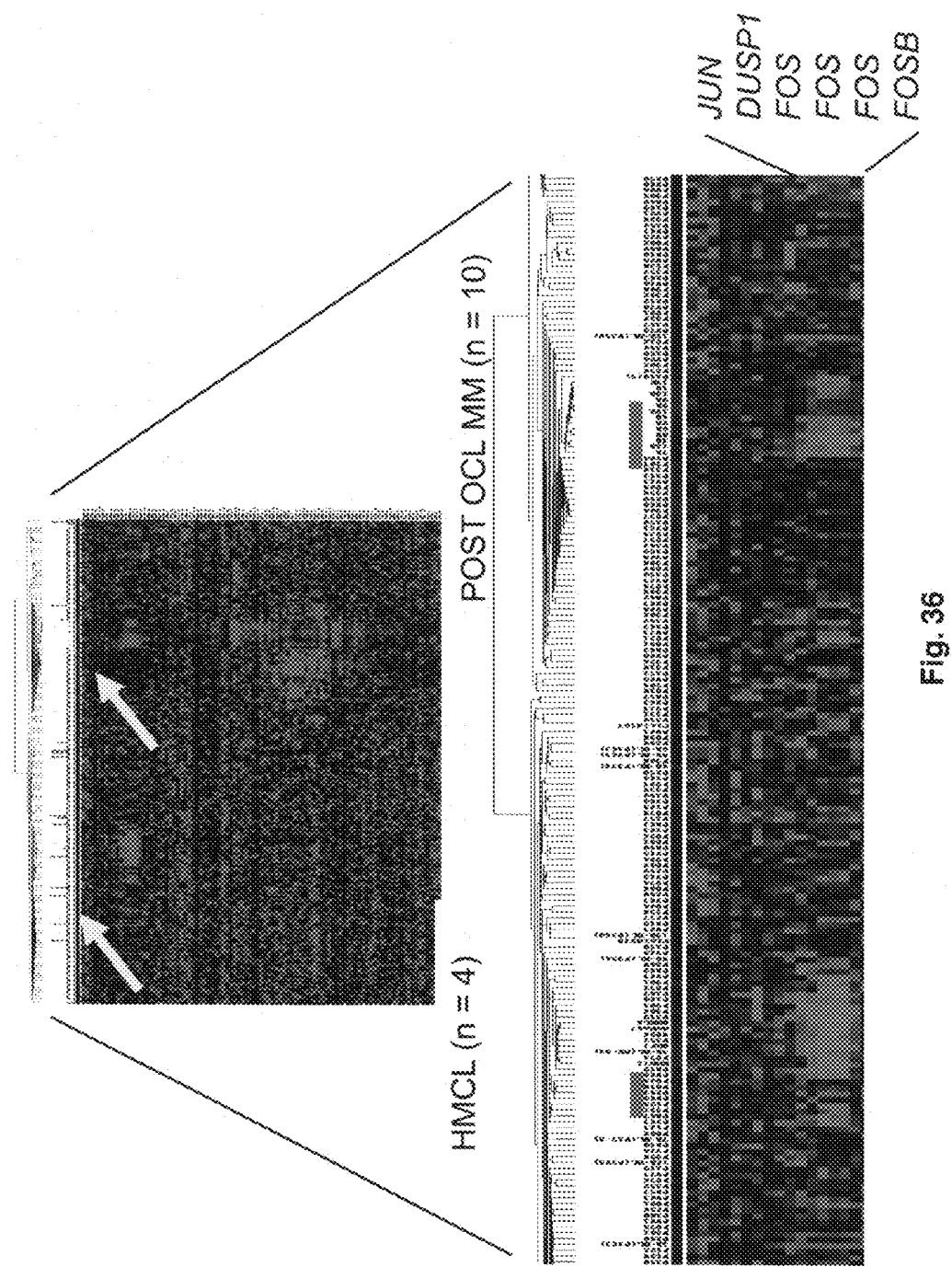
FIG. 36 shows downregulation of JUN and FOS in multiple myeloma cells after co-culture with osteoclasts.
Figure 37:
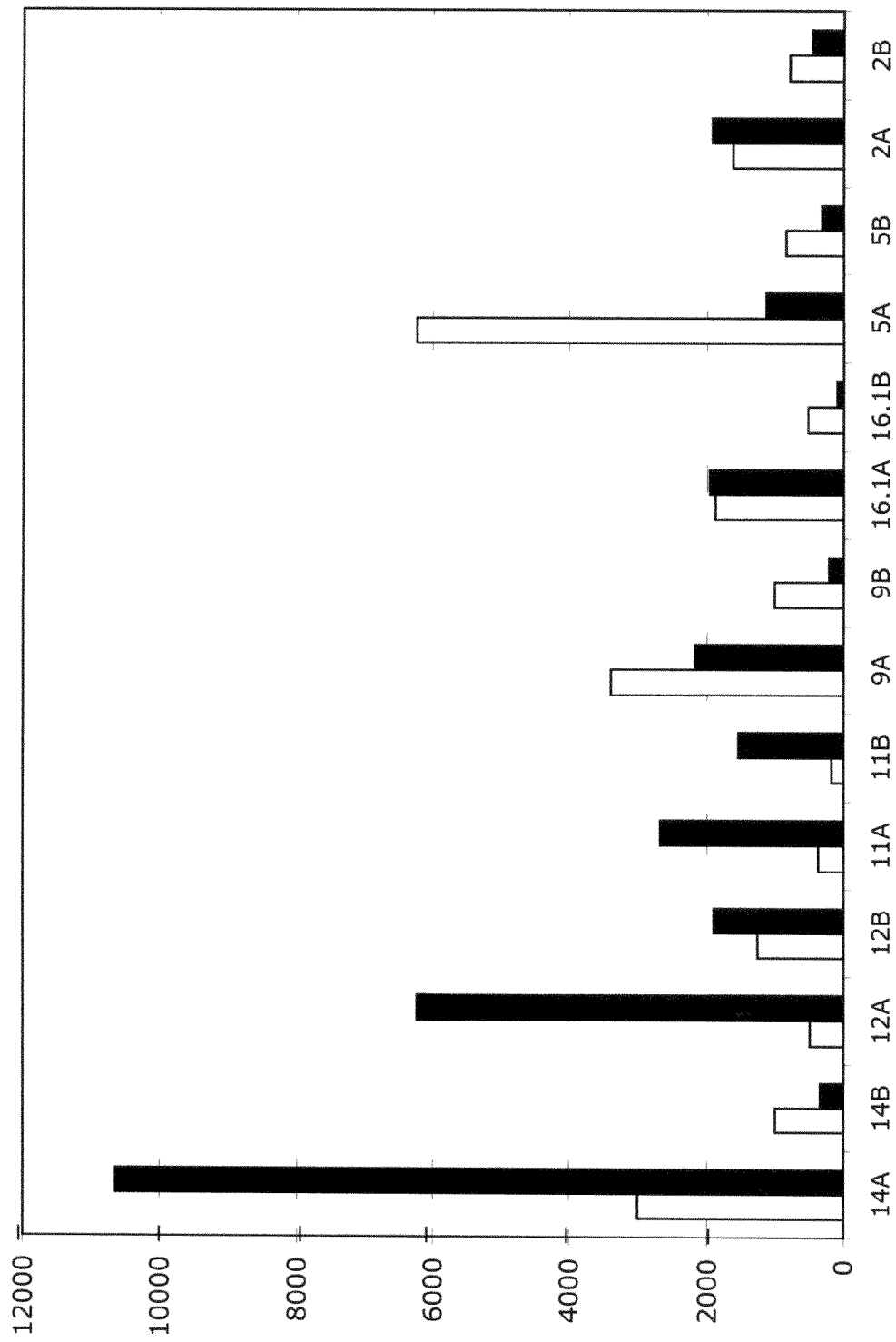
FIG. 37 shows JUN & DKK-1 downregulation in osteoclast co-culture.
Figure 38:
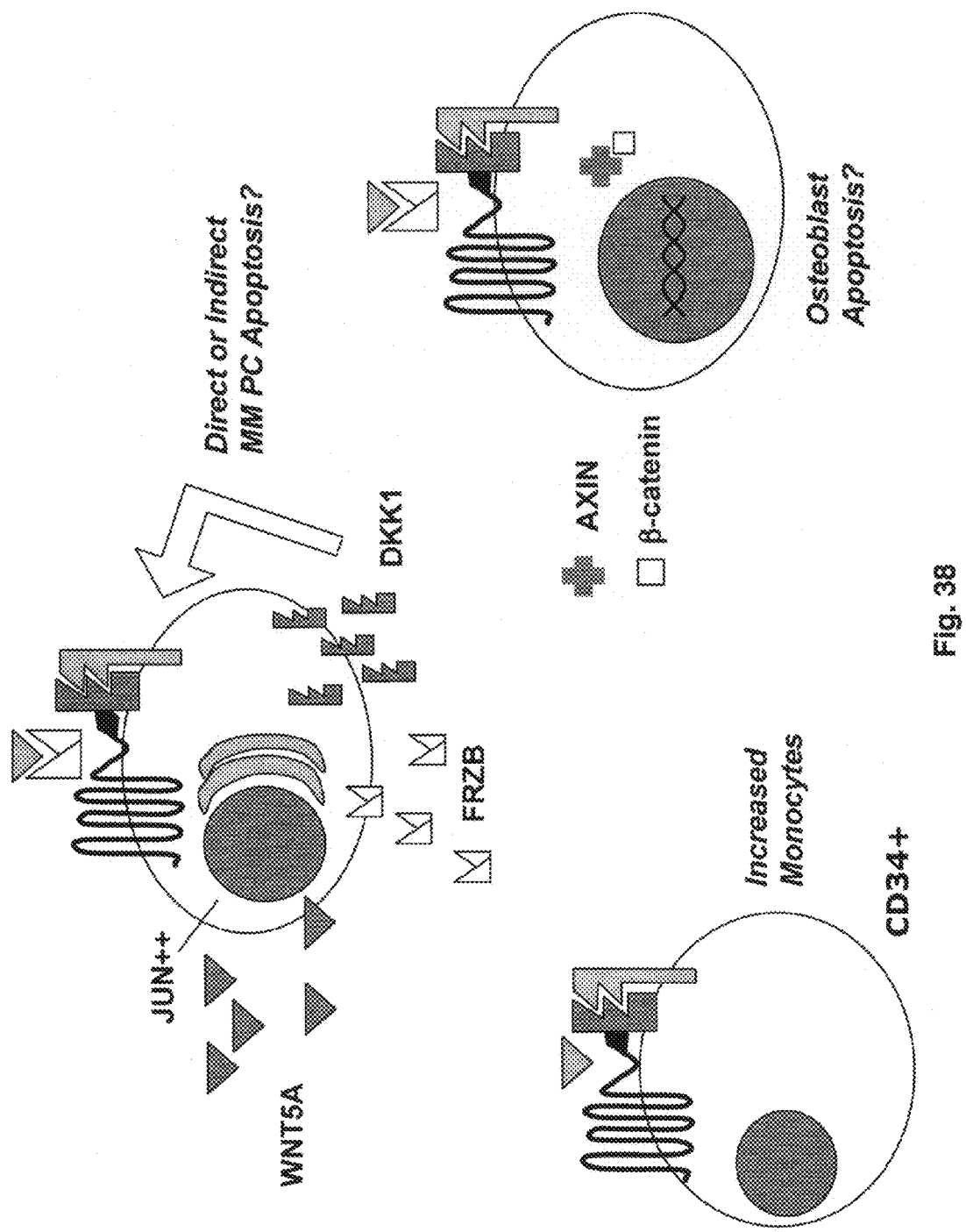
FIG. 38 shows WNT signaling in multiple myeloma bone disease.

DKK-1 expression is massively upregulated by UV irradiation and several other gentoxic stimuli. To see if multiple myeloma plasma cells also upregulate the genes in response to drugs used to treat this disease, gene expression profiling of multiple myeloma plasma cells was performed before and after 48 hour in vivo treatment with thalidomide (FIG. 33), ImiD (FIG. 34), PS-341 (FIG. 32), or dexamethasone (FIG. 35). These data showed that DKK-1 and FRZB expression could be massively upregulated in many cases and thus supporting a direct role of DKK-1 in triggering apoptosis of multiple myeloma plasma cells. It is interesting to note that a newly diagnosed patient who was primary refractory to all agents tested showed low levels of DKK-1 in initial prestudy tests and never showed increased expression of DKK-1 or FRZB after drug treatment, supporting a role for DKK-1 expression in promoting apoptosis of multiple myeloma plasma cells. In support of this notion, DKK-J and FRZB were expressed at low to undetectable levels in 30 HMCL and several cases of extramedullary disease (FIG. 15).

EXAMPLE 14

Co-Culture of Multiple Myeloma with Osteoclasts Results in Massive Downregulation of JUN, FOS, and DKK-1

The close relationship between myeloma cells and osteoclasts is expressed clinically by the association of debilitating lytic bone destruction with multiple myeloma. The development of lytic bone lesions is caused by the activation of osteoclasts through direct and indirect interactions with myeloma plasma cells. The critical role of osteoclasts in the survival and growth of myeloma cells and in sustaining the disease process has been gleaned clinically and demonstrated in vivo in experimental models such as the SCID-hu model for primary human myeloma.

In order to investigate the molecular consequences of multiple myeloma plasma cell/osteoclast interactions, an ex vivo system was developed in which CD138-enriched multiple myeloma plasma cells were co-cultured with osteoclasts derived from multiple myeloma peripheral blood stem cells or PBSCs and MNC from healthy donors. CD138-enriched multiple myeloma plasma cells co-cultured with human osteoclasts derived from peripheral blood stem cells from normal donors or multiple myeloma patients maintained their viability and proliferative activity as indicated by annexin V flow cytometry, BrdU labeling index and [$^3$H]TdR incorporation for as long as 50 days. Purity level of plasma cells before and after co-cultures was greater than 95% as determined by CD38/CD45 flow cytometry.

Microarray analyses of the expression of ~12,000 genes in 12 multiple myeloma plasma cells were performed before and after 4 day co-culture. Hierarchical cluster analysis of the 12 multiple myeloma plasma cells pairs and 150 newly diagnosed multiple myeloma plasma cells using 7,913 probes sets (genes) revealed that whereas the pre-co-culture samples were distributed amongst 3 major cluster groups, the post-co-culture samples clustered tightly together in 2 of the major branches. An analysis of the significant gene expression changes after co-culture showed that 95 probe sets (genes) changed 2- to 50-fold (77 up- and 18 down-regulated) in at least 8 of the 12 multiple myeloma plasma cells after co-culture. CD138-enriched plasma cells from 5 healthy donors showed identical shifts in many of the same genes, suggesting that multiple myeloma plasma cells do not exhibit altered responses to osteoclasts. However, normal plasma cells as opposed to their malignant counterparts did not survive in long term co-cultures with osteoclasts.

The most striking changes were in the up-regulation of the chemokines GRO1, GRO2, GRO3, SCYA2, SCYA8, SCYA18, and IL8. Other notable genes included the chemokine receptor CCR1, osteopontin (SPP1), the integrins ITGB2 and ITGB5, matrix metalloproteinase 9 (MMP9), cathepsin K (CTSK) and cathepsin L (CTSL). Surprisingly, a large number of osteoclast-related genes were among the 77 up-regulated genes. The down-regulated genes included cyclin B (CCNB1), the cyclin B specific ubiquitin ligase UBE2C, the TSC-22 homologue DSIPI, and JUN, JUND, FOS, and FOSB.

Gene expression changes were also tested in 10 osteoclast cultured alone and after co-culture with multiple myeloma plasma cells. Twenty-four genes (14 up- and 10 down-regulated) changed 2- to 10-fold in at least 7 of 10 osteoclasts after co-culture. There were no significant differences in gene expression between multiple myeloma plasma cells cultured with osteoclasts derived from multiple myeloma patients or from healthy donors, suggesting that multiple myeloma osteoclasts are not qualitatively different than those derived from normal donors.

No significant changes in gene expression were observed when multiple myeloma plasma cells were cultured in media derived from a co-culture experiment, suggesting that contact is important. Given the low ratio of multiple myeloma plasma cells to osteoclasts in the co-culture experiments (1000:1), it is unlikely that all plasma cells can be in contact with the osteoclasts simultaneously. Thus, it is likely that some intercellular communication between multiple myeloma plasma cells in contact with osteoclasts and those other multiple myeloma plasma cells occurs.

It is known that osteoclasts play a major role in multiple myeloma bone disease as well as providing multiple myeloma with anti-apoptotic signals. Recent studies have shown that JUN directly regulates DKK-1 expression and that JUN and DKK-1 control apoptosis.

To determine if osteoclasts may prevent apoptosis of multiple myeloma plasma cells by modulating JUN and DKK-1, gene expression profiling was performed on purified plasma cells from 12 primary multiple myeloma cases before and after 48 hours of co-culture with in vitro derived osteoclasts. Multiple myeloma plasma cells in the co-culture had significantly higher long-term viability than cells cultured alone. Gene expression profiling of multiple myeloma plasma cells before and after osteoclast co-culture revealed that JUN, FOS, and FOSB were 3 of 40 genes down-regulated more than 2-fold in all cases (n=12/12). Hierarchical cluster analysis of HMCL and primary multiple myeloma cells with 95 genes significantly modulated in multiple myeloma plasma cells after co-culture revealed a striking similarity between HMCL, primary multiple myeloma co-cultured with osteoclasts and a subset of newly diagnosed multiple myeloma in that these cell types had relatively low levels of c-JUN and c-FOS.

Importantly, whereas primary multiple myeloma cells show a high degree of spontaneous apoptosis when cultured alone, multiple myeloma plasma cells cultured in the presence of osteoclasts can survive indefinitely. These data support a link between JUN and DKK-1 and also suggest that loss of JUN and DKK expression in multiple myeloma may be associated with disease progression as extramedulalary disease and HMCL, which are invariably derived from extramedullary disease, lack both JUN and DKK. It is interesting to speculate that one of the major influences of osteoclasts on multiple myeloma growth and behavior is to down-regulate JUN and DKK-1, which directly affects plasma cells apoptosis. Treatment of HMCL and primary multiple myeloma/osteoclasts co-cultures with DKK-1 is expected to result in apoptosis of multiple myeloma plasma cells. DKK-1 will likely have no effect on the osteoclasts, as these cells do not express the Wnt co-receptor LRP-5. Normal bone marrow derived plasma cells also do not express DKK-1 and may help explain their long-lived nature.

EXAMPLE 15

Synthesis of DKK1 Protein by Plasma Cells

Figure 39:
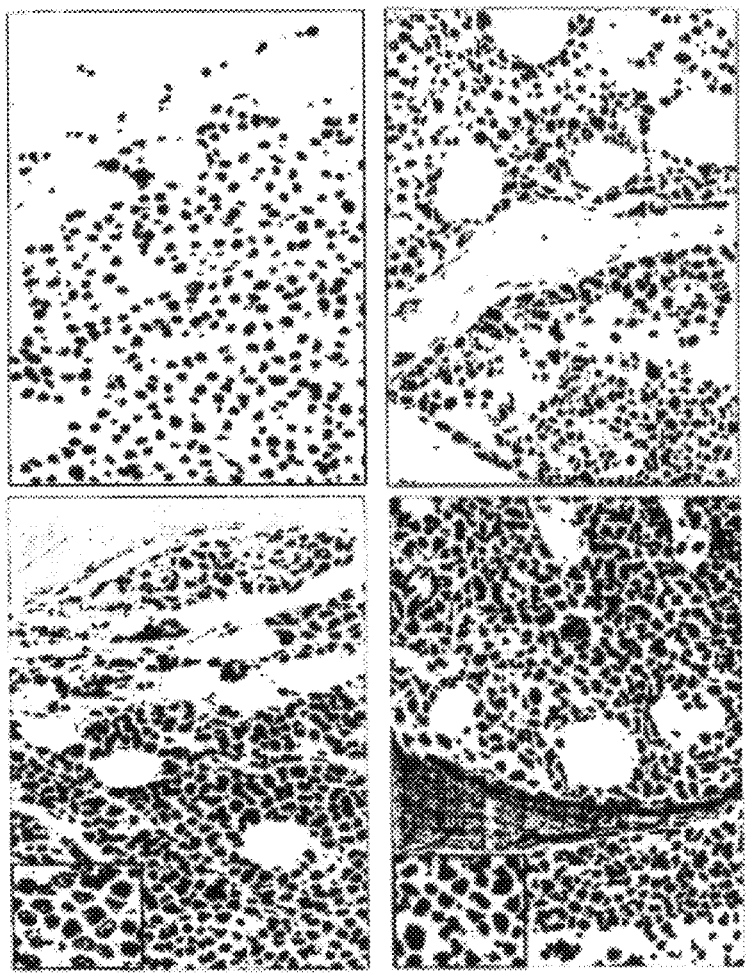
FIG. 39 shows overexpression of DKK1 in low grade myeloma with the loss of expression with disease progression. Expression of DKK1 was examined by immunohistochemistry of myeloma bone marrow biopsies. Serial sections (550× magnification) of bone marrow biopsies from myeloma patients with high (a-b) and low (c-d) DKK1 gene expression are presented. Slides are stained with H&E (a and c) or anti-DKK1 and secondary antibody (b and d). Use of secondary alone failed to stained cells (data not shown). Magnified images (1,200× magnification) are located in the upper left corner of each H&E image. Image a shows a myeloma with an interstitial pattern of involvement with plasma cells exhibiting low grade morphology with abundant cytoplasm and no apparent nucleoli. Image b reveals positive staining of plasma cells in a interstitial pattern with anti-DKK1 antibody that was greatest adjacent to bone. Image c shows a myeloma with nodular or alliterative pattern with plasma cells exhibiting high grade morphology with enlarged nuclei and prominent nucleoli. Image d reveals no positive staining of plasma with anti-DKK1 antibody.

Serial sections from bone marrow biopsies of 65 cases of multiple myeloma were stained for the presence of DKK1. The plasma cells in these cases contained DKK1 in a manner consistent with the gene expression data (FIG. 39). Similar experiments with biopsies from 5 normal donors failed to identify DKK1 in any cell. There was a strong tendency for DKK1 positive myelomas to have low-grade morphology (abundant cytoplasm without apparent nucleoli) with an interstitial growth pattern. This staining was found to be greatest in plasma cells adjacent to bone. DKK1 negative myelomas tend to bear high-grade morphology (enlarged nuclei and prominent nucleoli) with a nodular or obliterative growth pattern. In biopsies with an interstitial growth pattern, DKK1 was either present (in varying percentages of cells) or absent. In contrast, myelomas with the more aggressive nodular growth patterns DKK1 was uniformly absent. Importantly, in cases with both interstitial and nodular growth, the interstitial cells were positive and the nodular cells negative.

EXAMPLE 16

DKK1 Protein in Bone Marrow Plasma

Figure 40A:
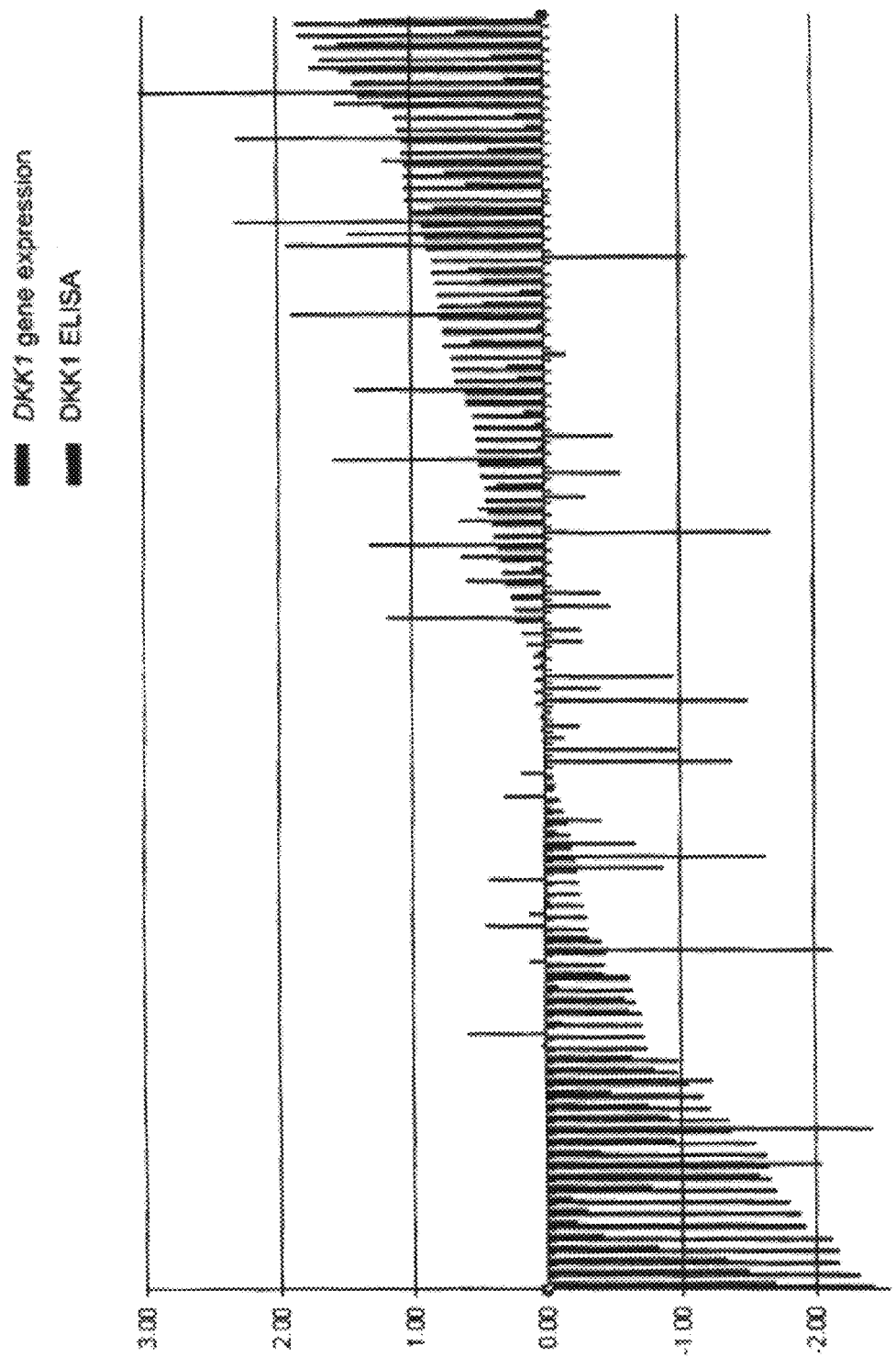

An enzyme-linked immunosorbent assay (ELISA) showed that the concentration of DKK1 protein in the bone marrow plasma from 107 of the 173 newly diagnosed multiple myeloma patients for which gene expression data was also available, was 24.02 ng/ml (S.D. 49.58). In contrast, DKK1 was 8.9 ng/ml (S.D. 4.2) in 14 normal healthy donors, 7.5 ng/ml (S.D. 4.5) in 14 cases of MGUS, and 5.5 ng/ml (S.D. 2.4) in 9 cases of Waldenstrom's macroglobulinemia. DKK1 gene expression and the level of DKK1 in the bone marrow plasma were positively correlated (r=0.65, P<0.001) in the 107 cases of myeloma (FIG. 40A). There was also a strong correlation between DKK1 protein levels in bone marrow plasma and peripheral blood plasma in 41 cases of myeloma in which both samples were taken simultaneously (r=0.57, P<0.001).

In 68 patients in whom both DKK1 protein levels in the bone marrow plasma and the presence of bone lesions were determined, DKK 1 protein in patients with 1+MRI and no x-ray lesions differ significantly compared to patients with no MRI and no x-ray lesions (median level: 20 ng/ml vs. 9 ng/ml; p=0.002), but does not differ significantly compared to patients with 1+MRI and 1+x-ray lesions (median level: 20 ng/ml vs. 14 ng/ml; p=0.36) (FIG. 40B, Table 2).

EXAMPLE 17

Effect of Bone Marrow Serum on Osteoblast Differentiation In Vitro

Figure 41A:
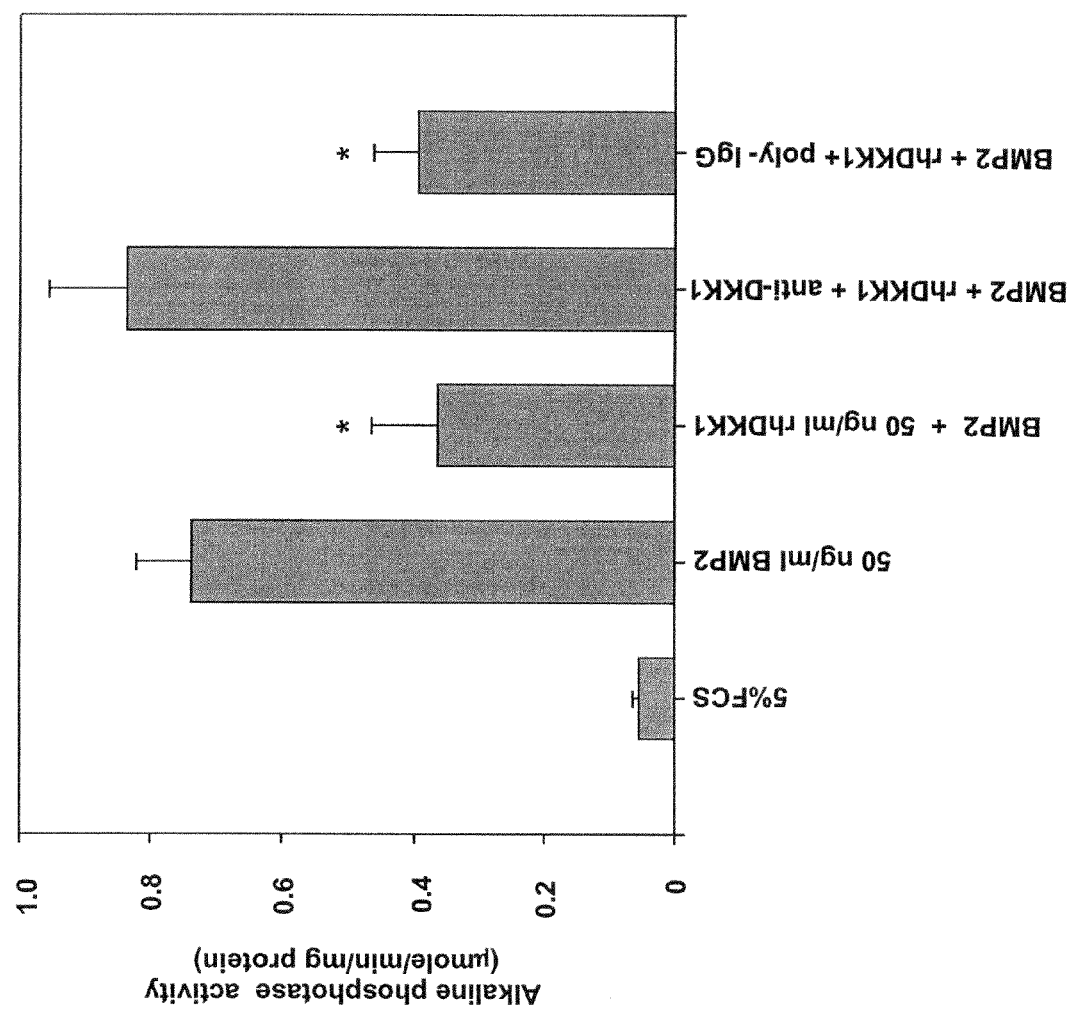

Bone morphogenic protein-2 can induce differentiation of the uncommitted mesenchymal progenitor cell line C2C12 (Katagiri, et al., 1994) into osteoblasts through a mechanism that involves Wnt/b-catenin signaling (Bain, et al., 2003; Roman-Roman, et al., 2002). Alkaline phosphatase, a specific marker of osteoblast differentiation, was undetectable in C2C12 cells grown in 5 percent fetal calf serum for 5 days (FIG. 41A). Treatment of C2C12 cells with 50 ng/ml of BMP-2 for 5 days induced them to produce alkaline phosphatase, whereas alkaline phosphatase was not produced by C2C12 cells that were concomitantly cultured with BMP-2 and 50 ng/ml recombinant human DKK1. This in vitro effect on alkaline phosphatase production was neutralized by a polyclonal anti-DKK1 antibody, but not by a non-specific polyclonal goat IgG. Bone marrow serum with a DKK1 concentration>12 ng/ml from five patients with myeloma inhibited the production of alkaline phosphatase by C2C12 cells treated with BMP-2, and this effect was reversed by the anti-DKK1 antibody, but not by non-specific IgG (FIG. 41B). By contrast, C2C12 cells treated with 50 ng/ml BMP-2 and 10 percent serum from the bone marrow of a normal donor induced the production of alkaline phosphatase by the cells (FIG. 41B).

EXAMPLE 18

The Functional Role of Canonical Wnt Signaling and DKK1 Inhibition of this Pathway in Bone Morphogenic Protein (BMP)-2-Induced Osteoblast Differentiation Expression of the DKK1 by multiple myeloma cells has been shown to correlate with lytic bone disease in multiple myeloma. Furthermore, as discussed supra, it was observed that alkaline phosphatase production was inhibited in presence of recombinant human DKK1. Hence, the present invention further investigated the mechanism by which DKK 1 contributed to this process.

Cells and Cell Culture

Mouse pluripotent mesenchymal precursor cell line C2C12 and the human osteoblast cell line hFOB 1.19 were purchased from America Type Culture Collection (Manassas, Va.). C2C12, MG63, Saos-2, and 293T cells were cultured in Dulbecco's Modified Eagle Medium (DMEM) (Invitrogen, Carlsbad, Calif.) containing 10% heat-inactivated FBS, penicillin (100 U/ml), streptomycin (100 mg/ml), and 4 mM L-glutamine. Cells were maintained at 37° C. and humidified with 95% air and 5% $CO_2$ for cell culture. hFOB 1.19 was cultured in a 1:1 mixture of Ham's F12 and DMEM with 10% FBS in the presence of 0.3 mg/ml G418.

Constructs and Transfectants

To generate dominant negative (DN)-b-catenin stable clones, C2C12 cells were transfected with pcDNA4 vector or a vector containing DN-beta-catenin cDNA (Boyden et al., 2002) using lipofectimine (Invitrogen) following manufacturer's instructions. After transfection, stable clones were generated by growing the cells in DMEM containing 10% FBS in the presence of Neocin (1 mg/ml) for two weeks. Stable Dkk1 and Dkk2 expressing clones generated in C2C12 and OPM-2 cells were previously described (Qiang et al., 2003).

Preparation of Conditioned Medium

Conditioned medium (CM) containing Wnt3a, Dkk1, Dkk2 and or appropriate control constructs was prepared as previously described (Qiang et al., 2003). Dkk1 and Dkk2 proteins in CM were detected by immunoblotting using anti-V5 (explain what anti-V5 is specific for)) and anti-Dkk1 antibodies by ELISA. The supernatant from culture medium was concentrated five-fold by using a YM-30 column (Qiang et al., 2002). Dkk1 levels in bone marrow plasma from MM patients was detected by ELISA.

Immunoblotting Analysis

Cells were incubated in MEM, Wnt3a CM, control CM, or with recombinant Wnt3a for indicated times. For inhibition studies, cells were pretreated with purified recombinant Dkk1 at indicated concentrations or Dkk1 CM, Dkk2 CM, or bone marrow plasma with low or high concentrations of Dkk1 protein for one hour. Following treatment, cells were lysed as described (Qiang et al., 2002). Cell lysates were separated by SDS-PAGE and transferred to Immobilon polyvinylidene difluoride membranes (Millipore, Bedford, Mass.). Immunoblotting was performed using the indicated antibodies.

GST-E-Cadherin Binding Assay

The GST-E-cadherin binding assay was performed as described (Bafico et al., 1998). Briefly, the beta-catenin binding site of E-cadherin as a GST-fusion protein was purified using GST beads. GST-E-cadherin was used to precipitate uncomplexed b-catenin present in 500 ng of cell lysate. Precipitated b-catenin was detected by immunoblotting using a b-catenin monoclonal antibody. Non-phosphorylated b-catenin was detected with a monoclonal antibody specific for b-catenin dephosphorylated at residues of 27-37 (Alexis, San Diego, Calif.).

Enzyme-Linked Immunosorbent Assay

Microtiter plates were coated with 50 µl of anti-Dkk1 antibody (R&D Systems, Minneapolis, Minn.) according to manufacturer recommendations. Bone marrow plasma (1:50) in dilution buffer was added and incubated overnight at 4° C. Plates were washed and incubated with biotinylated goat anti-human Dkk1 IgG (R&D Systems, Minneapolis, Minn.) followed by streptavidin-horseradish peroxidase (Vector Laboratories), according to manufacturer recommendations.

Luciferase Reporter Gene Assay

Cells plated at $5 \times 10^4$ per well in a 12-well plate were transiently co-transfected with 1 mg/ml of either TOPflash, FOPflash (Korinek et al., 1997), or Cbfa-1-luc (kindly provided by Dr. Ying Zhang, NCI, NIH) and 50 ng of pSV-b-galactosidase vector to normalize for transfection efficiency using Lipofectamine according to manufacturer instructions (Invitrogen). Following transfection, cells were exposed to Wnt3a CM or control CM for 24 hr prior to luciferase assay. Luciferase activity was measured as previously described (Qiang et al., 2003).

Alkaline Phosphatase (ALP) Assay

Cells were cultured in DMEM with 2% horse serum including either BMP-2 (200 ng/ml), Wnt3a CM, BPM-2 plus Dkk1, or BMP-2 plus Wnt3a CM for 72 or 96 hr followed by lysis in 150 ml of lysis buffer (20 mM Tris HCl, pH 8 and 150 mM NaCl, 0.2% NP40). ALP activity was measured using ALP kit (Diagnostic Chemical Limited, Exton, Pa.) according to manufacturer instructions. Absorbance The of samples was determined with a Spectra Max340 Microplate Spectrophotometer (Molecular Devices, Sunnyvale, Calif.) at 402 nm. Cell lysates were analyzed for protein content with using the micro-BCA assay kit (Pierce, Rockford, Ill.).

RT-PCR Analysis

First strand cDNA synthesis was performed as previously described. (31) All PCR reactions began with a first cycle at 95° C. for 3 min and a final cycle at 72° C. for 10 minutes with an additional 35 cycles at 94° C./30 s, 60° C./45 s, 72° C./1 min. Primer sequences for the indicated human genes are as described (Qiang et al., 2003). Primers, including Fz (Table 4), TCF and Dkk (Table 5) were designed using a primer pair program in the MacVector (City) software based on gene sequences from the NIH Gene Bank (www.ncbi.nlm.nih.gov).

TABLE 4

Mouse Frizzled Oligonucleotide Primers for RT-PCR

| Primer | Orientation | Nucleotide Seq 5' to 3' | Nucleotide Position | SEQ ID NO |
|---|---|---|---|---|
| Fz1F | Sense | atgtgtatgtgc gtgtggaccg | 2530-2551 | 1 |
| Fz1R | Anti-sense | gggagatgctga aggaaatgacc | 2854-2832 | 2 |
| Fz2F | Sense | aaataggttggg ttggagggag | 3077-3098 | 3 |
| Fz2R | Anti-sense | aaacaggagaga cggttgagagcg | 3537-3514 | 4 |
| Fz3F | Sense | tattgaggagga tggaaccagtgc | 2286-2309 | 5 |
| Fz3R | Anti-sense | caaagcagtcac cacacatagagg | 2607-2584 | 6 |
| Fz4F | Sense | tagttggatgcc gatgaactgac tg | 1394-1417 | 7 |
| Fz4R | Anti-sense | ttcccctcttc tctctcttacc | 1865-1842 | 8 |
| Fz5F | Sense | acattcgccacc ttctggattg | 1568-1589 | 9 |
| Fz5R | Anti-sense | ttttggttgccc acatagcag | 2058-2038 | 10 |
| Fz6F | Sense | aatggacacttt tggcatccg | 635-655 | 11 |
| Fz6R | Anti-sense | ctctgggtatct gaatcgtctaa cg | 1001-977 | 12 |
| Fz7F | Sense | aaggggggaaact gcggtatg | 1843-1862 | 13 |
| Fz7R | Anti-sense | tctctctctctg ctggtctcaacc | 2181-2158 | 14 |
| Fz8F | Sense | tccatctggtgg gtaatcctgtc | 1225-1247 | 15 |
| Fz8R | Anti-sense | cggttgtgctgc tcatagaaaag | 1667-1645 | 16 |
| Fz9F | Sense | cgcccgattatc ttcctttctatg | 998-1021 | 17 |
| Fz9R | Anti-sense | tagcagagccca gtcagttcatc | 1371-1349 | 18 |
| Fz10F | Sense | ccaacaagaacg accccaactac | 528-550 | 19 |

TABLE 4-continued

Mouse Frizzled Oligonucleotide Primers for RT-PCR

| Primer | Orientation | Nucleotide Seq 5' to 3' | Nucleotide Position | SEQ ID NO |
|---|---|---|---|---|
| Fz10R | Anti-sense | aagaagcacagc acggaccagatg | 834-811 | 20 |

TABLE 5

Mouse TCF and Dkk oligonucleotide Primers for RT-PCR

| Primer | Orientation | Nucleotide Seq 5' to 3' | Nucleotide Position | SEQ ID NO |
|---|---|---|---|---|
| TCF1F | Sense | acgaacatttca gcagtccacac | 197-219 | 21 |
| TCF1R | Anti-sense | gcattgaggggt ttcttgatgac | 629-607 | 22 |
| TCF3F | Sense | caacgaatcgga gaatcagagc | 208-229 | 23 |
| TCF3R | Anti-sense | atggcgaccttg tgtccttgac | 509-488 | 24 |
| TCF4F | Sense | tgcctggtgggt gaaaaatgc | 96-115 | 25 |
| TCF4R | Anti-sense | cttgagggtttg tctgctctgg | 561-540 | 26 |
| LEF1F | Sense | ttctcttttct cccctccccc | 288-309 | 27 |
| LEF1R | Anti-sense | aaacctctccac ggattcctcg | 567-546 | 28 |
| Dkk1F | Sense | acattcgccacc ttctggattg | 1501-1525 | 9 |
| Dkk1R | Anti-sense | gcaaaagcacca accacacttg | 1797-1776 | 29 |
| Dkk2F | Sense | aatgcggaagaa tgagggatg | 1593-1613 | 30 |
| Dkk2R | Anti-sense | tgccaatctgaa ggaaatgcc | 1839-1819 | 31 |
| Dkk3F | Sense | cgtggacttgc aaaatgtaacc | 1511-1533 | 32 |
| Dkk3R | Anti-sense | gagcactggctt tcagaggtattg | 1937-1914 | 33 |
| Dkk4F | Sense | aagccccagaaa tcttccagc | 697-717 | 34 |
| Dkk4R | Anti-sense | tgaacacaacaa caagtcccgtg | 839-817 | 35 |

Sub-Cloning of PCR Fragments and DNA Sequence Analysis

PCR fragments were subcloned using TOPO-TA cloning vector according to manufacturer instructions (Invitrogen) and sequence analysis performed as previously described (Qiang et al., 2003). Data analysis was performed using MacVactor software and comparisons made with NCBI BLAST (http://www.ncbi.nlm.nih.gov/blast/).

Real-time Quantitative PCR

One microgram of total RNA was reverse transcribed into total cDNA. Quantitative PCR (qPCR) was performed using an ABI Prism 7000 sequence detection system (Applied Biosystems, Foster City, Calif.). The reaction mixture contained 1 ml of cDNA, dedicated buffers with specific primers and probes (5'-labeled by 6-carboxy-fluorescein and 3'-labeled by 1-carboxy-teteramethyrhdamine), and DNA polymerase in a total 20 ml volume. Following 2 min incubation at 50° C. and 10 min incubation at 95° C. for denaturing, the reaction was subjected to 40-cycle amplification at 95° C. for 15 s to denature and at 60° C. for 1 min for annealing/extension. Each cDNA sample was analyzed in triplicate in parallel with GAPDH as a control. Changes in mRNA concentration were determined by subtracting the CT (threshold cycle) of target gene from the CT of GAPDH ($\Delta$=CT gene–CT GAPDH). The mean of $\Delta$ control was subtracted from the ASiLRP5/6 reaction (mean $\Delta$ control–ASiLRP5/6=e) The difference was calculated as $2^c$ by the $2^{-\Delta\Delta C}{}_T$ (35).

RNA Interference

Chemical synthesis of siRNA specific to LRP5/6, GFP, and control siRNA were purchased from Qiagen (Valencia, Calif.). The siRNA were transiently transfected into C2C12 using Lipofectamine according to manufacturer instructions (Invitrogen). RNA was isolated after 24, 48 or 72 hours then subjected to RT-PCR or qPCR for determination of efficacy of target gene silencing.

Statistical Analysis

Statistical significance of differences between experimental groups was analyzed by a Student's t-test using the Microsoft Excel software statistical package. Significant p values were less than 0.05 by two-tailed test.

Expression of Wnt Receptors and Co-Receptors in OB Cells.

RT-PCR was used to evaluate the presence of Wnt receptor mRNA in C2C12, hFO1.19, and two human osteoblast-like cells lines, MG63 and Saos-2. Analysis using primers for all Fz family members (FIG. 42A) revealed expression of Fz1, 2, 4, 5, 6, 7, 8, and 9 with relatively higher levels of Fz1, 6, and 7 in C2C12 cells. Similar expression of multiple Fzs was observed in the human lines. Fz3 was expressed in all human lines, but not C2C12, while Fz6 was expressed in C2C12 but none of the human lines. LRP5 and LRP6 were identified in all mouse and human lines indicating. Thus, both components of functional Wnt receptors are expressed in OB cell lines and the presence of multiple receptors is likely.

Canonical Wnt Signaling is Activated in Pre-osteoblast Cell Lines.

Having demonstrated the presence of Fz and LRP receptors, we sought to determine whether a functional canonical Wnt/b-catenin pathway was present by first examining the status of downstream b-catenin. Because osteoblasts express high levels of cadherin proteins (including b-catenin) (Cheng et al., 1998), especially in the form of membrane-bound protein (Nelson and Nusse, 2004), the GST-E-cadherin binding assay was used to separate cytosolic, free (uncomplexed) beta-catenin from the membrane bound form. Examination of Wnt3a treatment effects revealed significant increases of free b-catenin appearing in a time-dependent manner (FIG. 42B (panel a)) in all cell lines. Increases in beta-catenin levels were apparent at 8 hr and remained elevated for 24 hrs. Increases in beta-catenin correlate with the presence of the non-phosphorylated, transcriptionally active form of the protein (van Noort et al., 2002) as determined by analysis with antibodies specific to non-phosphorylated b-catenin (FIG. 42B (panel b)).

RT-PCR analysis of TCF/LEF family members revealed expression of TCF1, 3, 4, and LEF1 mRNA in C2C12 cells (FIG. 42B (panel c)). Similar results of multiple TCF/LEF family member expression were observed in the human lines although LEF 1 appeared not to be expressed in MG63 (FIG. 42B (panel d)). Transient transfection of cells with TOPflash reporter constructs containing binding sites for the b-catenin/TCF/LEF transcription complex resulted in a significant increase in luciferase activity in the presence of Wnt3a CM. In contrast, no transcriptional activation was observed in control cells treated with L929 CM or cells transfected with FOPflash containing mutant TCF/LEF biding sties (FIG. 42B (panel e)). Taken together, these results indicate that a canonical Wnt signaling pathway is functional in pre-osteoblast cells.

Dkk1 and MM Patient Sera Inhibit Wnt3a Induced Beta-Catenin in Pre-Osteoblasts.

To examine the effect of Dkk1 in OBs, cells were incubated with increasing amounts of Dkk1 prior to Wnt3a treatment. As shown in FIG. 3A, pretreatment with Dkk1 led to dose-dependent inhibition of Wnt3a-increased, non-phosphorylated b-catenin in C2C12, hFOB1.19 and Saos-2 cells. Dkk1 inhibited non-phosphorylated b-catenin at concentrations beginning at 25 ng/ml with maximal inhibition at 50 ng/ml in C2C12. In hFOB 1.19 and Saos-2 pronounced inhibition was observed at the lowest concentration tested (5 ng/ml) which changed only moderately with increasing concentration. Similar results were observed in analysis of total free b-catenin (not shown).

To determine whether Dkk1 expression by MM cells might have similar effects on functional Wnt signaling in the bone marrow microenvironment, the following experiments were performed. First, stable Dkk1-expressing clones were generated in the OPM2 mM cell line and lysates containing Dkk1 used to determine the effect on Wnt3a-induced stabilization of b-catenin in C2C12 cells. The presence of Dkk1 protein in cell lysates from stable OPM-2 clones was determined by Western blot analysis with anti-V5 antibody (FIG. 42C (panel b)). Dkk1 CM from OPM-2/Dkk1-expressing clones inhibited accumulation of uncomplexed, non-phosphorylated b-catenin in C2C12 cells (FIG. 42C (panel c)). Furthermore, bone morrow plasma from four MM patients containing over 100 ng/ml of Dkk1 (designated H1 to H4) similarly inhibited b-catenin (FIG. 42C (panel d)). These results suggest that Dkk1 produced from MM cells and MM bone marrow can negatively regulate Wnt signaling in pre-osteoblasts.

Dkk1 Inhibits BMP-2-Induced ALP Activity.

Given the characterization of a functional Wnt signaling pathway in mouse and human pre- and osteoblast-like cells, experiments were undertaken to identify the biological effects associated with this pathway. C2C12 cells were selected as a model since following reasons. First, they undergo pre-osteoblast differentiation in the presence of BMP-2 (Nishimura et al., 1998). Second, they express less Dkk1 mRNA and protein, compared with other human cell lines and primal human mesenchymal cells and finally they react with addition of Dkk1 more sensitively that human other lines (FIG. 42C (panel a)). As expected, BMP-2 treatment led to increased ALP activity whereas Wnt3a alone had no effect (FIG. 42D (panel a)). C2C12 cells treated with both Wnt3a and BMP-2 demonstrated no obvious increase in ALP activity over BMP-2 alone indicating a lack of synergy between these factors in ALP production. Thus, exogenous Wnt3a alone is not sufficient to induce C2C12 differentiation. However, since Wnt3a mRNA (data not shown) and abundant steady state levels of b-catenin were detected in C2C12 cells (FIGS. 42B and 42C), the possibility of a cooperative role between BMP and Wnt pathways in C2C12 differentiation was next examined using Dkk1 protein to block canonical Wnt-beta-catenin signaling. Interestingly, pretreatment of C2C12 cells with 100 ng/ml of Dkk1 significantly inhibited ALP activity in the presence or absence of Wnt3a (FIG. 42D (panel a)).

Comparable studies in the human cell lines hFOB 1.19 and Saos-2 cells produced similar results (FIG. 42D (panels b, c)). These findings suggest that an autocrine b-catenin loop is critical to BMP-2-mediated pre-osteoblast differentiation.

An Autocrine Wnt Loop is Required for Differentiation of C2C12 Cells.

To address the role of autocrine Wnt-b-catenin signaling in pre-osteoblast differentiation, C2C12 cells were transfected with a dominant negative (DN)-b-catenin construct which lacks TCF/LEF binding sites and inhibits transcriptional activity (Chung et al., 2002). DN-beta-catenin expression was confirmed by western blot analysis with anti-X-press antibody (FIG. 42E (panel a)) and DN-beta-catenin clones exhibited significantly reduced Wnt3a mediated luciferase activity (FIG. 42E (panel b)). Importantly, marked reductions in ALP activity were observed in DN-b-catenin C2C12 cells in the presence of BMP-2 (FIG. 42E (panels c, d)). These results suggest that canonical beta-catenin signaling contributes to BMP-2-induced differentiation in C2C12 cells. To further confirm the effect of Dkk1 on osteoblast differentiation, we ectopically expressed Dkk1 and Dkk2 in C2C12 cells. Overexpression of both Dkk1 and Dkk2 inhibited endogenous non-phosphorylated beta-catenin (FIG. 42E (panel e)). Yet, exposure of these clones to medium containing 200 ng/ml of BMP-2 significantly inhibited the ALP activity in both Dkk1 and Dkk2 clones, compared with cells expressing empty vector (FIG. 42E (panel f)). These results suggest that Dkk1 and Dkk2 inhibit mesenchymal cell differentiation by inhibition of autocrine Wnt-teta-catenin pool in pre-osteoblasts.

Inhibition of ALP Activity by siRNA Specifically Targeting LRP5/6

To determine the specific role of Wnt receptors in mesenchymal cell differentiation in vitro, we used siRNA specific for LRP5 and LRP6 to down regulate gene expression. As shown in FIG. 42F (panel a), LRP5 and LRP6 mRNA expression in C2C12 cells was inhibited by the homologous (siLRP5 and siLRP6), but not by heterogeneous siRNA (control siRNA). Furthermore, inhibition of either LRP5/6 by their respective siLRNA's occurred in a dose-dependent manner as determined by qPCR (FIG. 42F (panels b, c) and neither reduced expression of the other. Treatment of siLRP5- and siLRP6-expressing cells with BMP-2 resulted in significant reductions in ALP activity compared with cells expressing control siRNA (FIG. 42F (panel d)) indicating that LRP co-receptors are likely required for pre-osteoblast differentiation.

Dkk1 Inhibition of Pre-Osteoblast Differentiation is Independent of the Smad/Cbaf1/Runx2 Pathway.

Figure 42H:
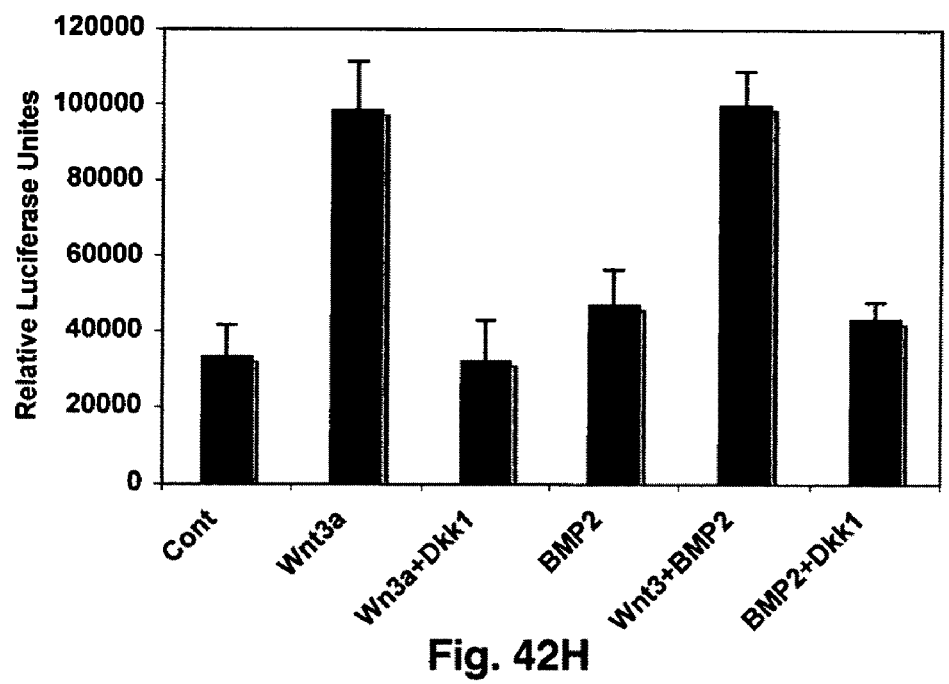
Figure 42I:
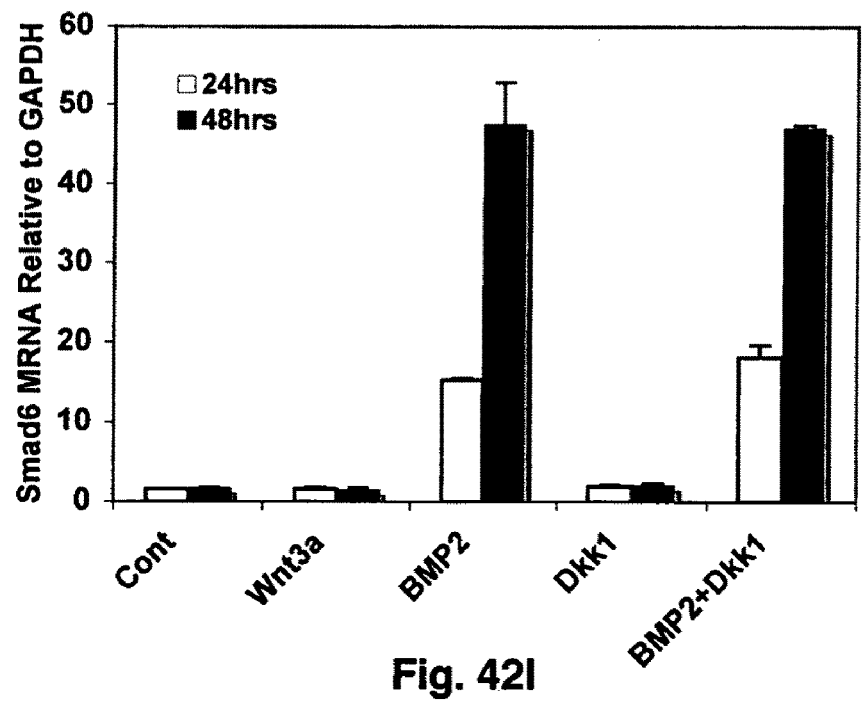

To address the question of whether the Wnt and BMP-2 pathways were involved in cross-regulation and co-regulation of downstream elements and/or if Dkk1 directly interferes with BMP-2 signaling to inhibit osteoblast differentiation, the effects of BMP-2 on b-catenin stabilization were first analyzed. As shown in FIG. 42G (panel a), treatment of all pre-osteoblast cell lines with BMP-2 for 8, 24, and 48 hrs did not result in changes in b-catenin as compared to Wnt3a treated controls. BMP-2 alone did not induce TCF/LEF transcriptional activity, nor did it synergize Wnt3a-stimulated TCF/LEF transcriptional activity as determined by luciferase activity in C2C12 cells transfected with TOPflash constructs (FIG. 42H). Thus, BMP-2 did not activate the Wnt-beta-catenin pathway at the beta-catenin and TCF/LEF levels. Experiments were next implemented to determine whether Wnt and Dkk1 directly regulate BMP-2 signaling. First, BMPR-I and -II were immunoprecipitated from C2C12 cell lysates followed by blotting with antibodies to LRP5 and LRP6. Complexes of LRP5/6 and BMPR-I/-II were not found following either Wnt3a or Dkk1 treatment. Similar results were obtained in 293T cells transiently transfected with plasmid containing LRP5/6 cDNA. To ascertain whether Wnt3a can activate BMP-2 downstream targets, Smad phosphorylation was analyzed using antibodies specific to p-Smad1-S463/465. Wnt3a did not induce phosphorylation of Smad1 in C2C12 cells (FIG. 42G (panel b)) nor Smads5 and 8 as assessed with antibodies to p-Smad5-S463/463, and p-Smad8-S426/428 in contrast to BMP-2 controls. Because BMP-2 also increases Smad6 gene expression, which serves as inhibitor of BMP-2 signaling (Iton et al., 2001; Wang et al., 2007), the present invention examined if Wnt and Dkk1 affects its expression. As expected, BMP-2 induced increase in Smad6 mRNA in a time-dependent manner in C2C12 cells as measured by qPCR analysis (FIG. 42I). However, neither Wnt3a alone nor Dkk1 affected BMP-2-induced Smad6 gene expression. Finally, the effect of Wnt3a and Dkk1 on transcriptional activity of Cbfa-1/Runx2 was investigated by transiently transfecting C2C12 with a luciferase reporter construct, Cbfa-1-Luc and treating with Wnt3a and Dkk1. Cell lysates assayed for luciferase revealed no change in activity indicating the Wnt3 role in osteoblast differentiation is independent of Cbfa-1/Run2 transcriptional activity. Taken together, these results suggest that Wnt does not activate downstream elements in the BMP-2 pathway, BMP-2 does not activate downstream elements in the Wnt pathway, and Dkk1 does not directly inhibit BMP-2 signaling.

EXAMPLE 19

Effect of Myeloma Derived DKK-1 on Wnt-Regulated Osteoprotegerin and RANKL Production by Osteoblasts The present invention examined the influence of DKK1 on RANKL/OPG expression in myeloma.

Primary Myeloma Cells and Established Myeloma Cell-Lines

Primary plasma cells (PC) were obtained from heparinized bone marrow (BM) aspirates from multiple myeloma (MM) patients during scheduled clinic visits. Mononuclear cells were isolated from BM of MM pateints using a Ficoll-Hypaque density gradient centrifugation. PC isolation from mononuclear cell fraction was performed by immunomagnetic bead selection with monoclonal mouse antihuman CD138 antibodies using the AutoMACs automated separation system (Miltenyi-Biotec, Auburn, Calif.). PC purity of more than 85% homogeneity was confirmed by 2-color flow cytometry using CD138$^+$/CD45 and CD38$^+$/CD45 criteria (Becton Dickinson, San Jose, Calif.), immunocytochemistry for cytoplasm light-chain immunoglobulin (Ig), and morphology by Wright-Giemsa staining.

Cell lines: Human MM cell line, OPM-2 was cultured in RPMI1640 as previously described (Qiang et al., 2003). Mouse pluripotent mesenchymal precursor cell line C2C12 that has the potential of differentiating into osteoblast in the presence of BMP-2 (Katagiri et al., 1994) and human osteoblast cell line hFOB1.19 were purchased from America Type Culture Collection (Manassas, Va.). C2C12 and human osteoblast-like cell line, Saos-2 and MG63 were cultured in Dulbecco's Modified Eagle Medium (DMEM) (Invitrogen, Carlsbad, Calif.) containing 10% heat-inactivated FBS, penicillin (100 U/ml), streptomycin (100 mg/ml), and 4 mM L-glutamine. Cells were maintained at 37° C. and humidified with 95% air and 5% $CO_2$ for cell culture.

Coculture System

C2C12 cells were cultured in 6-well plates in DMEM with 10% FBS and maintained at subconfluence. MM cells ($5 \times 10^5$/ml) were seeded on the C2C12 in the presence or absence of Wnt3a-CM or Cont-CM for indicated times. For coculture with primary cells, CD138 positive cells were cultured on of the C2C12 monolayer for 72 hours in the presence or absence of rWnt3a with and without anti-DKK1 antibody (R&D System) for 48 hours. Total RNA was isolated using TRIZOL reagent (Invitrogen). Supernatants were harvested for protein analysis.

Constructs and Transfectants

A MM cell line, OPM-2, stably expressing DKK1 was generated as previously described (Qiang et al., 2003). Functional DKK1 protein was determined by blocking Wnt3a induced TCF/LEF transcriptional activity using the TOPflash luciferase assay as previously described. To generate a DKK1 expressing osteoblast cell line, C2C12 cells were transfected, using Lipofectamine (Invitrogen-Life Technologies, Inc.), with a pEF-V5 vector or the same vector carrying a DKK1 cDNA, according to manufacturer's instructions. Clonal cell lines were generated by limited dilution in growth media containing blasticidin. Positive clones were detected by anti-V5 antibody with Western blotting analysis. DKK1 protein concentration in supernatant cultured positive clones was measured by ELISA analysis. Functional DKK1 protein was determined by analyzing the effect on stabilization of free beta-catenin as previously described (Qiang et al., 2007, in press).

Preparation of Conditioned Medium

Wnt3a conditioned medium (Wnt3a-CM) or control (Cont-CM) was prepared as described (Qiang et al., 2003). Briefly, Wnt3a-producing L cells (stably transfected with Wnt3a cDNA kindly provided by Dr Shinji Takata) or control L cells were cultured to confluence in DMEM medium supplemented with 10% FCS after which the medium was replaced with serum-free DMEM. The culture supernatant was collected after 72 hours and designated Wnt3a-CM and Cont-CM, respectively. The concentration of Wnt3a in Wnt3a-CM was evaluated by correlating β-catenin stabilization with that of recombinant Wnt3a (R&D Systems, Minneapolis, Minn.). The concentration in 100% CM equates to the 150 to 200 ng/ml of recombinant Wnt3a. DKK1 conditioned medium (DKK1-CM) and control medium (Cont-CM) were prepared as described previously. DKK1 protein in DKK1-CM, Cont-CM, supernatant from culture media of C2C12, MG63, and Saos-2 cells, and sera from MM pateints were measured by ELISA analysis as described previously.

Immunoblotting Analysis and GST-E-Cadherin Binding Assay

Proteins from cell lysates derived from C2C12 and OPM-2 cells expressing DKK1 or empty vector were separated by SDS-PAGE and transferred to Immobilon polyvinylidene difluoride membranes (Millipore, Bedford, Mass.). Immunoblotting was performed using the indicated antibodies as previously described (Qiang et al., 2005).

The GST-E-cadherin binding assay was performed as described (Bafico et al., 1998). Briefly, proteins were isolated from cells that had been treated with recombinant Wnt3a for indicated times. The beta-catenin binding site of E-cadherin as a GST-fusion protein was purified using GST beads. GST-E-cadherin was used to precipitate uncomplexed beta-catenin in 500 mg of cell lysate. Precipitated beta-catenin was detected by immunoblotting analysis using a b-catenin monoclonal antibody (Qiang et al., 2005).

Enzyme-Linked Immunosorbent Assay

Microtiter plates were coated with 50 μl of anti-DKK1 antibody (R&D Systems, Minneapolis, Minn.) according to manufacturer recommendations. Bone marrow serum (1:50) in dilution buffer was added and incubated overnight at 4° C. Plates were washed and incubated with biotinylated goat anti-human DKK1 IgG (R&D Systems, Minneapolis, Minn.) followed by streptavidin-horseradish peroxidase (Vector Laboratories), according to manufacturer recommendations. The concentrations of OPG and RANKL proteins in cultured supernatant were measured using the kits from according to manufacturer recommendations (R&D Systems, Minneapolis, Minn.).

RT-PCR Analysis and DNA Sequence Analysis

Total RNA was isolated using TRIzol reagent (Invitrogen). First strand cDNA synthesis was performed as previously described (Qiang et al., 2003). All PCR reactions began with a first cycle at 95° C. for 3 min and a final cycle at 72° C. for 10 minutes with an additional 35 cycles at 94° C./30 s, 60° C./45 s, 72° C./1 min. Primers, including human and mouse DKKs were designed using the 'primer pair program' using MacVector software (Qiang et al., 2005) based on gene sequences from the NCBI Gene Bank (www.ncbi.nlm.nih.gov). Primer sequences and expected sizes of DNA fragments amplified for the indicated mouse and human genes are listed in Table 6. PCR fragments were subcloned using TOPO-TA cloning vector according to manufacturer instructions (Invitrogen) and sequence analysis performed as previously described (Qiang et al., 2003). Data analysis was performed using MacVactor software and comparisons made with NCBI BLAST (http://www.ncbi.nlm.nih.gov/blast/).

TABLE 6

DKK oligonucleotide primers for RT-PCR

| Primer | Orientation | Nucleotide sequence (5' to 3') | Nucleotide position |
|---|---|---|---|
| mDkk1F | Sense | acacacacacacaca cacacacatc (SEQ ID NO: 36) | 1501-1525 |
| mDkk1R | Anti-sense | gcaaaagcaccaacc cacacttg (SEQ ID NO: 29) | 1797-1776 |
| mDkk2F | Sense | aatgcggaagaatga gggatg (SEQ ID NO: 30) | 1593-1613 |
| mDkk2R | Anti-sense | tgccaatctgaagga aatgcc (SEQ ID NO: 31) | 1839-1819 |
| mDkk3F | Sense | cgtggacttggcaaa atgtaacc (SEQ ID NO: 32) | 1511-1533 |
| mDkk3R | Anti-sense | gagcactggctttca gaggtattg (SEQ ID NO: 33) | 1937-1914 |
| mDkk4F | Sense | aagccccagaaatct tccagc (SEQ ID NO: 34) | 697-717 |
| mDkk4R | Anti-sense | tgaacacaacaacaa gtcccgtg (SEQ ID NO: 35) | 839-817 |
| hDkk1F | Sense | ccaacgcgatcaaga acctgcc (SEQ ID NO: 37) | 154-176 |
| hDkk1R | Anti-sense | gatggtgatctttct gtatcc (SEQ ID NO: 38) | 790-811 |
| hDkk2F | Sense | ctgatggtggagagc tcacag (SEQ ID NO: 39) | 201-223 |
| hDkk2R | Anti-sense | cctgatggagcactg gtttgcag (SEQ ID NO: 40) | 749-772 |
| hDkk3F | Sense | agtacacctgccagc catg (SEQ ID NO: 41) | 611-630 |

TABLE 6-continued

DKK oligonucleotide primers for RT-PCR

| Primer | Orientation | Nucleotide sequence (5' to 3') | Nucleotide position |
|---|---|---|---|
| hDkk3R | Anti-sense | ctccaggtcttccag ctcctgg (SEQ ID NO: 42) | 1072-1093 |
| hDkk4F | Sense | ggtcctggacttcaa caacatc (SEQ ID NO: 43) | 168-190 |
| hDkk4R | Anti-sense | cttaatcgagcatgc tgccg (SEQ ID NO: 44) | 738-758 |

Real-Time Quantitative PCR

One microgram of total RNA was reverse transcribed into total cDNA. Quantitative PCR (qPCR) was performed using an ABI Prism 7000 sequence detection system (Applied Biosystems, Foster City, Calif.). The reaction mixture contained 1 ml of cDNA, dedicated buffers with specific primers and probes (5'-labeled by 6-carboxy-fluorescein and 3'-labeled by 1-carboxy-teteramethyrhdamine), and DNA polymerase in a total 20 ml volume. Following 2 min incubation at 50° C. and 10 min incubation at 95° C. for denaturing, the reaction was subjected to 40-cycle amplification at 95° C. for 15 s to denature and at 60° C. for 1 min for annealing/extension. Each cDNA sample was analyzed in triplicate in parallel with GAPDH as a control. Changes in mRNA concentration were determined by subtracting the CT (threshold cycle) of target gene from the CT of GAPDH ($\Delta$=CT gene–CT GAPDH). The mean of $\Delta$ control was subtracted from the $\Delta$SiLRP5/6 reaction (mean $\Delta$ control–$\Delta$SiLRP5/6=e) The difference was calculated as $2^e$ by the $2^{-\Delta\Delta CT}$ (Livak and Schmittgen, 2001).

Silencing DKK1 Expression by DKK1 Short Hairpin RNA

A sequence previously shown be an effective siRNA specific to human DKK1 gene (5'-caatggtctggtacttattcccgaag-gattaagtaccagaccattgcacc-3'; SEQ ID NO: 45) (Hall et al., 2005) was used to design a synthetic double-stranded oligo-nucleotide sequence for short hairpin RNA (shRNA) knock-down studies, as described (Szule et al., 2006) and designed shDKK1. A control oligonucleotide sequence not matching any sequence in the human genome (5'-gatccccgacacgcgact-tgtaccacttcaagagagtggtacaagtcggtcgtctttta -3'; SEQ ID NO: 46) was used as a control shRNA sequence (designated as shCont). Both double-stranded shRNA sequences were obtained from Integrated DNA Technologies (Coralville, Iowa). The double-stranded oligonucleotides were cloned into pLVTHM, and virus was generated by cotransfection of 293T cells with the pLVTHM vector and helper plasmids pMD2G and pCMV-dR8.91 (all kindly provided by Dr Didier Trono, University of Geneva, Switzerland). The crude lentivirus was concentrated from cultured supernatant of the 293T cells and filtered (0.45 μm) and viral titers were determined by measuring the percent of green fluorescent protein (GFP)-positive cells present 48 hours after infection of 293T cells. The Saos-2 and MG63 cells were infected with lentivirus supernatant for indicated times. The efficiency of infection with shDKK1 and shCont virus was determined by counting the percent of green fluorescent protein (GFP) positive cells by fluorescence microscopy. Total RNA, isolated after 24, 48 or 72 hours was subjected to RT-PCR and qPCR to determine the degree of target gene silencing. After 72 hours after infection supernatants of the cells were subject to ELISA analysis to determine DKK1 protein concentration.

Statistical Analysis

Statistical significance of differences between experimental groups was analyzed by a Student's t-test using the Microsoft Excel software statistical package. Significant p values were less than 0.05 by two-tailed test.

Wnt3a Induces OPG mRNA and Protein Levels in Osteoblasts

Wnt3a stimulated OPG mRNA expression in a dose-dependent and time-dependent fashion in murine mesenchymal osteoblast-precursor C2C12 cells (FIG. 43A (panel a)) as well as in human osteoblast-like Saos-2 cells (FIG. 43A (panel b)) and in MG63 cells (data not shown), reaching increases of 40-fold, 2-fold and 1.5-fold, respectively. Similar results were obtained for OPG protein levels (by ELISA analysis of culture supernatants) (FIG. 43A (panel c)), with revealed increases relative to controls by 2000-fold in C2C12 cells versus 4-fold in Saos-2 (FIG. 43A (panel d)). The response in OPG protein level was consistent with free b-catenin levels in the cytoplasm as measured by E-cadherin binding analysis (see FIG. 43A (panel c)).

DKK1 Diminishes Wnt3a Mediated OPG Production in Osteoblasts

Using recombinant DKK1 protein, b-catenin level was reduced (using the pull-down assay) in C2C12 (FIG. 43B (panel a)) and in Saos-2 cells (FIG. 43B (panel b)). Higher DKK1 concentrations were required for effective DKK1-induced attenuation of Wnt3a-induced OPG transcription and translation in Saos-2 than C2C12 cells (FIG. 43B (panels c, d)). Although endogenous OPG mRNA and protein levels were approximately 40-fold and 100-fold higher in Saos-2 and MG63 cells, respectively, than in C2C12 cells (see FIGS. 43A and 43B), induction of OPG mRNA and protein in response to Wnt3a stimulation in both Saos-2 and MG63 were less obvious than in C2C12 cells, suggesting a greater sensitivity of these cells to DKK1.

Over-Expression of DKK1 in C2C12 Cells Reduces Wnt3-Induced OPG

The present invention examined differences in response to Wnt3a stimulation relative to DKK1 concentrations required for Wnt3a inhibition between these cell lines. Examining endogenous DKK mRNA status by RT-PCR analysis across cell lines revealed that C2C12 cells had lower levels of DKK1 than DKK2 and DKK3 (FIG. 43C (panel a)), whereas there was abundance of all DKK (including DKK1) mRNAs in three human osteoblast lines (Saos-2, MG63, hFOB1.19) (FIG. 43C (panel b)). Similar results were obtained with DKK protein measurements (FIG. 43C (panel c)), suggesting that the relatively high endogenous DKK1 protein levels in Saos-2 and MG63 cells may interfere with the ability of these cells to respond to Wnt3a simulation. To test this hypothesis, C2C12 cells were transfected with constructs containing Dkk1 cDNA (pEF/DKK1) or empty vector (pEF/EV), and DKK1 protein levels were detected in these stable clones by anti-V5 antibody (FIG. 43C (panel d)). Significantly higher concentrations of DKK1 protein (160 ng/ml) in pEF/DKK1 clones were detected by ELISA analysis compared with vector control (pEF/EV) cells (FIG. 43C (panel e)). OPG mRNA (FIG. 43C (panel f)) and OPG protein (FIG. 43C (panel g)) were both significantly reduced in DKK 1-expressing C2C12 cells (pEF/DKK 1) compared to control cells. These results suggest C2C12 cells, upon DKK1 transfection, become less sensitive to Wnt3a signaling and thus become more similar to the human osteoblast-like cells.

DKK1 Silencing by shRNA Restores Sensitivity to Wnt3a Stimulation in Saos-2 Cells To further confirm that impaired Wnt3a signaling can be related to endogenous DKK1, DKK1-specific shRNA silencing experiments were carried out. Endogenous DKK1 mRNA in Saos-2 cells was inhibited shDKK1, as determined by RT-PCR, but not by a non-specific shRNA (FIG. 43D (panel a)). Relative to shCont cells, a time-dependent significant decrease in DKK1 protein levels was observed in shDKK1-expressing Saos-2 cells (FIG. 43D (panel b)); such cells responded to Wnt3a treatment with a significant increase in OPG mRNA (FIG. 43D (panel c)) and OPG protein (FIG. 43D (panel d)) relative to controls. Thus, endogenous DKK1 levels critically control the responsiveness of Wnt3a signaling in osteoblasts as measured by OPG production. The low endogenous levels of DKK1 in C2C12 cells makes these cells particularly well suited to investigate the role of Wnt3a exposure on OPG expression in cells of the osteoblast lineage.

Co-Culture with MM Cells Expressing DKK1 Prevents Wnt3a-Induced OPG in Osteoblasts To determine whether DKK1 expression by MM cells interferes with Wnt3a-induced OPG transcription in the bone marrow microenvironment, OPM-2 mM cells stably expressing DKK1 were produced as confirmed by demonstrating an inhibition of TCF/LEF transcriptional activity relative to controls (Qiang et al., 2003). Supernatants of OPM-2/DKK1 clones contained the DKK1 protein as determined by Western blot analysis with anti-V5 antibody (FIG. 43E (panel a)). ELISA analysis showed that DKK1 in OPM-2/DKK1 expressing clones was significantly higher than that in control cells (FIG. 43E (panel b)). C2C12 cells, co-cultured with DKK1/OPM-2 cells, showed significant inhibition of both Wnt3a-induced OPG mRNA expression, determined by qPCR analysis, (FIG. 43E (panel c)) and of OPG protein at 48 and 72 hours (FIG. 43E (panel d)).

The same experiment was repeated with DKK1-expressing primary MM plasma cells from 5 patients. Results were similar to those obtained with OPM-2/DKK1 cells: a Wnt3a-induced OPG increase was significantly inhibited in C2C12 cells both at the mRNA (FIG. 43E (panel e)) and protein (FIG. 43E (panel f)) levels in all five cases. Collectively, these results suggest that DKK1-expressing MM cells impair Wnt3a-induced OPG production in osteoblasts.

Neutralization of DKK1 Protein Restored OPG Levels in Osteoblasts

Previous studies have shown that DKK1 in sera from MM patients inhibits osteoblast differentiation (Tian et al., 2003) and bone formation (Giuliani et al., 2007) which was shown to occur through a DKK1-mediated attenuation of Wnt3a-induced stabilization of b-catenin. Similar to the presence of 100 ng/ml of DKK1 in culture media, treatment of C2C12 cells with sera from bone marrow of eight MM patients containing high levels of DKK1, all in excess of 100 ng/ml of DKK1 (designated MMSH), significantly inhibited Wnt3a-induced increase in OPG mRNA (FIG. 43F (panel a)). The observation that sera containing less than 10 ng/ml of DKK1 protein (MMSL) still inhibited Wnt3a-induced OPG transcription might suggest that factors besides DKK1 may contribute to interference with Wnt3a-induced OPG expression.

To verify that DKK1 in sera of MM patients was contributing to the suppression of Wnt3a-mediated OPG expression in osteoblasts, the MM serum was preincubated with a neutralizing antibody specific to DKK1. Compared to control IgG antibody, pretreatment of C2C12 cells with anti-DKK1 antibody significantly rescued Wnt3a-induced OPG mRNA (FIG. 43F (panel b, c)) and protein expression (FIG. 43F (panel d)). Collectively, these results suggest that DKK1-expressed by MM cells can negatively regulate Wnt3a-mediated OPG secretion in osteoblasts.

Wnt3a-Mediated Inhibition of RANKL is Blocked by DKK1 from MM Cells

Since indirect activation of Wnt signaling by inhibition of GSK3beta has been reported to regulate RANKL in MC3T3-E1 osteoblasts (Spencer et al., 2006), the effect of DKK1 on this process was examined herein as another potential mechanism underlying MM bone disease. Treatment of C2C12 cells with Wnt3a for 48 hours resulted in a significant decrease in RANKL mRNA (FIG. 43G (panel a)), which could be restored by pretreatment of cells with DKK1. Similar results were observed in DKK1-pretreated Saos-2 (FIG. 43G (panel b)) and MG63 cells (FIG. 43G (panel c)). To further confirm the role of DKK1 on this process, we employed DKK1-overexpressing C2C12 cells, in which high DKK1 concentrations can abrogate Wnt3a signaling (see FIG. 43C (panel e)). RANKL mRNA (FIG. 43G (panel d)) and protein expression (FIG. 43G (panel e)) in PEF/DKK1 cells was significantly higher than in control pEF/EV in the absence of Wnt3a protein. Wnt3a treatment of pEF/DKK1 cells significantly altered RANKL expression ($p<0.01$), compared with pEF/DKK1 cells without Wnt3a. These results suggest that RANKL protein in osteoblast cells is determined by the ratio of Wnt and DKK1. We were able to show that sera from 8 mM subjects with high DKK1 concentrations ($>=100$ ng/ml) significantly decreased Wnt3a-mediated inhibition of RANKL mRNA expression (FIG. 43G (panel f)) while sera containing low concentration of this molecule (<10 ng/ml) were ineffective. Taken together, these results suggest that DKK1, through inhibition of canonical Wnt signaling, increases RANKL in osteoblasts.

EXAMPLE 20

Effects of Neutralizing Antibody Against DKK1 in the Preclinical SCID-Rab Model for Primary Human Myeloma Recent clinical and experimental studies suggest that myeloma bone disease drives tumor progression. Growth of myeloma cells from a subset of patients was inhibited by inhibitors of osteoclast activity (Yaccoby et al., 2002). Although isolated osteoclasts support survival and proliferation of myeloma cells, osteoblasts have a negative impact on myeloma. Additionally, studies focusing on cell-signaling molecules have demonstrated that myeloma cells produce the Wnt signaling inhibitor DKK1 that inhibits osteoblast differentiation in vitro (Tian et al., 2001) and that immature as opposed to mature, osteoblasts produce elevated levels of RANKL and IL-6 (Gunn et al., 2004). Moreover, synthesis of osteoprotegerin (OPG), a soluble receptor of RANKL and potent osteoclast induction signal, is dependent on canonical Wnt signaling in osteoblasts (Glass et al., 2005). Furthermore, DKK1 has been shown to mediate mesenchymal stem cell proliferation in favor of differentiation (Gregory et al., 2003).

Therefore, whether inhibition of Wnt signaling and osteoblast differentiation by DKK1 resulted in increased activity of osteoblast precursors that induced a cascade of events leading to myeloma disease progression was examined. Additionally, shifts in bone marrow concentrations of secreted factors DKK1, RANKL, OPG and IL-6 contributes to myeloma cell growth and an absolute shift in numbers of mature and immature osteoblasts and osteoclasts that favors bone destruction and myeloma cell growth.

A neutralizing antibody against DKK1 was used in a xenograft SCID-rab mouse model for primary human myeloma (Yata & Yaccoby, 2004) to examine the effect of DKK1 inhibition on myeloma-induced bone disease and the association between increased osteoblast activity and tumor growth. This system is a second generation of the SCID-Hu model (Yaccoby et al., 1998). In these systems, myeloma cells from patients with myeloma engraft in transplanted bone and produce typical disease manifestations including induction of osteolystic bone lesions.

Briefly, SCID-rab host mice were constructed by subcutaneous implantation of rabbit bones (FIG. 44) as described (Yata and Yaccoby, 2004). After 6-8 weeks, myeloma cells from 7 patients were inoculated directly into the implanted bone in the host. Tumor growth was then monitored by measuring the levels of human monoclonal immunoglobulins in the mice sera. Increased tumor burden was usually associated with induction of osteolytic bone lesions as indicated on X-ray radiographs. Treatment was initiated when the levels were higher than 100 µg/ml. However, since the tumor burden varied between patients, treatment in each experiment was started at different time points after inoculation.

For each patient's cells, one SCID-rab mouse with established myeloma was injected with anti-DKK1 antibodies (R&D Systems) into the surrounding area of the implanted bone and another served as control and received a non-specific IgG antibody. The mice received polyclonal anti-DKK1 antibody at a concentration of 50 µg/injection/3 times a week in 4 experiments. In 3 experiments, the experimental mice received monoclonal anti-DKK1 antibody at concentration of 100 µg/injection/5 times a week. Experiments were continued for 4-6 weeks. No drug-related toxicity was observed during the experimental period. The growth of myeloma cells, bone resorption and formation, osteoclast and osteoblast numbers were then determined. The effect of treatment on bone mineral density (BMD) and tumor burden were analyzed using Student paired t-test.

The osteoclast numbers were determined by staining rabbit bone sections for TRAP and TRAP-expressing multinucleated osteoclasts were counted in 4 non-overlapping myelomatous bone surface areas of control and anti-DKK1 treated mice. Additionally, mature osteoblasts were identified by immunohistochemical staining of rabbit bone sections for osteocalcin and osteoblast numbers were counted in 4 non-overlapping myelomatous bone surface areas of these mice.

Treatment with anti-DKK1 resulted in increased number of osteocalcin-expressing osteoblasts and reduced TRAP-expressing osteoclasts (FIG. 45). The effect of anti-DKK1 treatment on osteoblast to osteoclast ratios was demonstrated on sequential bone sections. The surface of control IgG treated myelomatous bone was characterized by increased osteoclast activity and a reduction in osteoblasts whereas treatment with anti-DKK1 antibody led to an increased osteoblast numbers and reduced osteoclast numbers on the same bone surface (FIG. 46).

Next, whether anti-DKK1 effect on the osteoclast and osteoblast activity affected myeloma-induced bone loss in these mice was assessed. Bone resorption and formation was visualized by X-ray radiographs and quantified by measuring bone mineral density (BMD) of the implanted bone before the start of the treatment and at the end of each experiment. In control mice, the implanted rabbit bone mineral density was reduced during the experimental period. The bone mineral density in bones treated with anti-DKK1 was increased by >8% from pretreatment level (p<0.04) indicative of increased bone formation (FIG. 47). The bone anabolic affect of anti-DKK1 could also be visualized on x-ray radiographs; whereas in control mice bone resorption and lytic bone lesions were increased during the experimental period, the myelomatous bones from mice treated with anti-DKK1 had increased bone mass (FIG. 48).

Furthermore, myeloma tumor burden gradually increased in all control mice with time. In distinct contrast, an inhibition of tumor burden in 4 of 7 experiments and retardation of growth in the other 3 experiments was observed in mice treated with anti-DKK1 antibody. Overall, myeloma growth in mice treated with control and anti-DKK1 antibodies increased by 331% ad 162%, respectively (FIG. 47, p<0.02). Additionally, the growth of myeloma cells was also monitored by measuring the levels of human monoclonal immunoglobulins (hIg) in the mice sera and confirmed at the end of the experiments by histological examinations (H&E, cIg). Histological examination revealed that myeloma cells were absent in bone area containing high numbers of osteoblasts due to anti-DKK1 treatment (FIG. 49).

EXAMPLE 21

The Effects of Neutralizing Antibody Against DKK1 on Bone Mineral Density in the Preclinical Nonmyelomatous SCID-Rab Model The effects of the neutralizing antibody against DKK1, said DKK1 consisting amino acid sequence encoded by the DKK1 gene of SEQ ID NO; 47 were determined in SCID-rab mouse, constructed by subcutaneous implantation of rabbit bones (FIG. 44) as described (Yata and Yaccoby, 2004). The mice received polyclonal anti-DKK1 antibody at a concentration of 50 µg/injection/3 times a week in 4 experiments. In 3 experiments, the experimental mice received monoclonal anti-DKK1 antibody at concentration of 100 µg/injection/5 times a week. Experiments were continued for 4-6 weeks. The effects of DKK1 neutralizing antibody on the bone marrow density of implanted femurs in nonmyelomatous mice (n=18), and the uninvolved murine femur of myelomatous SCID-Rab mice (n=9) was determined. Treatment with DKK1 antibody resulted in a significant increase in bone marrow density of the nonmyelomatous implanted bone relative to controls (treated with irrelevant IgG antibody for 4-6 weeks) (19±6% vs. 3.+–0.5%; p<0.05) and in the murine femur (4.4±0.6% vs. 0.1±1.4%; p<0.015) (FIG. 50A-50C). The bone marrow density of uninvolved mouse femurs from myelomatous hosts did not change in both DKK1 AB-treated and controls (4.0±3.2% vs. 3.4±2.5%) (FIG. 50A-50C)

The following references were cited herein:
Anderson, et al., 1997 *Nature* 390:175-179.
Atkins et al., 2003, *J. Bone Miner. Res.* 18:1088-1098
Bafico et al., 1998, Oncogene, 16(21): 2819-25.
Bain et al., 2003, *Biochem Biophys Res Commun* 301:84-91
Bataille, et al 1991. *J Clin Invest* 88:62-66.
Baron, R., and Rawadi, G. 2007. *Endocrinology* 148:2635-2643.
Binato et al., 2006, Biochem J 393: 141-50.
Boyden et al., 2002, *N. Engl. J. Med.* 346:1513-1521
Canalis et al., 2003, Endocr Rev 24 92): 218-35.
Chen et al., 2006, J Biol chem 282: 526-33.
Cheng et al., 1998, J Bone Miner Res, 13: 633-44.
Chung et al., 2002, Blood, 100(3): 982-90.
Day et al., 2005, Dev. Cell 8:739-750
Fedi et al., 1999, *J Biol Chem* 274:19465-72
Finch, et al. 1997. *Proc Natl Acad Sci USA* 94:6770-6775
Fujita, and Janz, 2007. *Mol Cancer* 6:71.
Fulciniti, et al 2007. *Blood* 110:169a (#551).
Gallea et al., 2001, *Bone* 28:491-8
Galli, et al. 2006. *Dev Dyn* 235:681-690.
Giuliani, et al 2007. *Cancer Res* 67:7665-7674.

Giuliani et al., 2001, *Blood* 98:3527-3533
Glass et al., 2005, *Dev Cell* 8:751-764.
Golub et al., 1999, *Science* 286:531-7.
Gong et al., 2001 *Cell* 107:513-523
Gregory et al., 2003, *J Biol Chem* 278:28067-28078
Grotewold et al., 2002, EMBO J. 21:966-975
Guise et al., 2002, *Bone* 30:670-676.
Gunn et al., 2004, DKK1 and IL-6 in mesenchymal and non-hematopoetic stem cells: Focus on Adult Stem cells, New Orleans, La., Oct. 14-16, 2004.
Gunn, et al 2006. *Stem Cells* 24:986-991.
Haaber, et al 2007. *Br J. Haematol.*
Hall et al., 2005, *Cancer Res.* 65:7554-7560.
Hall et al., 2006, J. Cell Biochem. 97:661-672.
Heath, et al 2007. *Cancer Res* 67:202-208.
Holmen, et al. 2005. *J Biol Chem* 280:21162-21168.
Hu et al., 2005, Development 132(1): 215-25.
Iton et al., 2001, Embo J, 20(15): 4132-4142.
Jackson, et al. 2005. *Bone* 36:585-598.
Johnson et al., 2006, Rev. Endocr. Metab Disord.
Katagiri et al., 1994, *J Cell Biol* 127:1755-66
Katagiri, et al. 1994. *J Cell Biol* 127:1755-1766.
Kato et al., 2002, J Cell Biol, 157(2): 103-114.
Kawano, Y., and Kypta, R. 2003. *J Cell Sci* 116:2627-2634.
Kishimoto, T. 2005. *Annu Rev Immunol* 23:1-21.
Kokubu et al., 2004, development, 131: 5469-80.
Kong, et al. 1999. *Nature* 397:315-323.
Korinek et al., 1997, Methods 15(4): 402-8.
Krishnan et al., 2006, *J. Clin. Invest* 116:1202-1209
Lacey, et al. 1998. *Cell* 93:165-176.
Li et al., 2006, *Bone* 39:754-766
Li et al., 2005, *Nat Genet.* 37(9):945-952.
Lipton, et al 2002. *Clin Cancer Res* 8:2306-2310.
Little, et al. 2002. *Am J Hum Genet.* 70:11-19.
Livak and Schmittgen, 2001., *Methods* 25:402-408.
Mao et al., 2001, *Nature* 411:321-325
Mao, et al. 2002. *Nature* 417:664-667.
Mhalaviele et al., J cell Biochem 94 (2): 403-18.
Morvan et al., 2006, J. Bone Miner. Res. 21:934-945
Mukhopadhyay et al., 2001, *Dev. Cell* 1:423-434
Nakashima et al., 2005, J Biol Chem, 94(2): 403-18.
Nelson and Nusse, 2004, Science, 202(5663): 1483-1487.
Nishimura et al., 1998, J Biol chem 273: 872-9.
Oyajobi, et al 2001. *Cancer Res* 61:2572-2578.
Pearse et al., 2001, *Proc. Natl. Acad. Sci. USA* 98:11581-11586
Politou et al., 2006, *Int. J Cancer* 119:1728-1731
Qiang and Rudikoff, 2004, Front Biosci 9: 1000-1010.
Qiang et al., 2003, Oncogene, 22: 1536-45.
Qiang et al., 2002, Blood, 99: 4138-46.
Qiang, et al., 2005. *Blood* 106:1786-1793.
Rawadi et al., 2003, Bone Miner Res, 18(10); 1842-1853.
Roman-Roman et al. Wnt-mediated signalling via LRP5 and beta-catenin induce osteoblast differentiation and mediates the effects of BMP2, American Society of Bone Mineral Research, 2002.
Roodman, G. D. 2004. *Blood Cells Mol Dis* 32:290-292.
Semenov, et al. 2005. *J Biol Chem* 280:26770-26775.
Seidel, et al 2001. *Blood* 98:2269-2271.
Simonet, et al. 1997. *Cell* 89:309-319.
Suda, et al 1999. *Endocr Rev* 20:345-357.
Spencer et al., G J, 2006, *J. Cell Sci.* 119:1283-1296
Spinella-Jaegle et al., 2001, *Bone* 29:323-30.
Stewart et al., 2006, *J Cell Biochem.* 2006
Szulc, et al 2006. *Nat Methods* 3:109-116.
Taube, et al 1992. *Eur J Haematol* 49:192-198.
Terpos, et al. 2003. *Blood* 102:1064-1069.
Tian et al., 2003, *N Engl J Med* 349: 2483-2494.
Van der Horst et al., 2005, J Bone Miner Res 10(10): 1867-77.
Vanderkerken, et al 2003. *Cancer Res* 63:287-289.
Van Noort et al., 2002, J Biol chem 277(20): 17901-5.
Westfall and Young. Resampling-based multiple testing: Examples and methods for p-value adjustment. Hoboken, N.J.: Wiley-Interscience, 360 (1993).
Willert et al., 2002, BMC Dev biol 2: 8-15.
Yaccoby et al., 1998, *Blood* 92: 2908-2913.
Yaccoby et al., 2002, *Br. J Hematol* 116:278-290.
Yaccoby et al., 2004, *Cancer Res,* 64:2016-2023.
Yata & Yaccoby, 2004, Leukemia, 18:1891-1897.
Yaccoby et al. 2007. *Blood* 109:2106-2111.
Zhan et al., 2002, *Blood* 99:1745-1757.
Zhan et al., 2003, *Blood* 101:1128-1140

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

What is claimed is:

1. A method of controlling bone loss characterized by increased DKK1 expression in an individual, comprising the step of:
   administering to said individual a pharmacologically effective amount of a DKK1 specific antibody that binds a DKK1 protein consisting of the amino acid sequence encoded by the DKK1 gene of SEQ ID NO: 47, wherein said administration inhibits DKK1 at the protein level, and prevents further bone loss in the individual.

2. The method of claim 1, wherein said inhibition of DKK1 blocks induction of Wnt ligand, restores RANK/OPG levels, or both.

3. The method of claim 1, wherein said individual has post-menopausal osteoporosis.

4. The method of claim 1, wherein said bone loss is caused by breast cancer metastasis to the bone or prostate cancer metastasis to the bone.

5. A method of treating bone disease characterized by increased DKK1 expression in an individual, comprising the step of:
   administering to said individual a pharmacologically effective amount of a DKK1 specific antibody that binds a DKK1 protein consisting of the amino acid sequence encoded by the DKK1 gene of SEQ ID NO: 47, such that said administration blocks induction of Wnt ligand, restores RANK/OPG levels, or both.

6. The method of claim 5, wherein said individual has post-menopausal osteoporosis.

7. The method of claim 5, wherein said bone disease is caused by breast cancer metastasis to the bone or prostate cancer metastasis to the bone.

* * * * *

UNITED STATES PATENT AND TRADEMARK OFFICE
CERTIFICATE OF CORRECTION

| | | |
|---|---|---|
| PATENT NO. | : 8,124,087 B2 | Page 1 of 1 |
| APPLICATION NO. | : 12/008771 | |
| DATED | : February 28, 2012 | |
| INVENTOR(S) | : John D. Shaughnessy, Jr., Bart Barlogie and Ya-wei Qiang | |

It is certified that error appears in the above-identified patent and that said Letters Patent is hereby corrected as shown below:

On the title page under item (73) Assignee, "Board of Trustees of the University of Arkansas, Little Rock, AK (US)" should read --Board of Trustees of the University of Arkansas, Little Rock, AR (US)--.

Signed and Sealed this
Seventeenth Day of April, 2012

David J. Kappos
*Director of the United States Patent and Trademark Office*

SEQUENCE LISTING

<160> NUMBER OF SEQ ID NOS: 47

<210> SEQ ID NO 1
<211> LENGTH: 22
<212> TYPE: DNA
<213> ORGANISM: artificial sequence
<220> FEATURE:
<223> OTHER INFORMATION: Fz1 forward primer

<400> SEQUENCE: 1
atgtgtatgt gcgtgtggac cg                                              22

<210> SEQ ID NO 2
<211> LENGTH: 23
<212> TYPE: DNA
<213> ORGANISM: artificial sequence
<220> FEATURE:
<223> OTHER INFORMATION: Fz1 reverse primer

```
<400> SEQUENCE: 2
gggagatgct gaaggaaatg acc                                     23

<210> SEQ ID NO 3
<211> LENGTH: 22
<212> TYPE: DNA
<213> ORGANISM: artificial sequence
<220> FEATURE:
<223> OTHER INFORMATION: Fz2 forward primer

<400> SEQUENCE: 3
aaataggttg ggttggaggg ag                                      22

<210> SEQ ID NO 4
<211> LENGTH: 24
<212> TYPE: DNA
<213> ORGANISM: artificial sequence
<220> FEATURE:
<223> OTHER INFORMATION: Fz2 reverse primer

<400> SEQUENCE: 4
aaacaggaga gacggttgag agcg                                    24

<210> SEQ ID NO 5
<211> LENGTH: 24
<212> TYPE: DNA
<213> ORGANISM: artificial sequence
<220> FEATURE:
<223> OTHER INFORMATION: Fz3 forward primer

<400> SEQUENCE: 5
tattgaggag gatggaacca gtgc                                    24

<210> SEQ ID NO 6
<211> LENGTH: 24
<212> TYPE: DNA
<213> ORGANISM: artificial sequence
<220> FEATURE:
<223> OTHER INFORMATION: Fz3 reverse primer

<400> SEQUENCE: 6
caaagcagtc accacacata gagg                                    24

<210> SEQ ID NO 7
<211> LENGTH: 25
<212> TYPE: DNA
<213> ORGANISM: artificial sequence
<220> FEATURE:
<223> OTHER INFORMATION: Fz4 forward primer

<400> SEQUENCE: 7
tagttggatg ccgatgaact gactg                                   25

<210> SEQ ID NO 8
<211> LENGTH: 24
<212> TYPE: DNA
<213> ORGANISM: artificial sequence
<220> FEATURE:
<223> OTHER INFORMATION: Fz4 reverse primer

<400> SEQUENCE: 8
ttccccctct tctctctctt tacc                                    24

<210> SEQ ID NO 9
<211> LENGTH: 22
```

```
<212> TYPE: DNA
<213> ORGANISM: artificial sequence
<220> FEATURE:
<223> OTHER INFORMATION: Fz5 forward primer

<400> SEQUENCE: 9
acattcgcca ccttctggat tg                                              22

<210> SEQ ID NO 10
<211> LENGTH: 21
<212> TYPE: DNA
<213> ORGANISM: artificial sequence
<220> FEATURE:
<223> OTHER INFORMATION: Fz5 reverse primer

<400> SEQUENCE: 10
ttttggttgc ccacatagca g                                               21

<210> SEQ ID NO 11
<211> LENGTH: 21
<212> TYPE: DNA
<213> ORGANISM: artificial sequence
<220> FEATURE:
<223> OTHER INFORMATION: Fz6 forward primer

<400> SEQUENCE: 11
aatggacact tttggcatcc g                                               21

<210> SEQ ID NO 12
<211> LENGTH: 25
<212> TYPE: DNA
<213> ORGANISM: artificial sequence
<220> FEATURE:
<223> OTHER INFORMATION: Fz6 reverse primer

<400> SEQUENCE: 12
ctctgggtat ctgaatcgtc taacg                                           25

<210> SEQ ID NO 13
<211> LENGTH: 20
<212> TYPE: DNA
<213> ORGANISM: artificial sequence
<220> FEATURE:
<223> OTHER INFORMATION: Fz7 forward primer

<400> SEQUENCE: 13 aaggggaaa ctgcggtatg                                                  20

<210> SEQ ID NO 14
<211> LENGTH: 24
<212> TYPE: DNA
<213> ORGANISM: artificial sequence
<220> FEATURE:
<223> OTHER INFORMATION: Fz7 reverse primer

<400> SEQUENCE: 14
tctctctctc tgctggtctc aacc                                            24

<210> SEQ ID NO 15
<211> LENGTH: 23
<212> TYPE: DNA
<213> ORGANISM: artificial sequence
<220> FEATURE:
<223> OTHER INFORMATION: Fz8 forward primer

<400> SEQUENCE: 15
tccatctggt gggtaatcct gtc                                             23
```

```
<210> SEQ ID NO 16
<211> LENGTH: 23
<212> TYPE: DNA
<213> ORGANISM: artificial sequence
<220> FEATURE:
<223> OTHER INFORMATION: Fz8 reverse primer

<400> SEQUENCE: 16
cggttgtgct gctcatagaa aag                                               23

<210> SEQ ID NO 17
<211> LENGTH: 24
<212> TYPE: DNA
<213> ORGANISM: artificial sequence
<220> FEATURE:
<223> OTHER INFORMATION: Fz9 forward primer

<400> SEQUENCE: 17
cgcccgatta tcttcctttc tatg                                              24

<210> SEQ ID NO 18
<211> LENGTH: 23
<212> TYPE: DNA
<213> ORGANISM: artificial sequence
<220> FEATURE:
<223> OTHER INFORMATION: Fz9 reverse primer

<400> SEQUENCE: 18
tagcagagcc cagtcagttc atc                                               23

<210> SEQ ID NO 19
<211> LENGTH: 23
<212> TYPE: DNA
<213> ORGANISM: artificial sequence
<220> FEATURE:
<223> OTHER INFORMATION: Fz10 forward primer

<400> SEQUENCE: 19
ccaacaagaa cgaccccaac tac                                               23

<210> SEQ ID NO 20
<211> LENGTH: 24
<212> TYPE: DNA
<213> ORGANISM: artificial sequence
<220> FEATURE:
<223> OTHER INFORMATION: Fz10 reverse primer

<400> SEQUENCE: 20
aagaagcaca gcacggacca gatg                                              24

<210> SEQ ID NO 21
<211> LENGTH: 23
<212> TYPE: DNA
<213> ORGANISM: artificial sequence
<220> FEATURE:
<223> OTHER INFORMATION: TCF1 forward primer

<400> SEQUENCE: 21
acgaacattt cagcagtcca cac                                               23

<210> SEQ ID NO 22
<211> LENGTH: 23
<212> TYPE: DNA
<213> ORGANISM: artificial sequence
<220> FEATURE:
<223> OTHER INFORMATION: TCF1 reverse primer
```

```
<400> SEQUENCE: 22
gcattgaggg gtttcttgat gac                                            23

<210> SEQ ID NO 23
<211> LENGTH: 22
<212> TYPE: DNA
<213> ORGANISM: artificial sequence
<220> FEATURE:
<223> OTHER INFORMATION: TCF3 forward primer

<400> SEQUENCE: 23
caacgaatcg gagaatcaga gc                                             22

<210> SEQ ID NO 24
<211> LENGTH: 22
<212> TYPE: DNA
<213> ORGANISM: artificial sequence
<220> FEATURE:
<223> OTHER INFORMATION: TCF3 reverse primer

<400> SEQUENCE: 24
atggcgacct tgtgtccttg ac                                             22

<210> SEQ ID NO 25
<211> LENGTH: 21
<212> TYPE: DNA
<213> ORGANISM: artificial sequence
<220> FEATURE:
<223> OTHER INFORMATION: TCF4 forward primer

<400> SEQUENCE: 25
tgcctggtgg gtgaaaaatg c                                              21

<210> SEQ ID NO 26
<211> LENGTH: 22
<212> TYPE: DNA
<213> ORGANISM: artificial sequence
<220> FEATURE:
<223> OTHER INFORMATION: TCF4 reverse primer

<400> SEQUENCE: 26
cttgagggtt tgtctgctct gg                                             22

<210> SEQ ID NO 27
<211> LENGTH: 22
<212> TYPE: DNA
<213> ORGANISM: artificial sequence
<220> FEATURE:
<223> OTHER INFORMATION: LEF1 forward primer

<400> SEQUENCE: 27
ttctcttttt ctcccctccc cc                                             22

<210> SEQ ID NO 28
<211> LENGTH: 22
<212> TYPE: DNA
<213> ORGANISM: artificial sequence
<220> FEATURE:
<223> OTHER INFORMATION: LEF1 reverse primer

<400> SEQUENCE: 28
aaacctctcc acggattcct cg                                             22

<210> SEQ ID NO 29
<211> LENGTH: 22
```

```
<212> TYPE: DNA
<213> ORGANISM: artificial sequence
<220> FEATURE:
<223> OTHER INFORMATION: Dkk1 reverse primer

<400> SEQUENCE: 29
gcaaaagcac caaccacact tg                                              22

<210> SEQ ID NO 30
<211> LENGTH: 21
<212> TYPE: DNA
<213> ORGANISM: artificial sequence
<220> FEATURE:
<223> OTHER INFORMATION: Dkk2 forward primer

<400> SEQUENCE: 30
aatgcggaag aatgagggat g                                               21

<210> SEQ ID NO 31
<211> LENGTH: 21
<212> TYPE: DNA
<213> ORGANISM: artificial sequence
<220> FEATURE:
<223> OTHER INFORMATION: Dkk2 reverse primer

<400> SEQUENCE: 31
tgccaatctg aaggaaatgc c                                               21

<210> SEQ ID NO 32
<211> LENGTH: 23
<212> TYPE: DNA
<213> ORGANISM: artificial sequence
<220> FEATURE:
<223> OTHER INFORMATION: Dkk3 forward primer

<400> SEQUENCE: 32
cgtggacttg gcaaaatgta acc                                             23

<210> SEQ ID NO 33
<211> LENGTH: 24
<212> TYPE: DNA
<213> ORGANISM: artificial sequence
<220> FEATURE:
<223> OTHER INFORMATION: Dkk3 reverse primer

<400> SEQUENCE: 33
gagcactggc tttcagaggt attg                                            24

<210> SEQ ID NO 34
<211> LENGTH: 21
<212> TYPE: DNA
<213> ORGANISM: artificial sequence
<220> FEATURE:
<223> OTHER INFORMATION: Dkk4 forward primer

<400> SEQUENCE: 34
aagccccaga aatcttccag c                                               21

<210> SEQ ID NO 35
<211> LENGTH: 23
<212> TYPE: DNA
<213> ORGANISM: artificial sequence
<220> FEATURE:
<223> OTHER INFORMATION: Dkk4 reverse primer

<400> SEQUENCE: 35
tgaacacaac aacaagtccc gtg                                             23
```

<210> SEQ ID NO 36
<211> LENGTH: 25
<212> TYPE: DNA
<213> ORGANISM: artificial sequence
<220> FEATURE:
<223> OTHER INFORMATION: mDkk1 forward primer

<400> SEQUENCE: 36
acacacacac acacacacac acatc                                      25

<210> SEQ ID NO 37
<211> LENGTH: 22
<212> TYPE: DNA
<213> ORGANISM: artificial sequence
<220> FEATURE:
<223> OTHER INFORMATION: hDkk1 forward primer

<400> SEQUENCE: 37
ccaacgcgat caagaacctg cc                                         22

<210> SEQ ID NO 38
<211> LENGTH: 21
<212> TYPE: DNA
<213> ORGANISM: artificial sequence
<220> FEATURE:
<223> OTHER INFORMATION: hDkk1 reverse primer

<400> SEQUENCE: 38
gatggtgatc tttctgtatc c                                          21

<210> SEQ ID NO 39
<211> LENGTH: 21
<212> TYPE: DNA
<213> ORGANISM: artificial sequence
<220> FEATURE:
<223> OTHER INFORMATION: hDkk2 forward primer

<400> SEQUENCE: 39
ctgatggtgg agagctcaca g                                          21

<210> SEQ ID NO 40
<211> LENGTH: 23
<212> TYPE: DNA
<213> ORGANISM: artificial sequence
<220> FEATURE:
<223> OTHER INFORMATION: hDkk2 reverse primer

<400> SEQUENCE: 40
cctgatggag cactggtttg cag                                        23

<210> SEQ ID NO 41
<211> LENGTH: 19
<212> TYPE: DNA
<213> ORGANISM: artificial sequence
<220> FEATURE:
<223> OTHER INFORMATION: hDkk3 forward primer

<400> SEQUENCE: 41
agtacacctg ccagccatg                                             19

<210> SEQ ID NO 42
<211> LENGTH: 22
<212> TYPE: DNA
<213> ORGANISM: artificial sequence
<220> FEATURE:
<223> OTHER INFORMATION: hDkk3 reverse primer

```
<400> SEQUENCE: 42
ctccaggtct tccagctcct gg                                              22

<210> SEQ ID NO 43
<211> LENGTH: 22
<212> TYPE: DNA
<213> ORGANISM: artificial sequence
<220> FEATURE:
<223> OTHER INFORMATION: hDkk4 forward primer

<400> SEQUENCE: 43
ggtcctggac ttcaacaaca tc                                              22

<210> SEQ ID NO 44
<211> LENGTH: 20
<212> TYPE: DNA
<213> ORGANISM: artificial sequence
<220> FEATURE:
<223> OTHER INFORMATION: hDkk4 reverse primer

<400> SEQUENCE: 44
cttaatcgag catgctgccg                                                 20

<210> SEQ ID NO 45
<211> LENGTH: 50
<212> TYPE: DNA
<213> ORGANISM: artificial sequence
<220> FEATURE:
<223> OTHER INFORMATION: siRNA specific to human DKK1 gene

<400> SEQUENCE: 45
caatggtctg gtacttattc ccgaaggatt aagtaccaga ccattgcacc                50

<210> SEQ ID NO 46
<211> LENGTH: 60
<212> TYPE: DNA
<213> ORGANISM: artificial sequence
<220> FEATURE:
<223> OTHER INFORMATION: control shRNA sequence

<400> SEQUENCE: 46
gatccccgac acgcgacttg taccacttca agagagtggt acaagtcggt                50
cgtcttttta                                                            60

<210> SEQ ID NO 47
<211> LENGTH: 1815
<212> TYPE: DNA
<213> ORGANISM: artificial sequence
<220> FEATURE:
<223> OTHER INFORMATION: human Dickkopf-1 gene

<400> SEQUENCE: 47
gcagagctct gtgctccctg cagtcaggac tctgggaccg caggggggctc               50 ccggaccctg actctgcagc cgaaccggca cggtttcgtg gggacccagg                100
cttgcaaagt gacggtcatt ttctctttct ttctccctct tgagtccttc                150
tgagatgatg gctctgggcg cagcgggagc tacccgggtc tttgtcgcga                200
tggtagcggc ggctctcggc ggccaccctc tgctgggagt gagcgccacc                250
ttgaactcgg ttctcaattc caacgctatc aagaacctgc ccccaccgct                300
gggcggcgct gcggggcacc caggctctgc agtcagcgcc gcgccgggaa                350
tcctgtaccc gggcgggaat aagtaccaga ccattgacaa ctaccagccg                400
```

-continued

```
tacccgtgcg cagaggacga ggagtgcggc actgatgagt actgcgctag        450
tcccacccgc ggaggggacg caggcgtgca aatctgtctc gcctgcagga        500
agcgccgaaa acgctgcatg cgtcacgcta tgtgctgccc cgggaattac        550
tgcaaaaatg gaatatgtgt gtcttctgat caaaatcatt tccgaggaga        600
aattgaggaa accatcactg aaagctttgg taatgatcat agcaccttgg        650
atgggtattc cagaagaacc accttgtctt caaaaatgta tcacaccaaa        700
ggacaagaag gttctgtttg tctccggtca tcagactgtg cctcaggatt        750
gtgttgtgct agacacttct ggtccaagat ctgtaaacct gtcctgaaag        800
aaggtcaagt gtgtaccaag cataggagaa aaggctctca tggactagaa        850
atattccagc gttgttactg tggagaaggt ctgtcttgcc ggatacagaa        900
agatcaccat caagccagta attcttctag gcttcacact tgtcagagac        950
actaaaccag ctatccaaat gcagtgaact cctttttatat aatagatgct      1000 atgaaaacct tttatgacct tcatcaactc aatcctaagg atatacaagt      1050
tctgtggttt cagttaagca ttccaataac accttccaaa aacctggagt      1100
gtaagagctt tgtttcttta tggaactccc ctgtgattgc agtaaattac      1150
tgtattgtaa attctcagtg tggcacttac ctgtaaatgc aatgaaactt      1200
ttaattattt ttctaaaggt gctgcactgc ctattttttcc tcttgttatg      1250 taaattttttg tacacattga ttgttatctt gactgacaaa tattctatat      1300
tgaactgaag taaatcattt cagcttatag ttcttaaaag cataaccctt      1350 tacccccattt aattctagag tctagaacgc aaggatctct tggaatgaca      1400
aatgataggt acctaaaatg taacatgaaa atactagctt attttctgaa      1450
atgtactatc ttaatgctta aattatattt ccctttaggc tgtgatagtt      1500
tttgaaataa aatttaacat ttaatatcat gaaatgttat aagtagacat      1550 acatttttggg attgtgatct tagaggtttg tgtgtgtgta cgtatgtgtg      1600
tgttctacaa gaacggaagt gtgatatgtt taaagatgat cagagaaaag      1650
acagtgtcta aatataagac aatattgatc agctctagaa taactttaaa      1700
gaaagacgtg ttctgcattg ataaactcaa atgatcatgg cagaatgaga      1750
gtgaatctta cattactact ttcaaaaata gtttccaata aattaataat      1800
acctaaaaaa aaaaa                                             1815
```